(12) United States Patent
Hubbell et al.

(10) Patent No.: US 7,670,605 B2
(45) Date of Patent: *Mar. 2, 2010

(54) CONJUGATE ADDITION REACTIONS FOR THE CONTROLLED DELIVERY OF PHARMACEUTICALLY ACTIVE COMPOUNDS

(75) Inventors: Jeffrey A. Hubbell, Morges (CH); Donald L. Elbert, St. Louis, MO (US); Ronald Schoenmakers, Zürich (CH)

(73) Assignees: Eidgenossische Technische Hochschule Zurich, Zurich (CH); Universitat Zurich, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/192,655

(22) Filed: Aug. 15, 2008

(65) Prior Publication Data

US 2009/0098083 A1 Apr. 16, 2009

Related U.S. Application Data

(63) Continuation of application No. 11/257,818, filed on Oct. 25, 2005, now Pat. No. 7,413,739, which is a continuation of application No. 09/586,937, filed on Jun. 2, 2000, now Pat. No. 6,958,212, which is a continuation-in-part of application No. 09/496,231, filed on Feb. 1, 2000.

(60) Provisional application No. 60/118,093, filed on Feb. 1, 1999.

(51) Int. Cl.
*A61K 39/00* (2006.01)
*C12Q 1/68* (2006.01)
*C12N 9/96* (2006.01)
*C07H 21/04* (2006.01)

(52) U.S. Cl. ............... 424/178.1; 424/94.3; 424/180.1; 424/181.1; 435/6; 435/188; 536/24.1

(58) Field of Classification Search ............... 435/6, 435/188; 536/24.1; 424/94.3, 177, 180, 424/181, 178.1, 180.1, 181.1
See application file for complete search history.

(56) References Cited

U.S. PATENT DOCUMENTS

| 4,618,400 A | 10/1986 | Wood et al. |
| 4,711,903 A | 12/1987 | Mueller et al. |
| 5,268,305 A | 12/1993 | Ribi et al. |
| 5,292,514 A | 3/1994 | Capecchi et al. |

(Continued)

FOREIGN PATENT DOCUMENTS

CA 2281602 8/1998

(Continued)

OTHER PUBLICATIONS

Aldrich, "Poly(ethylene glycol-400)" and "Poly(ethylene glycol-400)diacrylate" Aldrich Catalog of Fine Chemicals, p. 1211, 1996.

(Continued)

*Primary Examiner*—Jezia Riley
(74) *Attorney, Agent, or Firm*—Kristina Bieker-Brady; Clark & Elbing LLP

(57) ABSTRACT

The invention features polymeric biomaterials formed by nucleophilic addition reactions to conjugated unsaturated groups. These biomaterials may be used for medical treatments.

27 Claims, 17 Drawing Sheets

U.S. PATENT DOCUMENTS

| | | | |
|---|---|---|---|
| 5,294,690 | A | 3/1994 | Iguchi et al. |
| 5,330,911 | A | 7/1994 | Hubbell et al. |
| 5,410,016 | A | 4/1995 | Hubbell et al. |
| 5,427,915 | A | 6/1995 | Ribi et al. |
| 5,428,014 | A | 6/1995 | Labroo et al. |
| 5,446,090 | A | 8/1995 | Harris |
| 5,529,914 | A | 6/1996 | Hubbell et al. |
| 5,567,422 | A | 10/1996 | Greenwald |
| 5,573,934 | A | 11/1996 | Hubbell et al. |
| 5,575,815 | A | 11/1996 | Slepian et al. |
| 5,612,390 | A | 3/1997 | Iguchi et al. |
| 5,635,207 | A | 6/1997 | Grinstaff et al. |
| 5,648,506 | A | 7/1997 | Desai et al. |
| 5,702,717 | A | 12/1997 | Cha et al. |
| 5,752,974 | A | 5/1998 | Rhee et al. |
| 5,801,033 | A | 9/1998 | Hubbell et al. |
| 5,817,840 | A | 10/1998 | Nicolaou et al. |
| 5,852,182 | A | 12/1998 | Cook et al. |
| 5,858,746 | A | 1/1999 | Hubbell et al. |
| 5,874,500 | A | 2/1999 | Rhee et al. |
| 5,880,131 | A | 3/1999 | Greenwald et al. |
| 5,897,955 | A | 4/1999 | Drumheller |
| 5,932,462 | A | 8/1999 | Harris et al. |
| 5,958,874 | A | 9/1999 | Clark et al. |
| 5,965,588 | A | 10/1999 | Vazquez et al. |
| 6,136,564 | A | 10/2000 | Kopetzki et al. |
| 6,958,212 | B1 * | 10/2005 | Hubbell et al. ............... 435/6 |
| 7,291,673 | B2 | 11/2007 | Hubbell et al. |
| 2003/0044468 | A1 | 3/2003 | Cellesi et al. |
| 2003/0059906 | A1 | 3/2003 | Hubbell et al. |

FOREIGN PATENT DOCUMENTS

| | | |
|---|---|---|
| CA | 2378533 | 10/2001 |
| GB | 1348045 | 3/1974 |
| WO | WO 95/13312 | 5/1995 |
| WO | WO 97/22371 | 6/1997 |
| WO | WO 98/32466 | 7/1998 |
| WO | WO 99/14259 | 3/1999 |
| WO | WO 99/22770 | 5/1999 |
| WO | WO 99/34833 | 7/1999 |
| WO | WO 00/09087 | 2/2000 |
| WO | WO 00/44808 | 8/2000 |
| WO | WO 01/02017 | 1/2001 |
| WO | WO 03/040235 A1 | 5/2003 |

OTHER PUBLICATIONS

Aida et al., "Zinc N-substituted Porphyrins as Novel Initiators for the Living and Immortal Polymerizations of Episulfide," Macromolecules, 23:3887-3892 (1990).

Baker, "Controlled Release of Biologically Active Agents," Bruck, ed., p. 84-131 John Wiley and Sons, New York (1987).

Ballini et al., "Amberlyst A-27, an Efficient Heterogeneous Catalyst for the Michael Reactions of Nitroalkanes with β-Substituted Alkene Acceptors," J. Org. Chem. 61:3209-3211, 1996.

Blume et al., "Specific Targeting with Poly(ethylene glycol)-modified Liposomes: Coupling of Homing Devices to the Ends of the Polymeric Chains Combines Effective Target Binding with Long Circulation Times," Biochim. Biophys. Acta., 1149:180-184(1993).

Booth et al., "Effects of Block Architecture and Composition on the Association Properties of Poly(oxyalkylene) Copolymers in Aqueous Solution," Macromol. Chem. Rapid Commun., 21:501-527 (2000).

Boyland et al., "Enzymes Catalysing Conjugations of Glutathione with Alpha-beta-unsaturated Carbonyl Compounds," Biochem. J. 109:651-661, 1968.

Chasseaud, "Distribution of Enzymes that Catalyse Reactions of Glutathione with Alpha Beta-unsaturated Compounds," Biochem. J. 131:765-769, 1973.

Deutsch et al., "Synthesis of Congeners and Prodrugs. 3. Water-Soluble Prodrugs of Taxol with Potent Antitumor Activity," Journal of Medicinal Chemistry 32:788-792 (1989).

Discher et al., "Polymersomes: Tough Vesicles Made from Diblock Copolymers," Science, 284:1143-1146 (1999).

Dumitriu et al., "Polymeric Drug Carriers," In Polymeric Biomaterials, Dumitriu, ed., p. 435-449 and 466-724, Marcel Dekker, New York (1994).

Duncan et al., "Soluble Synthetic Polymers as Potential Drug Carriers," Adv. In Polym. Sci. 57:51-101 (1984).

Eisele et al., "Kinetics of Photocrosslinking Reactions of a DCPA/EA Matrix in the Presence of Thiols and Acrylates," J. Polym. Sci., Polym. Chem. Ed. 35:2333-2345, 1997.

Fan et al., "Molecular Recognition and Catalysis: Incorporation of an Oxyanion Hole into a Synthetic Receptor," New J. Chem. 21(1):81-85, 1997.

Friedman et al., "Relative Nucleophilic Reactivities of Amino Groups and Mercaptide Ions in Addition Reactions with α,β-Unsaturated Compounds," J. Am. Chem. Soc. 87(16):3672-3682, 1965.

Gabizon, Targeting Folate Receptor with Folate Linked to Extremities of Poly(ethylene glycol)-Grafted Liposomes: In Vitro Studies, Bioconjugate Chem., 10:289-298 (1999).

Ghandehari et al., "In Vitro Degradation of pH-sensitive Hydrogels Containing Aromatic Azo Bonds," Biomaterials 18:861-872, 1997.

Greenwald et al., "Drug Delivery Systems: Water Soluble Taxol-2'-Poly(ethylene glycol) Ester Prodrugs-Design and in Vivo Effectiveness," J. Med. Chem. 39:424-431 (1996).

Greenwald et al "Camptothecin-20-PEG Ester Transport Forms: the Effect of Spacer Groups on Antitumor Activity" Bioorganic & Medicinal Chemistry, 6:551-562, 1998.

Harata, K., Abe Y., and Muraki, M., "Full-matrix Least Squares Refinement of Lysozymes and Analysis of Anisotropic Thermal Motion," Proteins. 30:232-243, 1998.

Harata K et al., "PDB: 1JSF" GenomeNet:DBGet http://www.genome.jp/dbget-bin/www_bget?pdb+1JSFarchived Jan. 5, 1998 (accessed online May 16, 2008), 5 pages.

Hern et al., "Incorporation of Adhesion Peptides into Non-adhesive Hydrogels Useful for Tissue Resurfacing," J. Biomed. Mater. Res. 39:266-276, 1998.

Hirai et al., "Ph-induced Structure Change of Poly(vinyl alcohol) Hydrogel Crosslinked with Poly(acrylic acid)," Die Angewandte Makromolekulare Chemie 240:213-219, 1996.

Hubbell, J.A., "Hydrogel Systems for Barriers and Local Drug Delivery in the Control of Wound Healing," J. Controlled Release. 1996, 39, 305-313.

Inoue et al., "Gene Therapy of Human Bladder Cancer with Adenovirus-mediated Antisense Basic Fibroblast Growth Factor," Clinical Cancer Research, 6:4422-4431 (2000).

Ishihara et al., "Tris(pentafluorphenyl)boron as an Efficient, Air Stable, and Water Tolerant Lewis Acid Catalyst," Bull. Chem. Soc. Jpn. 68:1721-1730, 1995.

Kawai et al., "New Application of Solid Acid to Carbon-Carbon Bond Formation Reactions: Clay Montmorillonite-Catalyzed Aldol Reactions of Silyl Enol Ethers with Aldehydes and Acetals," Bull. Chem. Soc. Jpn. 61:1237-1245, 1988.

Kito et al., "Biocompatible Coatings for Luminal and Outer Surfaces of Small-caliber Artificial Grafts," Journal of Biomedical Materials Research 30:321-330, 1996.

Kopecek et al. "Controlled Release of Drug Model from N-(2-Hydroxypropyl)-methacrylamide Copolymers" Ann. N. Y. Acad. Sci. 1985, 446:93-104.

Kudela, V. "Hydrogels" Encyclopedia of Polymer Science and Engineering, (Ed. Mark, H., et al.), vol. 7, pp. 783-807, 1987.

Lasic et al., ed. Stealth Liposomes, Chaiters 2, 4, and 9, CRC Press: Boca Raton, FL, (1995).

Lau et al., "Conjugation of Doxorubicin to Monoclonal Anti-carcinoembryonic Antigen Antibody via Novel Thiol-directed Cross-linking Reagents," Bioorganic & Medicinal Chemistry 3:1299-1304 (1995).

Lau et al., "Novel Doxorubicin-Monoclonal Anti-carcinoembryonic Antigen Antibody Immunoconjugate Activity in vitro," *Biorganic & Medicinal Chemistry* 3:1305-1312 (1995).

Luginbuehl et al., "Localized Delivery of Growth Factors for Bone Repair," *Eur. J. Pharm. Biopharm.* 58:197-208 (2004).

March J., "Addition to Carbon-Carbon Multiple Bonds" *Advanced Organic Chemistry: Reactions, Mechanisms, and Structure.* 4th Ed. Chapter 15, pp. 734-770 and 795-797, 1992.

Mathur et al., "Methods for Synthesis of Hydrogel Networks: A Review," *Journal of Macromolecular Science-Reviews in Macromolecular Chemistry and Physics* Cc:36(2):405-430, 1996.

Moghaddam et al., "Molecular Design of 3-Dimensional Artificial Extracellular-matrix—Photosensitive Polymers Containing Cell Adhesive Peptide," *Journal of Polymer Science: Part A: Polymer Chemistry* 31:1589-1597, 1993..

Morpurgo et al., "Preparation and Characterization of Poly(ethylene glycol) Vinyl Sulfone," *Bioconjugate Chem.* 7:363-368, 1996.

Mortensen, "Block Copolymer in Aqueous Solution: Micelle Formation and Hard-sphere Crystallization," *Prog. Colloid. Polym. Sci.*, 93:72-75 (1993).

Pato et al., "Polymers Containing Enzymatically Degradable Bonds, $9^{a)}$ Chymotrypsin Catalyzed Hydrolysis of a *p*-nitroanilide Drug Model, Bound Via Oligopeptides onto Poly(vinylpyrrolidone-*co*-maleic anhydride)," *Makromol. Chem.* 185:231-237, 1984.

Pathak et al., "Rapid Photopolymerization of Immunoprotective Gels in Contact with Cells and Tissue," *Journal of the American Chem. Society* 114:8311-8312, 1992.

Pendri et al. "Antitumor Activity of Paclitaxel-2'-glycinate Conjugated to Poly(ethylene glycol): a Water-soluble Prodrug" Anti-cancer Drug Design 1998, 13:387-395.

Petka et al., "Reversible Hydrogels from Self-Assembling Artificial Proteins," *Science* 281:389-392, 1998.

Pitt et al., "Controlled Drug Delivery," in *Biodegradation of Polymers, Basic Concepts*, vol. 1, p. 53-80, CRC Press, Boca Raton, Florida (1983).

Ranucci, E. et al., "New polymeric acids containing potentially hydrolysable bonds" *Macromolecules,* 24(16) pp. 4554-4558, 1991.

Romanowska et al., "Michael Additions for Syntheses of Neoglycoproteins," *Methods in Enzymol.* 242:90-101, 1994.

Sawhney et al., "Bioerodible Hydrogels Based on Photopolymerized Poly(ethylene glycol)-co-poly(α-hydroxy acid) Diacrylate Macromers," *Macromolecules* 26:581-587, 1993.

Tanaka et al., "Michael-type Addition of Illudin S, a Toxic Substance from *Lampteromyces japonicus,* with Cysteine and Cysteine-containing Peptides in Vitro,"*Chem. Pharm. Bull.* 44:273-279, 1996.

Torchilin et al., "Poly(ethylene glycol) on the Liposome Surface: on the Mechanism of Polymer-coated Liposome Longevity," Biochim. Biophys. Acta, 1195:11-20 (1994).

Trumbo, D.L. "Polymers based on methyl acrylamidoglycolate methyl ether (MAGME): Michael addition-reactions" *Polymer Bulletin,* 31(5), pp. 523-529, 1993.

Watanabe et al., "First Example of Photoinduced Copolymerizability Enhancement. Copolymerization of Epoxide and Episulfide Initiated with Zinc N-substituted Porphyrin under Visible Light Irradiation," Macromolecules, 24:3970-3972 (1991).

West et al., "Comparison of Covalently and Physically Cross-linked Polyethylene Glycol-based Hydrogels for the Prevention of Postoperative Adhesions in a Rat Model," *Biomaterials* 16:1153-1156, 1995.

Won, "Giant Wormlike Rubber Micelles," Science, 283:960-963, (1999).

Wright et al., *The Chemistry and Pharmacology of Taxol and Its Derivatives,* Farina, ed., p. 110-130 and 165-300, Elsevier, New York (1995).

Yu et al., "Bilayer Morphologies of Self-assembled Crew-cut Aggregates of Amphiphilic PS-b-PEO Diblock Copolymers in Solution," Macromolecules, 31:3509-3518, (1998).

Zalipsky et al., "Peptide Attachment to Extremities of Liposomal Surface Grafted PEG Chains: Preparation of the Long-circulating Form of Laminin Pentapeptide, YIGSR," Bioconjugate Chem., 6:705-708(1995).

Zalipsky, "Long-circulating, Polyethylene Glycol-grafted Immunoliposomes," J. Controlled Release, 39:153-161 (1996).

Zalipsky et al., "Attachment of Drugs to Polyethylene Glycols," *Eur. Polym. J.* 19:1177-1183 (1983).

Zhao et al., "Novel Degradable PEG Esters for Drug Delivery: Synthesis and Characterization," *Polymer Reprints* 38:526-527, 1997.

\* cited by examiner

PEG diacrylate 570 mixture as a function of time

R= Me for methyl ester of paclitaxel side chain

R= 5-beta,20-epoxy-1,2-alpha,4,7-beta,10-beta,13-alpha-hexahydroxy-tax-11-en-9-one 4,10-diacetate 2-benzoate for paclitaxel R= Me for methyl ester of paclitaxel side chain R= 5-beta,20-epoxy-1,2-alpha,4,7-beta,10-beta,13-alpha-hexahydroxy-tax-11-en-9-one
    4,10-diacetate 2-benzoate for paclitaxel

CONJUGATE ADDITION REACTIONS FOR THE CONTROLLED DELIVERY OF PHARMACEUTICALLY ACTIVE COMPOUNDS

CROSS-REFERENCE TO RELATED APPLICATIONS

This application is a continuation of U.S. application Ser. No. 11/257,818, filed Oct. 25, 2005, now U.S. Pat. No. 7,413,739, which is a continuation of U.S. application Ser. No. 09/586,937, filed Jun. 2, 2000, now U.S. Pat. No. 6,958,212, which is a continuation-in-part of U.S. application Ser. No. 09/496,231, filed Feb. 1, 2000, which claims benefit of U.S. Provisional Application No. 60/118,093, filed Feb. 1, 1999, each of which is hereby incorporated by reference.

BACKGROUND OF THE INVENTION

The present invention relates to the release of pharmaceutically active compounds from biomaterials, including bulk materials and colloidal materials. Nucleophilic addition reactions are used for the conjugation of the pharmaceutically active compounds to the polymers to achieve the desirable release rates featured by the compositions of the invention.

Synthetic biomaterials, including polymeric hydrogels and water-soluble copolymers, can be used in a variety of applications, including pharmaceutical and surgical applications. They can be used, for example, to deliver therapeutic molecules to a subject, as adhesives or sealants, as tissue engineering and wound healing scaffolds, and as cell transplant devices.

The use of materials for the release of pharmaceutically active compounds has been studied by several groups. Pitt and Schindler categorized the various types of controlled drug delivery schemes (Pitt et al. Controlled Drug Delivery, CRC Press, Boca Raton, Fla., p. 53-80, 1983). They defined two types of systems in which the drug was covalently attached to a material. Systems in which the drug was pendently attached to the polymer were called Type IV systems, and systems in which the drug was incorporated into the polymer backbone were called Type V systems. This definition of Type V polymers was further expanded by Baker (*Controlled Release of Biologically Active Agents*, p. 84-13 John Wiley and Sons, New York, 1987) who included systems in which a free radical polymerizable group was added to a drug, with subsequent free radical polymerization of the drug alone or with other comonomers to form a material (for examples, see Duncan et al., Adv. In Polym. Sci. 57:51-101, 1984). Type IVb systems are different from Type V systems in that a linker molecule is utilized to connect a drug to an active group on a polymer.

While much progress has been made in the field of polymeric biomaterials, further developments must be made in order for such biomaterials to be used optimally in the body. For the release of a therapeutic compound from a biomaterial over a clinically relevant time-frame, the half-life of the release of the therapeutic compound from the biomaterial should be on the order of weeks or months, rather than on the order of hours or years, as demonstrated for previous biomaterials under physiological conditions. In fact, the clinical usefulness of the delivery of pharmaceutically active compounds from biomaterials has been limited by the rate of release of pharmaceutically active compounds from the biomaterial and the great difficulty and low yields associated with the conjugation of these compounds to the polymer.

SUMMARY OF THE INVENTION

The following new aspects feature compounds and methods that are useful in the coupling of a pharmaceutically active compound to a polymer, using a conjugate addition reaction, and the cross-linking of the polymers to form a biomaterial, in some embodiments using conjugate addition reactions. Alternatively, the cross-linking may be achieved through other mechanisms, such as free radical polymerization. A polymer coupled to a pharmaceutically active compound may also be cross-linked with another polymer to form a copolymer, such as a colloidal biomaterial. The compounds, precursor components, and biomaterials of the invention may be used in the treatment or prevention of a disease, disorder, or infection.

In a first aspect, the invention provides a compound having the formula:

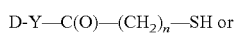

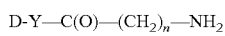

wherein D is a pharmaceutically active moiety; n is 1 or 2; and Y is O, NH, or N.

In a second aspect, the invention features a compound the formula:

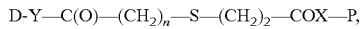

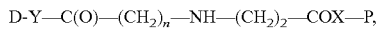

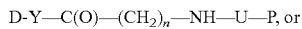

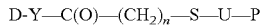

wherein D is a pharmaceutically active moiety; n is 1 or 2; X is N or O; P is a water-soluble polymer or a water swellable polymer having one or more conjugated unsaturated groups; Y is O, NH, or N; and U is the product of the addition of a nucleophile to an electrophilic group that is attached to the polymer. It is also contemplated that the compound may have a hydrocarbon moiety in place of one or more hydrogens in one or more of the methylene ($CH_2$) groups. The half-life of the ester or amide bond onto the pharmaceutically active moiety is between 1 hour and 1 year in an aqueous solution at pH 7.4 and 37° C. Preferably, the half-life is between 1 day and 9 months, more preferably between 2 days and 6 months, and most preferably between 4 days and 3 weeks.

In a third aspect, the invention features a compound having the formula:

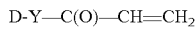

wherein D is a pharmaceutically active moiety, and Y is O, NH, or N. It is also contemplated that the compound may have a hydrocarbon moiety in place of one or more hydrogens in the alkene ($-CH=CH_2$) group.

In a fourth aspect, the invention includes a compound having the formula:

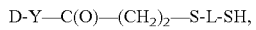

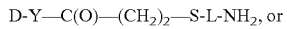

wherein D is a pharmaceutically active moiety; Y is O, NH, or N; and L is a linear or branched linker.

In a fifth aspect, the invention features a compound having the formula:

D-Y—C(O)—(CH$_2$)$_2$—S-L-S—CH$_2$—CH$_2$—CO—X—P;

D-Y—C(O)—(CH$_2$)$_2$—S-L-S—U—P;

D-Y—C(O)—(CH$_2$)$_2$—NH-L-S—CH$_2$—CH$_2$—CO—X—P;

D-Y—C(O)—(CH$_2$)$_2$—NH-L-S—U—P;

D-Y—C(O)—(CH$_2$)$_2$—S-L-NH—CH$_2$—CH$_2$—CO—X—P;

D-Y—C(O)—(CH$_2$)$_2$—S-L-NH—U—P;

D-Y—C(O)—(CH$_2$)$_2$—NH-L-NH—CH$_2$—CH$_2$—CO—X—P; or

D-Y—C(O)—(CH$_2$)$_2$—NH-L-NH—U—P, wherein D is a pharmaceutically active moiety; L is a linear or branched linker; X is O or N; Y is O, NH, or N; P is a water-soluble polymer or a water-swellable polymer having one or more conjugated unsaturated groups; and U is the product of the addition of a nucleophile to an electrophilic group that is attached to the polymer. The half-life the ester or amide bond onto the pharmaceutically active moiety is between 1 hour and 1 year in an aqueous solution at pH 7.4 and 37° C.

A sixth aspect of the invention features a biomaterial formed from the cross-linking of two or more precursor components having the formula:

D-Y—C(O)—(CH$_2$)$_n$—S—(CH$_2$)$_2$—COX—P,

D-Y—C(O)—(CH$_2$)$_n$—NH—(CH$_2$)$_2$—COX—P,

D-Y—C(O)—(CH$_2$)$_n$—NH—U—P,

D-Y—C(O)—(CH$_2$)$_n$—S—U—P,

D-Y—C(O)—(CH$_2$)$_2$—S-L-S—CH$_2$—CH$_2$—CO—X—P,

D-Y—C(O)—(CH$_2$)$_2$—S-L-S—U—P,

D-Y—C(O)—(CH$_2$)$_2$—NH-L-S—CH$_2$—CH$_2$—CO—X—P,

D-Y—C(O)—(CH$_2$)$_2$—NH-L-S—U—P,

D-Y—C(O)—(CH$_2$)$_2$—S-L-NH—CH—CH$_2$—CO—X—P,

D-Y—C(O)—(CH$_2$)$_2$—S-L-NH—U—P,

D-Y—C(O)—(CH$_2$)$_2$—NH-L-NH—CH$_2$—CH$_2$—CO—X—P, or

D-Y—C(O)—(CH$_2$)$_2$—NH-L-NH—U—P, wherein D is a pharmaceutically active moiety; Y is O, NH, or N; L is a linear or branched linker; X is O or N; P is a water-soluble polymer or a water-swellable polymer having one or more conjugated unsaturated groups; and U is the product of the addition of a nucleophile to an electrophilic group that is attached to the polymer. The half-life the ester or amide bond onto the pharmaceutically active moiety is between 1 year and 1 year in an aqueous solution at pH 7.4 and 37° C. In one preferred embodiment, the cross-linking occurs through free radical polymerization or conjugate addition, possibly in the presence of an accelerator. In another preferred embodiment, the cross-linking forms a colloidal material, microsphere, or a nanosphere. The cross-linking may also occur in the presence of sensitive biological molecules or near or at a site in the body of a mammal, such as a human. Preferably, a pharmaceutically active compound is released and delivered to the site.

In a preferred embodiment of the first through sixth aspects of the invention, the pharmaceutically active moiety is derived from one of the group consisting of synthetic organic molecules, naturally occurring organic molecules, nucleic acid molecules, biosynthetic proteins or peptides, naturally occurring peptides or proteins, and modified naturally occurring peptides or proteins. Preferred organic molecules include paclitaxel, doxorubicin, 5-fluorodeoxyuridine, estradiol, 2-methoxyestradiol, and their derivatives.

In preferred embodiments of the second, fourth, fifth, and sixth aspects, the water-soluble or water-swellable polymer is selected from the group consisting of poly(ethylene glycol), poly(ethylene oxide), poly(vinyl alcohol), poly(acrylic acid), poly(ethylene-co-vinyl alcohol), poly(vinyl pyrrolidone), poly(acrylic acid), poly(ethyloxazoline), poly(ethylene oxide)-co-poly(propylene oxide) block copolymers, or water-soluble or water-swellable copolymers containing these polymers, and their derivatives having conjugated unsaturated groups. The unsaturated groups may be identical. One or more of the unsaturated groups may not be coupled to a pharmaceutically active moiety. Preferably, the unsaturated groups are not activated as to undergo nucleophilic substitution reactions. Preferred unsaturated groups include acrylates, methacrylates, acrylamides, methacrylamides, acrylonitriles, quinones, and their derivatives. In another preferred embodiment, the hydrolysis of the compound results in the release of a pharmaceutically active compound having the formula D-OH. D-NH$_2$, or D-NH.

In one preferred embodiment of the fourth through sixth aspects, the linker includes one or more amino acids. Preferably, the linker comprises an adhesion site, growth factor binding site, or protease binding site. Preferred linker also include enzymatically degradable linkers.

If the linker of the fourth through sixth aspects is hydrophilic, it may increase the water solubility of the pharmaceutically active moiety and/or increase the rate of release of the a pharmaceutically active compound derived from D. If the linker is hydrophobic, it may decrease the water solubility of the pharmaceutically active moiety and/or decrease the rate of release of a pharmaceutically active compound derived from D. In other preferred embodiments, the linker includes a nucleophilic group that increases the rate of release of a pharmaceutically active compound having the formula D-OH, D-NH$_2$, or D-NH by reacting with the ester or amide bond onto D. Preferred linkers also include hydrocarbon moieties containing between 1 and 4 carbon atoms, inclusive.

In a seventh aspect, the invention features a method for making a precursor component of a biomaterial. The method includes (a) attaching a pharmaceutically active compound to a linker molecule to produce a compound having the formula:

D-Y—C(O)—(CH$_2$)$_n$—SH or

D-Y—C(O)—(CH$_2$)$_n$—NH$_2$ wherein D is a pharmaceutically active moiety; Y is O, NH, or N; and n is 1 or 2; and (b) coupling the product formed in step (a) to a water soluble polymer or a water swellable polymer having two or more conjugated unsaturated groups by a conjugate addition reaction.

A method for making a precursor component of a biomaterial is also provided by an eighth aspect of the invention. This method includes (a) attaching a pharmaceutically active compound to a linker molecule to produce a compound having the formula:

D-Y—C(O)—CH=CH$_2$ wherein D is a pharmaceutically active moiety, and Y is O, NH, or N; and (b) coupling the product formed in step (a) to a water soluble polymer or a water swellable polymer having two or more conjugated unsaturated groups by a conjugate addition reaction. Preferably, step (a) is performed by condensing an acrylic acid with an alcohol or amine on a pharmaceutically active compound to form an ester or amide bond and produce a modified pharmaceutically active compound.

The ninth aspect of the invention features a method for making a precursor component of a biomaterial which includes (a) attaching a pharmaceutically active compound to a linker to produce a compound having the formula:

D-Y—C(O)—(CH$_2$)$_2$—S-L-SH,

D-Y—C(O)—(CH$_2$)$_2$—NH-L-SH,

D-Y—C(O)—(CH$_2$)$_2$—S-L-NH$_2$, or

D-Y—C(O)—(CH$_2$)$_2$—NH-L-NH$_2$ wherein D is a pharmaceutically active moiety; Y is O, NH, or N; and L is a linear or branched linker; and (b) coupling the product formed in step (a) to a water soluble polymer or a water swellable polymer having two or more conjugated unsaturated groups by a conjugate addition reaction. Preferably step (a) is performed by condensing an acrylic acid with an alcohol or amine on a pharmaceutically active compound to form an ester or amide bond, reacting the product with a compound having one protected amine or thiol and one free amine or thiol, and removing the thiol- or amine-protecting group.

In a tenth aspect, the invention features a method for making a precursor component of a biomaterial that includes (a) condensing a linker consisting of one of the following: a thiol-protected mercaptopropionic acid, a thiol-protected mercaptoacetic acid, an amine-protected aminopropionic acid, or an amine-protected glycine; with an alcohol or amine on a pharmaceutically active compound to form an ester or amide bond and produce a modified pharmaceutically active compound; (b) removing the thiol- or amine-protecting group; and (c) coupling the product formed in step (b) to a water soluble polymer or a water swellable polymer having two or more conjugated unsaturated groups by a conjugate addition reaction.

In an eleventh aspect, the invention provides a method for making a precursor component of a biomaterial. This method includes (a) condensing an acrylic acid with an alcohol or amine on a pharmaceutically active compound to form an ester or amide bond and produce a modified pharmaceutically active compound; (b) reacting the modified pharmaceutically active compound with a linker containing one free thiol or amine and one protected thiol or amine through conjugate addition; (c) removing the thiol- or amine-protecting group; and (d) coupling the product formed in step (c) to a water soluble polymer or a water swellable polymer having two or more conjugated unsaturated groups by a conjugate addition reaction.

In a twelfth aspect, the invention features a method for making a precursor component of a biomaterial. This method includes (a) incorporating a nucleophilic amine or thiol into a pharmaceutically active compound and (b) coupling the product formed in step (a) to a water soluble polymer or a water swellable polymer having two or more conjugated unsaturated groups by a conjugate addition reaction. Preferably, the pharmaceutically active compound is DNA, RNA, peptide, or protein. In one preferred embodiment, the DNA or RNA has a base that is modified to contain a thiol.

In preferred embodiments of the seventh through twelfth aspects, the pharmaceutically active compound is selected from the group consisting of synthesized organic molecules, naturally occurring organic molecules, nucleic acid molecules, biosynthetic proteins or peptides, naturally occurring peptides or proteins, and modified naturally occurring peptides or proteins. Preferred organic molecules include paclitaxel, doxorubicin 5-fluorodeoxyuridine, estradiol, 2-methoxyestradiol, and their derivatives. In one preferred embodiment, the amino acid sequence of the biosynthetic peptide or protein has a cysteine instead of another amino acid found in the corresponding location in a naturally occurring peptide or protein. The attachment of the pharmaceutically active compound to a linker or acrylic acid in step (a) can be performed in the presence of a condensing agent. In other preferred embodiments of these aspects, the water-soluble or water-swellable polymer is selected from the group consisting of poly(ethylene glycol), poly(ethylene oxide), poly(vinyl alcohol), poly(acrylic acid), poly(ethylene-co-vinyl alcohol), poly(vinyl pyrrolidone), poly(acrylic acid), poly(ethyloxazoline), poly(ethylene oxide)-co-poly(propylene oxide) block copolymers, or water-soluble or water-swellable copolymers containing these polymers, and their derivatives having conjugated unsaturated groups. In another preferred embodiment, the conjugated unsaturated groups are identical. Preferred conjugated unsaturated groups included acrylates, methacrylates, acrylamides, methacrylamides, acrylonitriles, and quinones. In preferred embodiments of these aspects, one or more of the unsaturated groups is not coupled to the pharmaceutically active moiety. Preferably, the unsaturated groups are not activated as to undergo nucleophilic substitution reactions. The methods of these aspects of the invention may include a purification step that is performed prior to the last step. Preferably, the pharmaceutically active compound is released from the precursor component as the original unmodified pharmaceutically active compound. In one preferred embodiment, the number of conjugated unsaturated groups in the polymer is greater than the number of amine or thiol groups in the linker.

The linker molecule of the seventh through twelfth aspects of the invention can have the same embodiments as listed for the linker of the fourth through sixth aspects.

In a thirteenth aspect, the invention features a method of making a biomaterial. This method includes (a) attaching a pharmaceutically active compound to a linker molecule or incorporating a nucleophilic amine or thiol into a pharmaceutically active compound, (b) removing any thiol- or amine-protecting groups in the linker, (c) coupling a thiol, amine, or alkene group in the linker or incorporated into the pharmaceutically active compound to a water soluble polymer or a water swellable polymer having two or more conjugated unsaturated groups by a conjugate addition reaction to form a precursor component, and (d) cross-linking the uncoupled conjugated unsaturated groups in one or more of the precursor components. In one preferred embodiment, a polymer that has one or more conjugated unsaturated groups and that is not coupled to a pharmaceutically active moiety is incorporated into the biomaterial by performing the cross-linking in the presence of this polymer. In another preferred embodiment, the cross-linking is performed in the presence of a linker having two or more nucleophilic groups, and the linker is thereby incorporated into the biomaterial. Preferred linkers include a peptide with an amino acid sequence that is 80%, preferably 90%, or more preferably 100% identical to the sequence GCNNRGDNNCG (SEQ ID NO: 75). Other preferred linkers include those having an amino acid sequence or moiety that provides targeting to cells, tissues, organs, organ systems, or sites within a mammal. In one preferred embodiment, the cross-linking step and/or the formation of the precursor components of the biomaterial occurs within the body of a mammal, such as a human. In another preferred embodiment, the cross-linking occurs through free radical polymerization or conjugate addition reactions at or near a site within the body of a mammal. Preferably, the cross-linking occurs through a self-selective reaction between a thiol or an amine and a conjugated unsaturated group. In another preferred embodiment, the cross-linking forms a hydrogel, a colloidal material, a microsphere, or nanosphere that can be delivered to a mammal, such as a human. In yet another preferred embodiment, the pharmaceutically active compound or a derivative thereof is released from the biomaterial and delivered to a site within the body. Preferably, the half-life the ester or amide bond onto the pharmaceutically active moiety is between 1 hour and 1 year at the site within the body. Preferably, the half-life is between 1 hour and 1 year at pH 7.4 and 37° C. in an aqueous solution. The conjugated unsaturated groups of this aspect may have the same embodiments as listed for the conjugated unsaturated groups of any of the previous aspects.

In a fourteenth aspect, the invention features a biomaterial having a pharmaceutically active moiety. The biomaterial includes an ester or amide bond onto the pharmaceutically active moiety, and this bond has a half-life of between 1 hour and 1 year in an aqueous solution at pH 7.4 and 37° C. Preferably, the half-life of the ester or amide bond onto the pharmaceutically active moiety for this biomaterial, the biomaterial of the sixth aspect of the invention, and the biomaterials formed using the methods of the invention is between 1 day and 9 months, more preferably between 2 days and 6 months, and most preferably between 4 days and 3 weeks.

In preferred embodiments of the thirteenth and fourteenth aspects, the pharmaceutically active moiety has any of the preferred embodiments of the pharmaceutically active moiety of the previous aspects.

In a fifteenth aspect, the invention provides a method of treating or preventing a disease, disorder, or infection by administering to a mammal, such as a human, a compound having the formula:

D-Y—C(O)—(CH$_2$)$_n$—SH,

D-Y—C(O)—(CH$_2$)$_n$—NH$_2$,

D-Y—C(O)—(CH$_2$)$_n$—S—(CH$_2$)$_2$—COX—P,

D-Y—C(O)—(CH$_2$)$_n$—NH—(CH$_2$)$_2$—COX—P,

D-Y—C(O)—(CH$_2$)$_n$—NH—U—P,

D-Y—C(O)—(CH$_2$)$_n$—S—U—P,

D-Y—C(O)—CH=CH$_2$,

D-Y—C(O)—CH—CH$_2$—P,

D-Y—C(O)—(CH$_2$)$_2$—S-L-SH,

D-Y—C(O)—(CH$_2$)$_2$—NH-L-SH,

D-Y—C(O)—(CH$_2$)$_2$—S-L-NH$_2$,

D-Y—C(O)—(CH$_2$)$_2$—NH-L-NH$_2$.

D-Y—C(O)—(CH$_2$)$_2$—S-L-S—CH$_2$—CH$_2$—CO—X—P,

D-Y—C(O)—(CH$_2$)$_2$—S-L-S—U—P,

D-Y—C(O)—(CH$_2$)$_2$—NH-L-S—CH$_2$—CH$_2$—CO—X—P,

D-Y—C(O)—(CH$_2$)$_2$—NH-L-S—U—P,

D-Y—C(O)—(CH$_2$)$_2$—S-L-NH—CH$_2$—CH$_2$—CO—X—P,

D-Y—C(O)—(CH$_2$)$_2$—S-L-NH—U—P,

D-Y—C(O)—(CH$_2$)$_2$—NH-L-NH—CH$_2$—CH$_2$—CO—X—P,

D-Y—C(O)—(CH$_2$)$_2$—NH-L-NH—U—P, or Z-P, wherein D is a pharmaceutically active moiety; Y is O, NH, or N; L is a linear or branched linker; X is O or N; Z is a pharmaceutically active moiety in which a nucleophilic amine or thiol has been incorporated; P is a water-soluble polymer or a water-swellable polymer having one or more conjugated unsaturated groups; and U is the product of the addition of a nucleophile to an electrophilic group that is attached to the polymer. The half-life of the ester or amide bond onto the pharmaceutically is between 1 hour and 1 year in an aqueous solution at pH 7.4 and 37° C.

In a sixteenth aspect, the invention features a method of treating or preventing a disease, disorder, or infection in a mammal. This method includes administering to the mammal a biomaterial having a pharmaceutically active moiety. This biomaterial is formed from the cross-linking of one or more of the following precursor components:

D-Y—C(O)—(CH$_2$)$_n$—S—(CH$_2$)$_2$—COX—P,

D-Y—C(O)—(CH$_2$)$_n$—NH—(CH$_2$)$_2$—COX—P,

D-Y—C(O)—(CH$_2$)$_n$—NH—U—P,

D-Y—C(O)—(CH$_2$)$_n$—S—U—P,

D-Y—C(O)—CH—CH$_2$—P,

D-Y—C(O)—(CH$_2$)$_2$—S-L-S—CH$_2$—CH$_2$—CO—X—P,

D-Y—C(O)—(CH$_2$)$_2$—S-L-S—U—P,

D-Y—C(O)—(CH$_2$)$_2$—NH-L-S—CH$_2$—CH$_2$—CO—X—P,

D-Y—C(O)—(CH$_2$)$_2$—NH-L-S—U—P,

D-Y—C(O)—(CH$_2$)$_2$—S-L-NH—CH$_2$—CH$_2$—CO—X—P,

D-Y—C(O)—(CH$_2$)$_2$—S-L-NH—U—P,

D-Y—C(O)—(CH$_2$)$_2$—NH-L-NH—CH$_2$—CH$_2$—CO—X—P,

D-Y—C(O)—(CH$_2$)$_2$—NH-L-NH—U—P, or

Z-P, wherein D is a pharmaceutically active moiety; Y is O, NH, or N; L is a linear or branched linker; X is O or N; Z is a pharmaceutically active moiety in which a nucleophilic amine or thiol has been incorporated; P is a water-soluble polymer or a water-swellable polymer having one or more conjugated unsaturated groups; and U is the product of the addition of a nucleophile to an electrophilic group that is attached to the polymer. The half-life of the ester or amide bond onto the pharmaceutically is between 1 hour and 1 year in an aqueous solution at pH 7.4 and 37° C.

In a seventeenth aspect, the invention provides a method of treating or preventing a disease, disorder, or infection in a mammal. This method includes (a) attaching a pharmaceutically active compound to a linker molecule, (b) removing any thiol- or amine-protecting groups in the linker, (c) coupling a thiol amine, or alkene group in the linker to a water soluble polymer or a water swellable polymer having two or more conjugated unsaturated groups by a conjugate addition reaction, and (d) cross-linking the uncoupled unsaturated groups in the polymer at a site within a mammal. In one embodiment of this aspect, one or more of steps (a) through (c) are also performed at a site within a mammal.

In an eighteenth aspect, the invention features a method of treating or preventing a disease, disorder, or infection in a mammal by administering to the mammal a biomaterial having a pharmaceutically active moiety. The biomaterial includes an ester or amide bond onto the pharmaceutically active moiety, and this bond has a half-life of between 1 hour and 1 year in an aqueous solution at pH 7.4 and 37° C.

In a nineteenth aspect, the invention features a method for delivering a pharmaceutically active compound to a cell, tissue, organ, organ system, or body of a mammal. This method includes contacting the cell, tissue, organ, organ system or body with a biomaterial having an ester or amide bond onto a pharmaceutically active moiety. The bond has a half-life of between 1 hour and 1 year in an aqueous solution at pH 7.4 and 37° C., and cleavage of the bond results in the release of a pharmaceutically active compound having the pharmaceutically active moiety.

In a twentieth aspect, the invention features a method for delivering a pharmaceutically active compound to a cell, tissue, organ, organ system, or body of a mammal. This method includes administering to the mammal a biomaterial having a pharmaceutically active moiety. The biomaterial is formed from the cross-linking of a precursor component in the presence of a linker having two or more nucleophilic groups. The precursor component includes a pharmaceutically active moiety coupled to a polymer having two or more conjugated unsaturated groups, and the linker provides targeting to a cell, tissue, organ, organ system, or site within the mammal. A pharmaceutically active compound having the pharmaceutically active moiety is released from the biomaterial at or near the cell, tissue, organ, organ system, or body of the mammal. In one preferred embodiment of this aspect, the biomaterial has an ester or amide bond onto the pharmaceutically active moiety, and the bond has a half-life of between 1 hour and 1 year in an aqueous solution at pH 7.4 and 37° C.

In a twenty-first aspect, the invention provides a method of preventing adhesions, thrombosis, or restenosis in a mammal. This method includes contacting a site in the mammal with a precursor component and cross-linking the precursor component at the site. The precursor component has the formula:

D-Y—C(O)—(CH$_2$)$_n$—S—(CH$_2$)$_2$—COX—P,

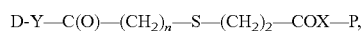

D-Y—C(O)—(CH$_2$)$_n$—NH—(CH$_2$)$_2$—COX—P,

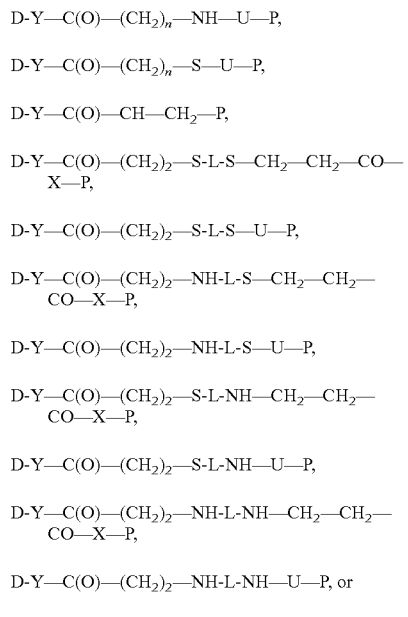

wherein D is a pharmaceutically active moiety; Y is O, NH, or N; L is a linear or branched linker; X is O or N; Z is a pharmaceutically active moiety in which a nucleophilic amine or thiol has been incorporated; P is a water-soluble polymer or a water-swellable polymer having one or more conjugated unsaturated groups; and U is the product of the addition of a nucleophile to an electrophilic group that is attached to the polymer. The half-life of the ester or amide bond onto the pharmaceutically is between 1 hour and 1 year in an aqueous solution at pH 7.4 and 37° C.

In a twenty-second aspect, the invention provides a method of preventing adhesions, thrombosis, or restenosis in a mammal. This method includes contacting a site within the mammal with a biomaterial having an ester or amide bond onto a pharmaceutically active moiety. The bond has a half-life of between 1 hour and 1 year in an aqueous solution at pH 7.4 and 37° C. and cleavage of the bond results in the release of a pharmaceutically active compound having the pharmaceutically active moiety.

In one preferred embodiment of the fifteenth through twenty-second aspects, the compound, precursor component, or biomaterial is administered orally, intravenously, intramuscularly, subcutaneously, parenterally or by any other route sufficient to provide an adequate dose for the prevention or treatment of a disease, disorder, or infection. In another preferred embodiment of these aspects, the ester or amide bond onto the pharmaceutically active moiety has a half-life of between 1 day and 9 months in an aqueous solution at pH 7.4 and 37° C. More preferably, the half-life is between 2 days and 6 months, and most preferably it is between 4 days and 3 weeks in an aqueous solution at pH 7.4 and 37° C. One disease that may be treated or prevented using the methods of these aspects is cancer. Preferably, the mammal is a human. The linker of these aspects may have the same embodiments as listed for the linker of the fourth through sixth aspects. The pharmaceutically active moiety or the conjugated unsaturated groups of these aspects may have the corresponding preferred embodiments listed for any of the previous aspects.

The aforementioned new aspects of the invention may include self-selective conjugate addition reactions between a strong nucleophile and a conjugated unsaturated group for cross-linking of precursor components to form a biomaterial, as we described in the U.S. patent application U.S. Ser. No. 09/496,231 which is incorporated herein by reference. For example, the novel precursor components of the present invention, which have a covalently bound pharmaceutically active moiety, may be cross-linked in the presence of a polymer having two or more nucleophilic groups to form a copolymer in methods that include self-selective conjugate addition reactions. In addition, the methods of the present invention may utilize a self-selective conjugate addition reaction for the coupling of a thiol or amine group, linked to or incorporated into a pharmaceutically active compound, to a conjugated unsaturated group on a polymer for the production of novel compounds.

We now describe the polymeric biomaterials that we previously developed, which are unique in their use of addition reactions between a strong nucleophile and a conjugated unsaturation for polymerizing or cross-linking two or more components in a manner that can be accomplished in the presence of sensitive biological materials. Applications of the process include formation of biomaterials in the presence of drugs, including proteins and DNA, formation of biomaterials in the presence of cells and cell aggregates, and also formation of biomaterials in vivo either within the body or upon the surface of the body. It is possible to form these biomaterials in the presence of sensitive biological materials because of the high self-selectivity of the addition reactions between strong nucleophiles and conjugated unsaturations, that are employed. The strong nucleophile of particular interest in the method described herein is the thiol.

In the formation of the biomaterial in the presence of the sensitive biological materials, two or more liquid components can be mixed together and react to form either an elastic solid, a viscoelastic solid (like a typical solid gel, for example, a gel like gelatin), a viscoelastic liquid (like a typical gel that can be induced to flow, for example, a gel like petroleum jelly), a viscoelastic liquid that is formed of gel microparticles (such as a Carbopol™ gel) or even a viscous liquid of a considerably higher viscosity than either of the two precursor components that are mixed together. The chemical conversion from the precursors to the final material is so selective that it can be carried out in the presence of the sensitive biological material, including the case when the biological material is the body itself.

A novel family of potentially highly biomimetic synthetic polymers has been developed. These polymers can: (i) be converted from liquid precursors to polymeric linear or cross-linked biomaterials either in the laboratory or in situ at a site of implantation; (ii) be hydrogels or more substantially non-swelling materials; (iii) present bioactive molecules that serve as adhesion sites, to provide traction for cell invasion; (iv) present bioactive molecules that serve as protease substrate sites, to make the material degrade in response to enzymes, such as collagenase or plasmin, which are produced by cells during cell migration; (v) present growth factor binding sites, to make the material interact with growth factors in a biomimetic manner, by binding them and then releasing them on cellular demand; and (vi) provide for the delivery of protein drugs by hydrolysis or enzymatic degradation of groups contained within the backbone of the polymers that form the gel.

Accordingly, in a twenty-third aspect the invention features a method for making a biomaterial, involving combining two or more precursor components of the biomaterial under conditions that allow polymerization of the two components, where polymerization occurs through self selective reaction between a strong nucleophile and a conjugated unsaturated bond or a conjugated unsaturated group, by nucleophilic addition. The functionality of each component is at least two, and the biomaterial does not comprise unprocessed albumin. In addition, the conjugated unsaturated bond or group is not a maleimide or a vinyl sulfone.

In one embodiment of the twenty-third aspect of the invention, the components are selected from the group consisting of oligomers, polymers, biosynthetic proteins or peptides, naturally occurring peptides or proteins, processed naturally occurring peptides or proteins, and polysaccharides. The polymer may be poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly(propylene oxide) block copolymers. The peptide may comprise an adhesion site, growth factor binding site, or protease binding site.

In another embodiment, the components are functionalized to comprise a strong nucleophile or a conjugated unsaturated group or a conjugated unsaturated bond. Preferably the strong nucleophile is a thiol or a group containing a thiol. Preferably the conjugated unsaturated group is an acrylate, an acrylamide, a quinone, or a vinylpyridinium, for example, 2- or 4-vinylpyridinium. In another embodiment, one component has a functionality of at least three.

In yet other embodiments of the twenty-third aspect of the invention, the method further comprises combining the precursor components with a molecule that comprises an adhesion site, a growth factor binding site, or a heparin binding site and also comprises either a strong nucleophile or a conjugated unsaturated bond or a conjugated unsaturated group. Preferably the strong nucleophile is a thiol or the conjugated unsaturated bond or conjugated unsaturated group is an acrylate, an acrylamide, a quinone, or a vinyl pyridinium.

In still other embodiments of the twenty-third aspect of the invention, the biomaterial is a hydrogel. The biomaterial may also be degradable. The biomaterial may be made in the presence of sensitive biological molecules, or in the presence of cells or tissues. The biomaterial may also be made within or upon the body of an animal.

In still further embodiments of the twenty-third aspect of the invention, the method further comprises combining the precursor components with an accelerator prior to polymerization. The method may also further comprise mixing the precursor components with a component that comprises at least one conjugated unsaturated bond or conjugated unsaturated group and at least one amine reactive group. An additional component may also be applied to the cell or tissue surface site of polymerization, the additional component comprising at least one conjugated unsaturated bond or conjugated unsaturated group and at least one amine reactive group.

In a twenty-fourth aspect, the invention features a biomaterial formed by combining two or more precursor components of a biomaterial under conditions that allow polymerization of the two components, where polymerization occurs through self selective reaction between a strong nucleophile and a conjugated unsaturated bond or a conjugated unsaturated group, by nucleophilic addition. The functionality of each component is at least two, the biomaterial does not comprise unprocessed albumin, and the conjugated unsaturated bond or conjugated unsaturated group is not a maleimide or a vinyl sulfone.

In one embodiment of the twenty-fourth aspect of the invention, the components are selected from the group consisting of oligomers, polymers, biosynthetic proteins or peptides, naturally occurring peptides or proteins, processed naturally occurring peptides or proteins, and polysaccharides. The polymer may be poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly (propylene oxide) block copolymers. The peptide may comprise an adhesion site, growth factor binding site, or protease binding site.

In another embodiment of the twenty-fourth aspect of the invention, the components are functionalized to comprise a strong nucleophile or a conjugated unsaturated group or a conjugated unsaturated bond. Preferably the strong nucleophile is a thiol or a group containing a thiol. Preferably the conjugated unsaturated group is an acrylate, an acrylamide, a quinone, or a vinylpyridinium, for example, 2- or 4-vinylpyridinium. In another embodiment, one component has a functionality of at least three.

In yet other embodiments of the twenty-fourth of the invention, the method further comprises combining the precursor components with a molecule that comprises an adhesion site, a growth factor binding site, or a heparin binding site and also comprises either a strong nucleophile or a conjugated unsaturated bond or a conjugated unsaturated group. Preferably the strong nucleophile is a thiol or the conjugated unsaturated bond or conjugated unsaturated group is an acrylate, an acrylamide, a quinone, or a vinyl pyridinium.

In still other embodiments of the twenty-fourth aspect of the invention, the biomaterial is a hydrogel. The biomaterial may also be degradable. The biomaterial may be made in the presence of sensitive biological molecules, or in the presence of cells or tissues. The biomaterial may also be made within or upon the body of an animal.

In still further embodiments of the twenty-fourth aspect of the invention, the method further comprises combining the precursor components with an accelerator prior to polymerization. The method may also further comprise mixing the precursor components with a component that comprises at least one conjugated unsaturated bond or conjugated unsaturated group and at least one amine reactive group. An additional component may also be applied to the cell or tissue surface site of polymerization, the additional component comprising at least one conjugated unsaturated bond or conjugated unsaturated group and at least one amine reactive group.

In a twenty-fifth aspect, the invention features a method for delivering a therapeutic substance to a cell, tissue, organ, organ system, or body of an animal said method involving contacting the cell, tissue, organ, organ system or body with the biomaterial of the twenty-fourth aspect of the invention, wherein the biomaterial contains a therapeutic substance, whereby the therapeutic substance is delivered to the cell, tissue, organ, organ system, or body of an animal.

In one embodiment, the therapeutic substance is selected from the group consisting of proteins, naturally occurring or synthetic organic molecules, nucleic acid molecules, for example DNA or RNA, and a viral particle. In another embodiment, the therapeutic substance is a prodrug. In still another embodiment, the nucleic acid molecule is an antisense nucleic acid molecule.

In a twenty-sixth aspect, the invention features a method of regenerating a tissue, involving introducing a scaffold to a site, under conditions which permit cell ingrowth. The scaffold may comprising the biomaterial of the twenty-fourth aspect of the invention.

In embodiments of the twenty-sixth aspect of the invention, the scaffold has been pre-seeded with cells. The tissue may be selected from the group consisting of bone, skin, nerve, blood vessel, and cartilage.

In a twenty-seventh aspect, the invention features a method of preventing adhesions, thrombosis, or restenosis, involving contacting a site with the biomaterial precursor components of the twenty-fourth aspect of the invention; and polymerizing the components at the site.

In a twenty-eighth aspect, the invention features a method of sealing a fluid or gas flow, said method comprising the steps of contacting a site within the body of an animal with the biomaterial precursor components of the twenty-fourth aspect of the invention, which may further comprise a component that includes at least one conjugated unsaturated bond or conjugated unsaturated group and a least one amine reactive group; and polymerizing the components at the site.

In preferred embodiments of the twenty-eighth aspect of the invention, the site is a lung, blood vessel, skin, dura barrier, or intestine.

In a twenty-ninth aspect, the invention features a method of encapsulating a cell or tissue, involving combining the precursor components of a biomaterial with a cell or tissue; and polymerizing the components, where polymerization occurs through self selected reaction between a strong nucleophile and a conjugated unsaturated bond or a conjugate unsaturated group, and where the cell or tissue is encapsulated by the polymerized biomaterial.

In an thirtieth aspect, the invention features a method for making a biomaterial, involving combining two or more precursor components of the biomaterial under conditions that allow polymerization of the two components, where the polymerization occurs through self selective reaction between an amine and a conjugated unsaturated bond or a conjugated unsaturated group, by nucleophilic addition, wherein the functionality of each component is at least two, and wherein the biomaterial does not comprise unprocessed albumin, and the unsaturated bond or group is not a maleimide or a vinyl sulfone.

In a thirty-first aspect, the invention features a biomaterial, formed by combining two or more precursor components of the biomaterial under conditions that allow polymerization of the two components, where the polymerization occurs through self selective reaction between an amine and a conjugated unsaturated bond or a conjugated unsaturated group, by nucleophilic addition, wherein the functionality of each component is at least two, and wherein the biomaterial does not comprise unprocessed albumin, and the unsaturated bond or group is not a maleimide or a vinyl sulfone.

By "biomaterial" is meant a material which is intended for contact with the body, either upon the surface of it or implanted within it. Preferably, the biomaterial is formed by a conjugate addition reaction between a strong nucleophile and a conjugated unsaturation.

As used herein, the words "polymerization" and "cross-linking" are used to indicate a linking of multiple precursor component molecules to result in a substantial increase in molecular weight. "Cross-linking" further indicates branching, typically to yield a polymer network.

By "self-selective" is meant that a first precursor component of the reaction reacts much faster with a second precursor component of the reaction than with other compounds present in the mixture at the site of the reaction, and the second precursor component reacts much faster with the first precursor component than with other compounds present in the mixture at the site of the reaction. Preferably, the reaction between the first and second precursor components is at least 2 times, more preferably at least 10 times, and most preferably at least 50 times faster than the next fastest reaction between the first or second precursor component and another compound present in the mixture. The mixture may contain other biological materials, for example, drugs, peptides, proteins, DNA, cells, cell aggregates, and tissues. As used herein, a strong nucleophile preferentially binds to a conjugated unsaturation, rather than to other biological compounds, and a conjugated unsaturated group preferentially binds to a strong nucleophile rather than to other biological compounds.

When the highest degree of self-selectivity is desired in the methods of the invention, a thiol is the nucleophile of choice. When the highest level of self-selectivity is not required in the methods of the invention, an amine may be used as the strong nucleophile. Conditions utilized to complete the self selective reaction of the present invention can be altered to increase the degree of self selectivity, as provided herein. For example, if an amine is used as the strong nucleophile in the formation of a biomaterial by selection of an amine with a low pK, and the final precursor solution to be polymerized is formulated such that the pH is near the pK, the reaction of the unsaturation with the provided amine is favored and thus self selectivity is achieved.

By "strong nucleophile" is meant a molecule which is capable of donating an electron pair to an electrophile in a polar-bond forming reaction. Preferably the strong nucleophile is more nucleophilic than $H_2O$ at physiologic pH. Examples of strong nucleophiles are thiols and amines.

A thiol is the preferred strong nucleophile to be used in the present invention, as it exhibits high self-selectivity. Very few sterically accessible thiols are present in proteins that are found outside cells. Amines may also be useful and self-selective especially when the biomaterial-forming reaction is conducted in the presence of sensitive biological molecules that do not bear amines, for example, many drugs.

By "conjugated unsaturated bond" is meant the alternation of carbon-carbon, carbon-heteroatom or heteroatom-heteroatom multiple bonds with single bonds, or the linking of a functional group to a macromolecule, such as a synthetic polymer or a protein. Such bonds can undergo addition reactions.

By "conjugated unsaturated group" is meant a molecule or a region of a molecule, containing an alternation of carbon-carbon, carbon-heteroatom or heteroatom-heteroatom multiple bonds with single bonds, which has a multiple bond which can undergo addition reactions. Examples of conjugated unsaturated groups include, but are not limited to acrylates, acrylamides, quinones, and vinylpyridiniums, for example, 2- or 4-vinylpyridinium.

By "substantially pure peptide," "substantially pure polypeptide" or "substantially pure protein" is meant a polypeptide that has been separated from the components that naturally accompany it. As used herein the terms peptide, polypeptide, and protein are used interchangeably. Typically, the polypeptide is substantially pure when it is at least 60%, by weight, free from the proteins and naturally-occurring organic molecules with which it is naturally associated. Preferably, the polypeptide is at least 75%, more preferably, at least 90%, and most preferably, at least 99%, by weight, pure. A substantially pure polypeptide of interest may be obtained, for example, by extraction from a natural source (e.g., a cell, cell aggregate, or tissue) by expression of a recombinant nucleic acid encoding the desired polypeptide, or by chemically synthesizing the protein. Purity can be assayed by any appropriate method, for example, by column chromatography, polyacrylamide gel electrophoresis, agarose gel electrophoresis, optical density, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "purified nucleic acid" is meant a nucleic acid molecule that is free of the genes which, in the naturally-occurring genome of the organism from which the nucleic acid of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes recombinant DNA which is part of a hybrid gene encoding additional polypeptide sequence.

By "functionalize" is meant to modify in a manner that results in the attachment of a functional group or moiety. For example, a molecule may be functionalized by the introduction of a molecule which makes the molecule a strong nucleophile or a conjugated unsaturation. Preferably a molecule, for example PEG, is functionalized to become a thiol, amine, acrylate, or quinone.

Proteins in particular may also be effectively functionalized by partial or complete reduction of disulfide bonds to create free thiols.

By "functionality" is meant the number of reactive sites on a molecule. As used herein, the functionality of a strong nucleophile and a conjugated unsaturation will each be at least two. Mixing two components, for example, a strong nucleophile and a conjugated unsaturation, with functionalities of two each will result in a linear polymeric biomaterial, and the mixing to two components with functionalities of at least two each, one of the components having a functionality of more than two, will result in a cross-linked biomaterial.

By "adhesion site" is meant a peptide sequence to which a molecule, for example, an adhesion-promoting receptor on the surface of a cell, binds. Examples of adhesions sites include, but are not limited to, the RGD sequence from fibronectin, and the YIGSR sequence from laminin. Preferably adhesion sites are incorporated into the biomaterial of the present invention.

By "growth factor binding site" is meant a peptide sequence to which a growth factor, or a molecule(s) which binds a growth factor binds. For example, the growth factor binding site may include a heparin binding site. This site will bind heparin, which will in turn, bind heparin-binding growth factors, for example, bFGF, VEGF, BMP, or TGFβ.

By "protease binding site" is meant a peptide sequence which is a substrate for an enzyme.

By "antisense nucleic acid" is meant a nucleic acid sequence, regardless of length, that is complementary to the coding strand gene encoding a protein of interest. Preferably, the antisense nucleic acid is capable of decreasing the biological activity of said protein of interest when present in a cell. Preferably, the decrease is at least 10%, relative to a control, more preferably, 25%, and most preferably, 100%.

By "biological activity" is meant functional events mediated by a protein of interest. In some embodiments, this includes events assayed by measuring the interactions of a polypeptide with another polypeptide. It also includes assaying the effect which the protein of interest has on cell growth, differentiation, death, migration, adhesion, interactions with other proteins, enzymatic activity, protein phosphorylation or dephosphorylation, transcription, or translation.

By "sensitive biological molecule" is meant a molecule that is found in a cell, or in a body, or which can be used as a therapeutic for a cell or a body, and which may react with other molecules in its presence. Examples of sensitive biological molecules include, but are not limited to, peptides, proteins, nucleic acids, and drugs. In the present invention biomaterials can be made in the presence of sensitive biological materials, without adversely affecting the sensitive biological materials.

As used herein, by "regenerate" is meant to grow back a portion, or all of, a tissue. For example, the present invention features methods of regenerating bone following trauma, tumor removal, or spinal fusion, or for regenerating skin to aid in the healing of diabetic foot ulcers, pressure sores, and venous insufficiency. Other tissues which may be regenerated include, but are not limited to, nerve, blood vessel, and cartilage tissue.

By "cell transplantation" is meant transplanting a cell, cell aggregate, or tissue into a subject. The biomaterial of the present invention can be used to isolate transplanted cells, cell aggregates, or tissues in the subject from the subject's defense system, while allowing the selective transport of molecules required for normal cell function.

By "pharmaceutically active moiety" is meant a species that differs from a therapeutically active compound in that it does not contain a reactive group, such as an alcohol or amine group, that is present in the compound. The pharmaceutically active moiety is denoted by D, and the therapeutically active compound is designated D-OH, D-$NH_2$, or D-NH.

By "water-soluble polymer" is meant a compound formed from the cross-linking of two or more monomers, whereby the compound is capable of being dissolved in water.

By "water swellable polymer" is meant a compound formed from the cross-linking of two or more monomers, whereby the compound does not dissolve in water. The interaction between the water and the polymer causes the polymer to increase in volume.

By "copolymer" is meant a polymer that is formed from two or more monomers, wherein at least two of the monomers have a different chemical formula or structure.

By "linker" is meant a compound or a moiety within a compound that is capable of coupling a pharmaceutically active moiety to polymer through a series of covalent bonds. The linker can either bind an atom that is present in the pharmaceutically active moiety or it can bind an atom that is coupled to the pharmaceutically active moiety through a series of covalent bonds. Another atom on the linker can either react with a conjugated unsaturated group that is attached to a polymer or it can bind to a group that is capable of reacting with a conjugated unsaturated group.

By "rate of release" is meant the rate of production due to the hydrolysis of a bond in a biomaterial or a component of a biomaterial. If the ester or amide bond onto the pharmaceutically active moiety, denoted D, is hydrolyzed, the original pharmaceutically active compound that was used in the formation of the compound or biomaterial is released. If another bond, such as a bond within the linker or an ester bond onto the polymer is hydrolyzed, a modified version of the original pharmaceutically active compound is released. The modified compound can be represented as D-$O_2$C-Z, D-NH—C(O)-Z, or D-N—C(O)-Z wherein Z comprises the portion of the component or biomaterial between the hydrolyzed bond and the D-$O_2$C, D-NH—C(O), or D-N—C(O) group.

By "pharmaceutically active compound derived from D" is meant a therapeutically active compound that comprises the pharmaceutically active moiety D. The compound may be the same as the original pharmaceutically active compound; denoted D-OH, D-$NH_2$, or D-NH; used in the formation of the component or biomaterial. Alternatively, the compound may be represented as D-$O_2$C-Z, D-NH—C(O)-Z, or D-N—C (O)-Z as described above; in this case, the compound has the group —$O_2$—C-Z instead of the hydroxyl group or the NH—C(O)-Z or N—C(O)-Z group instead of the amine group ($NH_2$ or NH) that was modified during the formation of the component or biomaterial.

By "pharmaceutically active compound or derivative thereof" is meant a therapeutically active compound, denoted D-OH, D-$NH_2$, or D-NH, or a derivative of this compound in which the alcohol or amine group is modified such that the derivative is represented by D-$O_2$C-Z, D-NH—C(O)-Z, or D-N—C(O)-Z, as noted above.

By "coupled to" is meant reacted with or attached to, possibly through a series of covalent bonds. For example, "a pharmaceutically active moiety coupled to a polymer" refers to a moiety that is present in the same molecule as the polymer and that is either directly bound to the polymer or is bound to another group, such as a linker, that is bound to the polymer. A pharmaceutically active moiety is considered to be coupled to only one conjugated unsaturated group on a polymer. Thus, if a pharmaceutically active moiety or a group attached to the pharmaceutically active moiety is reacted with a conjugated unsaturated group on a polymer, then the moiety is said to be coupled to that conjugated unsaturated group. The remaining conjugated unsaturated group(s) attached to the polymer that were not reacted with the compound having the pharmaceutically active moiety are referred to as "not coupled to the pharmaceutically active moiety."

By "derivative" of an organic molecule is meant a compound having a portion of the organic molecule and having the same therapeutic activity as the organic molecule. The derivative may have one more functional groups that are not present in the pharmaceutically active organic molecule. Additionally, the derivative might not have one or more functional groups that are present in the pharmaceutically active organic molecule.

By "pharmaceutically active moiety is derived from" is meant a moiety in a pharmaceutically active compound that can be attached to another compound. For example, a reactive group—such as an alcohol, primary amine, or secondary amine—on a pharmaceutically active compound can react with a compound having a carboxylic acid, forming a product that includes the pharmaceutically active moiety. In this case, the moiety does not contain a hydrogen that is present in the pharmaceutically active compound, and the product contains an ester or amide bond onto the pharmaceutically active moiety.

By "nucleophilic substitution reaction" is meant a reaction between a nucleophile and an electrophile in which a covalent bond is formed between the nucleophile and the electrophile and a bond is broken between the electrophile and a leaving group. Thus, a leaving group that had been bound to the electrophile is replaced by the nucleophile.

By "free radical polymerization" is meant the cross-linking of monomers that is initiated by a radical. The radical reacts with a monomer, producing a radical that can react with another monomer.

By "conjugate addition reaction" is meant a reaction between a nucleophile and a conjugated unsaturated group or conjugated unsaturated bond. For example, a nucleophile can react with a α, β unsaturated aldehyde or ketone, resulting in the formation of a covalent bond between the nucleophile and the β carbon and a bond between a hydrogen atom and the α carbon. In this reaction, a bond between the α and β carbons is also converted from a double to a single bond. Additional examples are listed in the Detailed Description section.

By "at or near a site within the body" is meant located close to a site within the body such that the released pharmaceutically active compound is localized to the desired area.

By "colloidal material" is meant a copolymer of dimension greater than 5 nm and smaller than 1 µm.

By "microsphere" is meant a biomaterial having a spherical shape with a diameter between 1 and 1000 µm.

By "nanosphere" is meant a biomaterial having a spherical shape with a diameter between 1 and 1000 nm.

By "base that is modified to contain a thiol" is meant a base that has a thiol or a group having a sulfur. For example, a 6-cholorpurine derivative can be reacted with $H_2S$ to form an adenosine having a sulfur instead of an amine group.

By "modified naturally occurring peptides or proteins" is meant naturally occurring peptides or proteins that have been reacted with a group having a thiol or amine such that the product is capable of reacting with a conjugated unsaturated group or bond through a conjugate addition reaction.

By "purification step" is meant a step that increases the purity of a product. The product can be separated from some of the other components of a mixture such as starting materials, accelerators, side-products, and solvents. Products can be purified base on their characteristics—such as size, shape, charge, hydrophobicity, solubility, or boiling point—using standard techniques.

By "condensing agent" is meant a compound that accelerates the reaction between an alcohol or amine and a carboxylic acid. The condensing agent reacts with the carboxylic acid such that the hydroxyl group of the carboxylic acid is converted into a better leaving group for the nucleophilic substitution reaction between this activated carboxylic acid and the alcohol or amine. Condensing agents are well known in the art of organic synthesis.

By "treating or preventing a disease, disorder, or infection" is meant administering to a mammal a biomaterial, precursor component of a biomaterial, or compound that has a covalently bound pharmaceutically active moiety. In a preferred embodiment, the administered precursor components cross-link within the body to form a biomaterial. A therapeutically active compound is released from the biomaterial due to hydrolysis of a bond between the pharmaceutically active moiety and the polymer, such as the ester or amide bond onto the pharmaceutically active moiety. This compound is capable of reducing or delaying the onset of symptoms or removing or preventing the cause of a disease, disorder, or infection.

It is not intended that the administration of the biomaterials, precursor components, or compounds of the invention be limited to a particular mode of administration, dosage, or frequency of dosing; the present mode contemplates all modes of administration, including oral, intravenous, intramuscular, subcutaneous, parenteral, or any other route sufficient to provide a dose adequate to prevent or treat a disease, disorder, or infection. One or more of the biomaterials, precursor components, or compounds may be administered to a mammal in a single dose or multiple doses, possibly in the presence of pharmaceutical stabilizing compounds. When multiple doses are administered, the doses can be separated from one another by, for example, one week to one month. It is to be understood that for any particular subject, specific dosage regimes should be adjusted over time according to the individual need and the professional judgement of the person administering or supervising the administration of the compositions.

DETAILED DESCRIPTION

Figure 1:
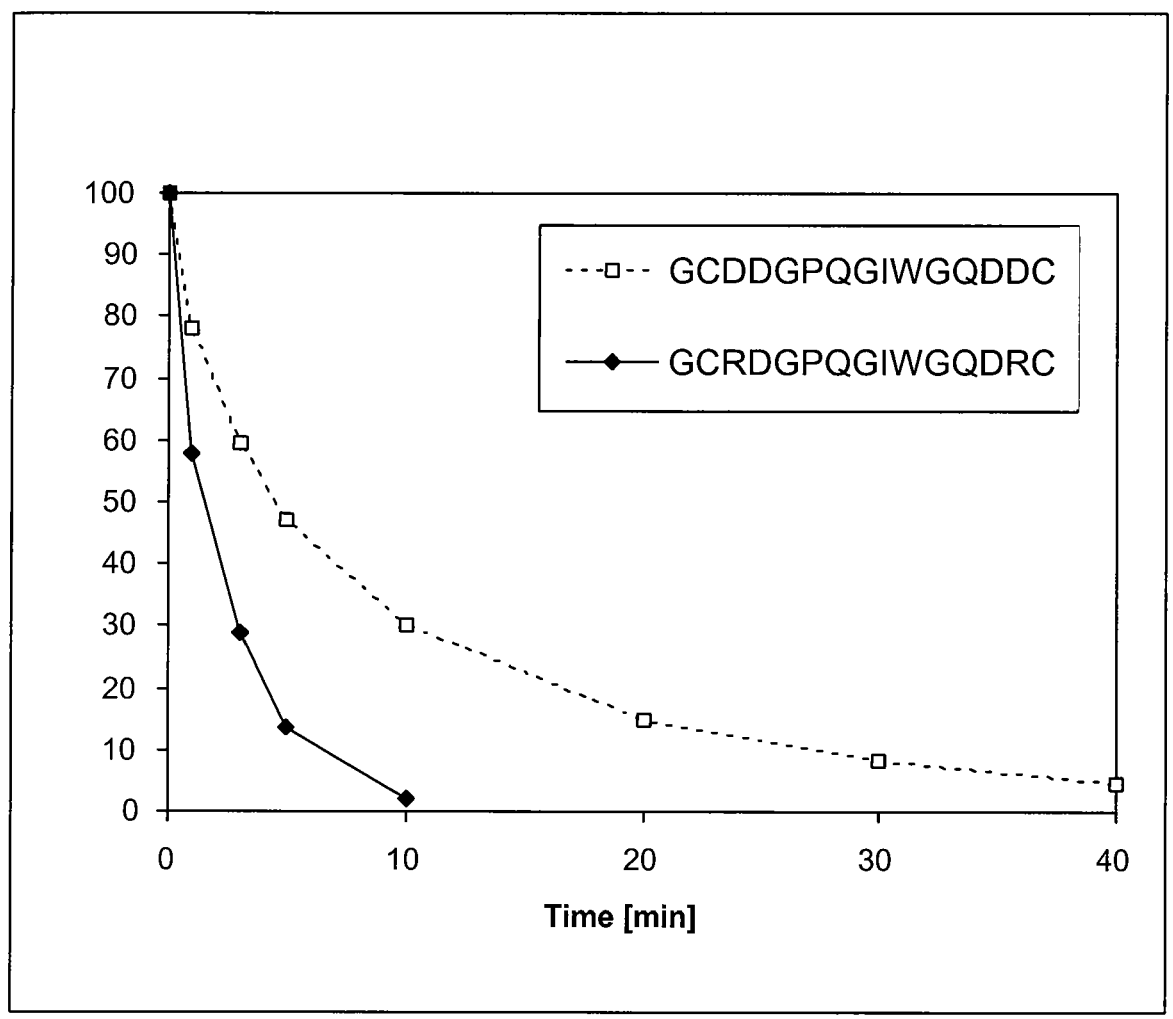
FIG. 1 is a graph of the effect of changing the amino acid residues adjacent to cysteine on the rate of conjugate addition on acrylates (PEG-acrylate).

I. In vivo Synthesis or Application of Biomaterials

The Chemical Reaction System Used for Biomaterial Formation

A novel chemical reaction scheme has been developed by which to polymerize or cross-link (the words are used as synonyms herein) two or more precursor components of a biomaterial in situ or in the presence of sensitive biological materials in a very self-selective manner. Commonly, two precursor components are mixed together. These two precursor components are self-selective in their reaction rates (i.e., a first precursor component reacts much faster with a second precursor component than with other components in the sensitive biological material and the second precursor component reacts much quicker with the first precursor component than with other components in the sensitive biological material). When both of these precursor components have a functionality of at least two, and when one of them has a functionality greater than two, the system will self-selectively react to form a cross-linked biomaterial. The word "functionality" is used here in the sense used in polymer science (i.e., the number of reactive sites). Thus, mixing two components with functionalities of two each will result in a linear polymeric biomaterial, and the mixing to two components with functionalities of at least two each, one of the components having a functionality of more than two, will result in a cross-linked biomaterial. Both types of biomaterials can be useful.

In cross-linked biomaterials, the components can be very hydrophilic and the overall material can yet remain as an intact solid, not dispersing throughout the body. If such a non-dispersing system is desired for a linear polymeric biomaterial, it is useful if at least one precursor component be hydrophobic, such that the resulting biomaterial also be insoluble in water or body fluids. Other approaches are also possible, for example, when the two precursor components otherwise interact to become insoluble, or when one or both precursors respond to pH, temperature or other stimuli to become more or less soluble, or when one precursor component is a polycation and the other precursor component is a polyanion, or when one precursor component strongly hydrogen bonds to the other.

The chemical reaction system of the present invention makes use of addition reactions, in which one component possesses a strong nucleophile and the other component possesses a conjugated unsaturation, or a conjugated unsaturation. Of particular interest in this invention as strong nucleophiles are thiols. Preferably, the system makes use of conjugate addition reactions between a thiol and a conjugated unsaturation (e.g., an acrylate or a quinone). This reaction system can be made to be self-selective, meaning substantially unreactive with other chemical groups found in most sensitive biological compounds of interest (most drugs, peptides, proteins, DNA, cells, cell aggregates, and tissues). It is particularly useful when one or both of these components is part of a polymer or oligomer, however other possibilities are also indicated herein.

Many proteins contain the amino acid cysteine, the side chain of which terminates in a thiol. In spite of this, very few proteins have free thiols; most proteins contain an even number of cysteine residues, and these are then paired and form disulfide cross-links between various regions of the protein. Some proteins contain an odd number of cysteine residues and most of these are present as disulfide linked dimers, again resulting in no free thiol residues being present in the native protein. Thus, there are very few free thiols in proteins. Some important electron transferring molecules, such as glutathione, contain a free thiol, but these molecules are generally restricted in their spatial location to the inside of a cell. Accordingly, conjugated unsaturated structures presented outside the cell will be substantially unreactive with most proteins at near-physiological conditions. Amines are also nucleophiles, although not as good a nucleophile as thiols. The pH of the reaction environment is important in this consideration. In particular, unprotonated amines are generally better nucleophiles than protonated amines. At physiological pH, amines on the side chain of lysine are almost exclusively protonated, and thus not very reactive. The alpha amine of the N-terminus of peptides and proteins has a much lower pK than the side chain epsilon amine; accordingly, at physiological pH it is more reactive to conjugate additions than are the epsilon amines of the lysine side chain.

Notwithstanding, the thiol is substantially more reactive than the unprotonated amine. As stated, the pH is an important in this consideration: the deprotonated thiol is substantially more reactive than the protonated thiol. In conclusion, the addition reactions involving a conjugated unsaturation, such as an acrylate or a quinone, with a thiol, to convert two precursor components into a biomaterial will often be best carried out (meaning fastest, most self-selective) at a pH of approximately 8, where most of the thiols of interest are deprotonated (and thus more reactive) and where most of the amines of interest are still protonated (and thus less reactive).

When a thiol is used as the first component, a conjugate structure that is selective in its reactivity for the thiol relative to amines is highly desirable.

If the conjugated structures are kept outside of cells, there are very few reactive nucleophiles with which to react to induce toxicity. One can typically accomplish this spatial restriction by making the conjugated component be of high molecular weight, be hydrophilic, or both.

Polyethylene glycol (PEG) provides a very convenient building block. One can readily purchase or synthesize linear (meaning with two ends) or branched (meaning more than two ends) PEGs and then functionalize the PEG end groups to introduce either a strong nucleophile, such as a thiol, or a conjugated structure, such as an acrylate or a quinone. When these components are either mixed with each other or are mixed with a corresponding component, a hydrogel material will form. One may react a PEG component with a non-PEG component, controlling the molecular weight or hydrophilicity of either component to manipulate the mechanical characteristics, the permeability, and the water content of the resulting biomaterial. These materials are generally useful in medical implants, as described in more detail below.

In the formation of biomaterials, especially biomaterials where degradation in vivo is desirable, peptides provide a very convenient building block. It is straightforward to synthesize peptides that contain two or more cysteine residues, and this component can then readily serve as the nucleophilic precursor component of a biomaterial, especially a hydrogel biomaterial. For example, a peptide with two free cysteine residues will readily form a hydrogel when mixed with a PEG triacrylate at physiological or slightly higher pH (e.g., 8 to 9; the gelation will also proceed well at even higher pH, but at the potential expense of self-selectivity). When the two liquid precursor components are mixed together, they react over a period of a few minutes to form an elastic gel, consisting of a network of PEG chains, bearing the nodes of the network, with the peptides as connecting links. The peptides can be selected as protease substrates, so as to make the network capable of being infiltrated and degraded by cells, much as they would do in a protein-based network. The gelation is self-selective, meaning the peptide reacts mostly with the PEG component and no other components, and the PEG component reacts mostly with the peptide and no other components; if desired, one can design and incorporate bifunctional agents to provide chemical bonding to other species (e.g., a tissue surface). These gels are operationally simple to form: one mixes two liquid precursors, one containing the peptide and the other containing the functionalized PEG. Because, in this example, physiological saline can serve as the solvent, and because minimal heat is generated by reaction, and because neither the PEG triacrylate nor the peptide can readily diffuse inside cells, the gelation can be carried out in vivo or in vitro, in direct contact with tissue, without untoward toxicity. It is clear that polymers other than PEG may be used, either telechelically modified or modified on their side groups.

Protease Sites

One special feature of the chemical cross-linking scheme of this invention is that it is self-selective, meaning that it does not react with other features on peptides or proteins. Thus, one can employ peptides as one component, as described above, and not chemically react with side groups on the peptide other than cysteine residues. This means that a variety of bioactive peptides can be incorporated into the resulting biomaterial structure. For example, a peptide used as a dithiol for cross-linking purposes can be designed to be a substrate for an enzyme used by cells migration through tissues and remodel tissues (e.g., as a substrate for plasmin, elastase or matrix metalloproteinases (MMPs), such as collagenase). The degradation characteristics of the gels can be manipulated by changing the details of the peptide that serves as the cross-linking nodes. One may make a gel that is degradable by collagenase, but not plasmin, or by plasmin, but not collagenase. Furthermore, it is possible to make the gel degrade faster or slower in response to such an enzyme, simply by changing the amino acid sequence so as to alter the $K_m$ or $k_{cat}$, or both, of the enzymatic reaction. One can thus make a biomaterial that is biomimetic, in that it is capable of being remodeled by the normal remodeling characteristics of cells.

Adhesion Sites

One can incorporate peptide sites for cell adhesion, namely peptides that bind to adhesion-promoting receptors on the surfaces of cells into the biomaterials of the present invention. It is straightforward to incorporate a variety of such adhesion-promoting peptides, such as the RGD sequence from fibronectin or the YIGSR (SEQ ID NO: 44) sequence from laminin. As above, this can be done, for example, simply by mixing a cysteine-containing peptide with PEG diacrylate or triacrylate, PEG diacrylamide or triacrylamide or PEG diquinone or triquinone a few minutes before mixing with the remainder of the thiol-containing precursor component. During this first step, the adhesion-promoting peptide will become incorporated into one end of the PEG multiply functionalized with a conjugated unsaturation; when the remaining multithiol is added to the system, a cross-linked network will form. Thus, for example, when an adhesion peptide containing one cysteine is mixed with a PEG triacrylate (at, e.g., 0.1 mole of peptide per mole of acrylate end group), and then a protease substrate peptide containing two cysteine residues is added to form the three-dimensional network (at, e.g., equimolar less 0.1 mole peptide per mole of acrylate end group), the resulting material will be highly biomimetic: the combination of incorporated adhesion sites and protease sites permits a cell to establish traction in the material as it degrades a pathway for its migration, exactly as the cell would naturally do in the extracellular matrix in vivo. In this case, the adhesion site is pendantly incorporated into the material. One could also incorporate the adhesion site directly in to the backbone of the material. This could be done in more than one way. One way would be to include two or more thiols (e.g., cysteine) in the adhesion peptide or protein. One could alternatively synthesize the adhesion peptide (e.g., using solution phase chemistry) directly onto a polymer, such as PEG, and include at least one thiol (e.g., cysteine) or conjugated unsaturation per chain end.

Growth Factor Binding Sites

One can further enhance the biomimetic nature of the biomaterials of the present invention, especially when they are formed from water-soluble components so as to be hydrogels, by the incorporation of growth factor binding domains. For example, heparin-binding peptides can be employed to bind heparin, which can in turn be employed to bind heparin-binding growth factors, such as bFGF, VEGF, BMP or TGFβ. As such, if the heparin-binding growth factor, heparin, and the activated heparin-binding peptide were mixed with the activated PEG (similarly as described in the preceding section), the resulting gel will slowly release the growth factor, holding most of it until an invading cell released the growth factor by degradation of the gel. This is one of the natural functions of the extracellular matrix in vivo, to serve as a depot for growth factors which become released in injury by local cellular activity. Another related way to sequester heparin-binding growth factors would be more directly through the use of covalently incorporated heparin mimics, for example, peptides with negatively charged side chains, that directly bind growth factors. Moreover, since the biomaterial itself is a network, it can be used to release a growth factor that is simply physically incorporated and is released slowly by degradation or diffusion, or a combination thereof. It should be understood that because the gelation chemistry is self-selective, the growth factor itself and the other bioactive peptides are not chemically modified so as to destroy their biological activity. This important aspect of self-selectivity obviates the need, for example, to encapsulate the growth factor in polymer particles (to thereby protect it from the gelation chemistry, if the gelation chemistry were to react with side groups that are present free on the growth factor, such as the epsilon amines present on the side chains of lysine in the protein).

Drug Delivery from Hydrogels Formed by Conjugate Addition Reactions

Hydrogels are particularly useful for the delivery of protein therapeutics. Hydrogels are biocompatible, and provide a gentle environment for proteins so as to minimize denaturation of the proteins. Conjugate addition reactions with thiols are utilized for the production of gels in the presence of proteins, because of the self-selectivity of these reactions as compared with nucleophilic substitution reactions, free-radical reactions or reactions involving amines for reactivity. Thus, the proteins are physically entrapped within the gels. Additionally, degradable segments can be incorporated within the polymers that form the hydrogel and via degradation of segments within the gel, the proteins will be released as the gel degrades. A particularly useful embodiment of the invention occurs in the case when the conjugate addition reaction itself leads to a structure that is particularly prone to hydrolysis.

In the majority of cases, protein drugs or high molecular weight therapeutics such as antisense oligonucleotides or genes are delivered from degradable hydrophobic materials, such as polylactic acid. However, we describe more hydrophilic materials, such as cross-linked polyethylene glycol functionalized with thiols, with conjugated unsaturations, or both. Other examples exist, including photo-cross-linked polyethylene glycol (Pathak et al., Journal of the American Chemical Society 114:8311-8312, 1992) and polyethylene glycol cross-linked by nucleophilic substitution reactions (Zhao et al. Polymer Preprints 38:526-527, 1997; WO 99/2270, WO 99/34833, and WO 99/14259). The cross-linking via conjugate addition chemistries with thiols exhibits excellent self-selectivity, in that reaction between the conjugated group and other groups, such as amines, in proteins, will be quite slow. When the protein to be incorporated contains a free thiol, this will be reacted with the biomaterial system unless it is otherwise protected or reacted.

An additional advantage to the use of biomaterials formed by conjugate addition with thiols to encapsulate and release proteins arises due to the chemistry of groups generated by the conjugate addition cross-linking. If the conjugated group is an acrylate, then a relatively unstable ester is present in the system. If the acrylate were subjected to free-radical cross-linking, it has been found that such gels degrade only very slowly at pH 7.4 and 37° C., with a gel that degrades over the period of about a year. However, if the acrylate group is reacted with a thiol, the ester of the acrylate group hydrolyzes with a half-life of approximately 3 weeks, producing gels that degrade over about 3 weeks (as described below). Whereas in the case of free-radical cross-linking, special groups must be included between the polyethylene glycol and the acrylate to promote degradation of the gel (such as polylactic acid oligomers; Pathak, supra), no special groups are required between the acrylate and the polyethylene glycol in the case of the conjugate addition cross-linking. One can employ more stable linkers between the conjugated unsaturation and the polymer, and then incorporated a domain that is degradable by hydrolysis, such as an oligomer of glycolic acid, lactic acid, epsilon caprolactone, or trimethylene carbonate, between the polymer and the conjugated unsaturation, to obtain degradation of the biomaterial by degradation of these domains.

Biomedical Applications for Hydrogels

Hydrogels are polymeric materials that are highly swollen with water. For many applications, hydrogels are especially useful. Hydrogels are of interest for myriad biomedical applications. These include but are not limited to barrier applications (adhesion preventives, sealants), drug delivery devices, tissue engineering and wound healing scaffolds, materials for cell encapsulation and transplantation, materials for surgical augmentation of tissues and materials for sealants and adhesives. An incomplete but illustrative list of applications for hydrogels in biomedicine follows:

1. Hydrogels for adhesion prevention are desirable to minimize unwanted post-operative or other post-traumatic adhesions. Such adhesions can be proteinaceous or cellular, or both. For example, postoperative abdominopelvic adhesions can lead to chronic pain, bowel obstruction, and infertility. As a second example, unwanted adhesion between blood platelets and the blood vessel wall surface after balloon angioplasty in the vascular system can lead to thrombosis and restenosis. Materials cured in situ upon a surgical site may be useful in preventing postoperative adhesions, especially when these materials degrade over a period of several days to weeks. Materials cured in situ upon the surface of an injured artery may be useful in preventing thrombosis upon the site of vascular trauma associated with catheter intervention, deployment of a stent, or surgery.

2. Hydrogels as glues or sealants are desirable to seal leaks in tissues that isolate (gas or liquid phase) fluid-containing cavities. Some examples are blood vessels, the skin, the lung, the dura barrier, and the intestine. The materials may be useful internally, for example, in sealing air leaks on the lung, and externally, for example, in closing incisions on the skin.

3. Hydrogels can also be useful as localized drug delivery devices. A drug may be any biologically active molecule, for example, a natural product, synthetic drug, protein (such as growth factors or enzymes), or genetic material. The functional properties of such a drug must be preserved by its carrier. The drug may be released by diffusive mechanisms or by degradation of the gel carrier through a variety of mechanisms (such as hydrolysis or enzymatic degradation) or by other sensing mechanisms (for example, pH induced swelling). Given that many drugs contain reactive groups, it is important that the material that serves as the carrier not react with the material in an undesirable manner; as such, the high self-selectivity of reactions between conjugated unsaturations and thiols is very useful in drug encapsulation.

4. Hydrogels as scaffolds are desirable for tissue engineering and wound healing applications: nerve regeneration, angiogenesis, and skin, bone and cartilage repair and regeneration. Such scaffolds may be introduced to the body pre-seeded with cells or may depend upon cell infiltration from outside the material in the tissues near the implanted biomaterial. Such scaffolds may contain (through covalent or noncovalent bonds) cell interactive molecules like adhesion peptides and growth factors.

5. Hydrogels also have biomedical applications as cell transplant devices. Such devices serve to isolate cells (e.g., allograft or xenograft) from a host's defense system (immunoprotect) while allowing selective transport of molecules such as oxygen, carbon dioxide, glucose, hormones, and insulin and other growth factors, thus enabling encapsulated cells to retain their normal functions and to provide desired benefits, such as the release of a therapeutic protein that can diffuse through the immunoprotection hydrogel membrane to the recipient.

6. Hydrogels can be responsive to their environment. They can be designed to increase network formation, and thus attachment, between gel and tissue because when initially injected the components are water borne and water soluble. Upon transition of the active stimuli (e.g., temperature or pH) one or both of the precursors become water insoluble giving lower average water content and result in increased stiffness and improved mechanical properties of the resulting gel.

In some of these examples cited above, it is desirable to form therapeutic hydrogels at their final destination in the body. Implantable materials which can be injected in the liquid phase to a target site where they can then be transformed into solid materials are therefore of interest. The shape of such an implant can match the tissue topography, and a relatively large implant can be delivered through minimally invasive methods. Often, good adhesion to the underlying tissue substrate can be achieved, for example, by intimate penetration of the liquid precursors into texture on the tissue surface or by phase interpenetration to form an interpenetrating polymer network between the biomaterial polymer network and the natural tissue extracellular materials, which are also a polymer network. One can also design additional materials to serve a role as coupling agent to enhance adhesion. For example, one can design a heterobifunctional coupling agent, with an activated ester (such as an N-succinimidyl activated ester derivative) or an epoxide group on one end and a conjugated structure that reacts slowly with amines on the other end. Such an agent would react with proteins on the tissue surface when applied to the tissue surface and would then immobilize conjugated groups for chemical incorporation into the biomaterial network during polymerization or cross-linking. This pre-treatment step would thereby introduce upon the surface of the tissue chemical groups that could participate in the self-selective cross-linking between the two components of the final precursor solution.

There are many ways to form biomaterials including hydrogels. However, materials made in contact with sensitive biological materials, including cells or tissue, or intended for implantation or other contact with the body are subject to special constraints. In the text below, the situation of formation of a biomaterial hydrogel is considered, because of the special usefulness of biomaterial hydrogels. The approaches are generally the same for non-hydrogel materials, and the approaches described below should be understood to be generalizable. The network formation process must proceed in relatively mild conditions with regard to solvent system, temperature and exothermicity, and pH. Precursors and products (of gelation reactions and of gel degradation) should be substantially non-toxic, with toxic being defined as inducing a medically unacceptable tissue reaction in a medically relevant context.

The approaches described herein using conjugate addition reactions with thiols to form biomaterials simplify the process of gel formation (no light or temperature changes are required) and add greatly to usefulness by being self selective (in general not reacting with proteins that are incorporated as biopharmaceuticals or are present on cell and tissue surfaces). Furthermore, because of the self-selectivity, it is possible to much more flexibly incorporate peptides into the biomaterial itself, for example, as protease cleavage sites (to provide degradation), cell adhesion sites, or heparin or growth factor binding sites.

There exist numerous applications in medicine where in situ cross-linking is desired but where hydrogels are not desired. These can include applications where a high strength material is desired. High strength hydrogels can be formed, but in general non-hydrogel materials can be stronger. These materials can be obtained either by cross-linking, using the scheme of this invention, in the presence of a low toxicity non-aqueous solvent, such as ethylacetate, a low molecular weight PEG, or from cross-linking neat without any solvent, from liquid precursors. For example, a hydrolytically degradable strong material could be formed from a low molecular weight poly(epsilon caprolactone) diacrylate (which is a liquid) as a hydrophobic component. Such materials can be either linear polymeric biomaterials or cross-linked polymeric biomaterials. This may also be achieved by using precursors that exhibit sensitivity to pH, temperature or other stimuli which can be manipulated. In this manner, the precursors will undergo a transition from soluble to insoluble after/during application. This will allow easy handling but allow the improvement of mechanical properties by using non-hydrogel (low water content) materials.

It is possible to prepare structural materials with significant mechanical strength in situ using conjugate addition with thiols. If high cross-linking density and/or low water content are used, gels or materials with high mechanical strength can be obtained. Multifunctional, low molecular weight precursors with limited or no water solubility can be combined to form strong cross-linked materials. These insoluble or partially soluble precursors can be combined, if they are liquid, by dispersing in aqueous with or without the assistance of emulsifiers. This emulsifier may be nontoxic or minimally toxic surfactants, such as sorbitan monooleate, or it may be a protein such as albumin. Inorganic particles can also assist in the water dispersion of such precursors. The mechanical properties of the structural gels obtained by this method can be modified by the addition of inorganic particles, hydrophilic or hydrophobic additives, or by the use of multimodal molecular weight precursors (precursors with multiple discreet molecular weights). The addition of inorganic particles increases the stiffness of the cross-linked material and can increase the ultimate strength and the fatigue resistance of the material. The addition of hydrophilic additives can be used to increase the water content and to soften the materials. Depending of the chemical composition, the addition of hydrophobic additives can be used to reduce the water content of the gel and can be used to harden and/or strengthen the materials. This may also be used to enhance elasticity. The density of cross-linking can be affected by the molecular weight of the original precursors. Increase of the molecular weight can reduce the cross-linking density and be used to modulate the mechanical properties of the final biomaterial.

II. Cross-linking Chemistry

As used herein, the symbol P is employed to indicate the part of a molecule that lies between two reactive sites (telechelic sense) or is grafted with reactive sites (grafted sense). With telechelic polymers, P will lie between two strong nucleophiles, such as two thiols, or between two conjugated unsaturations (e.g., in the case of a PEG diacrylate or a PEG dithiol. P is a PEG chain). In the case of a PEG triquinone or trithiol, P is a three-armed, branched PEG. In the case of a block copolymer acrylate-(lactic acid oligomer)-PEG-(lactic acid oligomer)-acrylate or quinone-(lactic acid oligomer)-PEG-(lactic acid oligomer)-quinone, P is the (lactic acid oligomer)-PEG-(lactic acid oligomer) block copolymer. In the case of a graft copolymer (e.g., polylysine-graft-(PEG acrylate) or polylysine-graft-(PEG quinone) or polylysine-graft-(PEG thiol)), in which the geometry of the polymer is as a bottle-brush with the tips of the bristles containing either the conjugated unsaturations or the strong nucleophile, P is polylysine-graft-(PEG). P can also present the reactive groups in the side chains: every polymer bearing alcohols or amines in the side chains is easily acrylated, for example, in order to present multiple conjugated unsaturated groups for the conjugate addition reaction. Polymers containing carboxylic acids can be derivatized to expose, for example, quinines groups. P need not be polymeric in the usual sense of the word. For example, in the case of ethylene glycol diacrylate or diquinone, P is the ethylene unit. In the case of a peptide, for example, YCXXXXXXCY (SEQ ID NO: 1) or CXXXXXXC (SEQ ID NO: 2), where C is the amino acid cysteine and X and Y are other amino acids, such that XXXXXX (SEQ ID NO: 3) could be a sequence that functions as a substrate for a protease such as collagenase, P is XXXXXX. The length of XXXXXX or the number of X (e.g., Xn) can be any length or number (n=0). In the case of 1,2 ethylene dithiol, P is the ethylene. Thus, P is the molecular part of the precursor component that is interposed between the two, or more, reactive groups on the precursor component. It is often convenient when this is polymeric or oligomeric, but neither case is necessary; small molecules are also of interest and use. Examples of small molecules which may be used include, but are not limited to reduced sugars or analogous compounds, such as mannitol, erythritol, pentaeritrol, trimethylol propane, and glycerol, which can be totally or partially acrylated, or reacted with beta-mercapto propionic acid to give thiols. Di- or multicarboxylic acids, such as EDTA, citric acid, succinic acid, and sebacic acid, can be converted to quinones.

Definition of Michael-type Reaction

The 1,4 addition reaction of a nucleophile on a conjugate unsaturated system is referred to as a Michael-type reaction. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Double bonds spaced by a CH or $CH_2$ unit are referred to as homoconjugated double bonds.

Michael-type addition to conjugated unsaturated groups can take place in good to quantitative yields at room or body temperature and in mild conditions with a wide variety of nucleophiles (Pathak, supra; Moghaddam et al., Journal of Polymer Science: Part A: Polymer Chemistry 31:1589-1597, 1993; and Zhao, supra). Conjugated unsaturated groups, such as vinyl sulfones (Pathak, supra), have been used to link PEG or polysaccharides to proteins through Michael-type reactions with amino- or mercapto-groups.

The innovation of the present invention consists in the fact that a biocompatible gelling of biomaterial precursors to form a biomaterial is rapidly provided by the use of a wide variety of conjugated unsaturated compounds reacting with thiols in a self-selective manner. The gel formation kinetics and the mechanical and transport properties of the product are tailored to the needs of the application. The possibility to incorporate proteinaceous or peptidyl material is envisaged mainly in order to obtain a proteolytically degradable material or for specific recognition processes within it, but primarily by reaction with intentionally incorporated cysteine residues; pure protein PEGylation is outside of the scope of the present invention, since it does not result in a biomaterial. Groups such as maleimides and vinylsulfones are useful in these cross-linking reactions, but these tend to be less useful than others because of a relatively high rate of reactivity with amines relative to other nucleophiles such as compared to some of the conjugated systems described below. As such, the use of conjugated unsaturations that display lower overall reactivity, including quinones and acrylates.

Conjugated Unsaturated Structures

It is possible to perform Michael-type addition reactions on a wide variety of conjugated unsaturated compounds. In the structures shown below, an oligomeric or polymeric structure is indicated as P. Various possibilities for the specific identity of P are discussed further herein. P can be coupled to reactive conjugated unsaturated groups in structures such as those numbered 1 to 20.

In the drawings, P is intended as terminated with a $CH_2$, CH or C group.

Reactive double bonds can be conjugated to one or more carbonyl groups in a linear ketone, ester or amide structure (1, 2) or to two in a ring system, as in a maleic or paraquinoid derivative (3, 4, 5, 6, 7, 8, 9, 10). In the latter case the ring can be fused to give a naphthoquinone (6, 7, 10) or a 4,7-benzimidazoledione (8) (Pathak, supra) and the carbonyl groups can be converted to an oxime (9, 10). The double bond can be conjugated to a heteroatom-heteroatom double bond, such as a sulfone (11), a sulfoxide (12), a sulfonate or a sulfonamide (13), a phosphonate or phosphoamide (14). Finally, the double bond can be conjugated to an electron-poor aromatic system, such as a 4-vinylpirydinium ion (15). Triple bonds can be used in conjugation with carbonyl or heteroatom-based multiple bonds (16, 17, 18, 19, 20).

Chemical Structures:

1

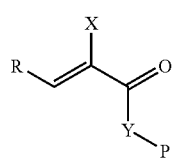

X = H, CH3   R = H        Y = NH, O, 1,4-Ph
    CN, COOW R = H, W, Ph  Y = NH, O, 1,4-Ph

W = C1-C5 linear aliphatic chain

2

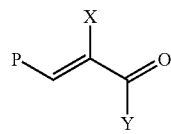

X = CN, COOW   Y = OW, Ph

W = C1-C5 linear aliphatic chain

-continued
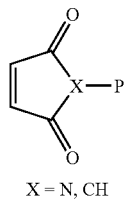
X = N, CH
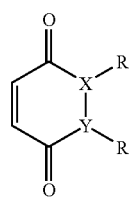
A  X = CH   Y = CH   R = H, W-P (W = NH, O, nihil)
B  X = N    Y = N    R = H, P
C  X—Y=C=C  R = W-P (W = NH, O, nihil)
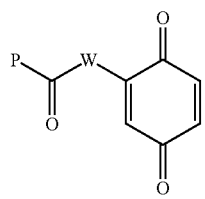
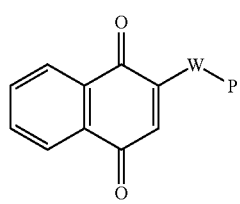
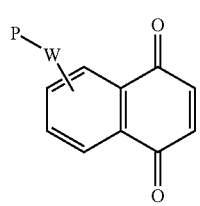
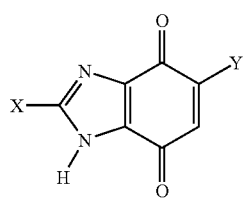
X, Y = H, P
P, P
P, H
P, aliphatic chain
-continued
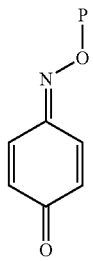
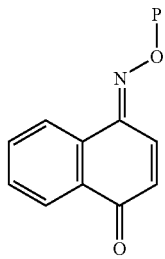
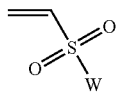
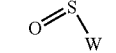
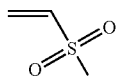
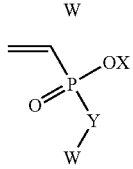
Y = O, NH
X = alkali or alkali earth metal ion, P
W = P, 1,4-Ph-P
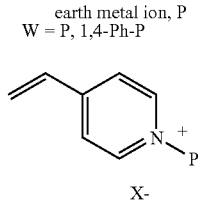
X = halogen, sulphonate
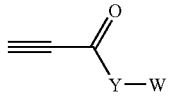
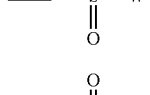
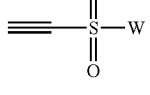

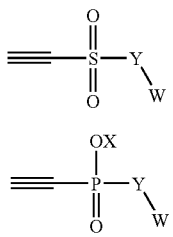

Y = O, NH
X = alkali or alkali earth metal ion, P
W = P, 1,4-Ph-

Structures such as 1 and 2 are based on the conjugation of a carbon-carbon double bond with one or two electron-withdrawing groups. One of them is always a carbonyl, increasing the reactivity passing from an amide, to an ester, and then to a phenone structure. The nucleophilic addition is easier upon decreasing the steric hindrance, or increasing the electron-withdrawing power in the alpha-position: $CH_3<H<COOW<CN$.

The higher reactivity obtained by using the last two structures can be modulated by varying the bulkiness of the substituents in the beta-position, where the nucleophilic attack takes place; the reactivity decreases in the order $P<W<Ph<H$. So, the position of P too can be used to tune the reactivity towards nucleophiles. This family includes some compounds for which a great deal is known about their toxicology and use in medicine. For example, water-soluble polymers with acrylates and methacrylates on their termini are polymerized (by free radical mechanisms) in vivo, in hydrogel sealants and bone cements, respectively. Thus, acrylate and methacrylate-containing polymers have been seen in the body before in clinical products, but for use with a dramatically different chemical reaction scheme.

The structures 3-10 exhibit very high reactivity towards nucleophiles, due both to the cis configuration of the double bond and the presence of two electron-withdrawing groups.

Unsaturated ketones react faster than amides or imides, due to the stronger electronegativity of these carbonyl groups. So, cyclopentendione derivatives react faster than maleimidic ones (3), and para-quinones react faster than maleic hydrazides (4) and also faster than cyclohexanones, due to more extended conjugation. The highest reactivity is shown by naphthoquinones (7).

P can be placed in positions where it does not reduce the reactivity of the unsaturated group, that is in the opposite part of the ring (3, 5), on another ring (7, 8) or O-linked through a para-quinone mono-oxime (9, 10). P can be also linked to the reactive double bond (6, 8), if the nucleophilic addition rate is to be decreased.

The activation of double bonds to nucleophilic addition can be obtained also by using heteroatoms-based electron-withdrawing groups. In fact, heteroatom-containing analogous of ketones (11, 12), esters and amides (13, 14) provide a similar electronic behavior. Structures 13 and 14 can also be used as easily hydrolyzable groups, that can promote a quick gel degradation. The reactivity towards nucleophilic addition increases with electronegativity of the group, that is in the order 11>12>13>14, and is enhanced by the linkage with an aromatic ring. A strong activation of double bonds can also be obtained, using electron-withdrawing groups based on aromatic rings. Any aromatic structure containing a pyridinium-like cation (e.g., derivatives of quinoline, imidazole, pyrazine, pyrimidine, pyridazine, and similar $sp_2$-nitrogen containing compounds) strongly polarizes the double bond and makes possible quick Michael-type additions.

Carbon-carbon triple bonds, conjugated with carbon- or heteroatom-based electron-withdrawing groups, can easily react with sulfur nucleophiles, to give products from simple and double addition. The reactivity is influenced by the substituents, as for the double bond-containing analogous compounds.

The formation of ordered aggregates (liposomes, micelles) or the simple phase separation in water environment increase the local concentration of unsaturated groups and so the reaction rate. In this case, the latter depends also on the partition coefficient of the nucleophiles, which increases for molecules with enhanced lipophilic character.

Nucleophiles

The nucleophiles that are useful are those that are reactive towards conjugated unsaturated groups via addition reactions. The reactivity of the nucleophile depends on the identity of the unsaturated group, as discussed in more detail elsewhere herein, but the identity of the unsaturated group is first limited by its reaction with water at physiologic pH. Thus, the useful nucleophiles will generally be more nucleophilic than $H_2O$ at physiologic pH. Preferred nucleophiles will be ones that are commonly found in biological systems, for reasons of toxicology, but ones that are not commonly found free in biological systems outside of cells. Thus, while there may be examples in which amines can be employed as effective nucleophiles, the most preferred nucleophile is the thiol.

Thiols are present in biological systems outside of cells in paired form, as disulfide linkages. When the highest degree of self-selectivity is desired (e.g. when a therapeutic protein is incorporated, when the gelation reaction is conducted in the presence of tissue and chemical modification of that tissue is not desirable), then a thiol will represent the strong nucleophile of choice.

There are other situations, however, when the highest level of self-selectivity may not be necessary. This would include situations when no therapeutic protein is incorporated and when the gelation reaction is conducted in situ, but when chemical bonding to the tissue is either desirable or is not undesirable. In these cases, an amine may serve as an adequate nucleophile. Here, particular attention is paid to the pH, in that the deprotonated amine is a much stronger nucleophile than the protonated amine. Thus, for example, the alpha amine on a typical amino acid (pK as low as 8.8 for asparagine, average of 9.0 for all 20 common amino acids except proline) has a much lower pK than the side chain epsilon amine of lysine (pK 10.80). As such, if particular attention is paid to the pK of an amine used as the strong nucleophile, substantial self-selectivity can be obtained. Proteins have only one alpha amine (on the N-terminus). By selection of an amine with a low pK, and then formulation of the final precursor solution such that the pH were near that pK, one could favor reaction of the unsaturation provided with the amine provided, rather than other amines present in the system. In cases where no self-selectivity is desired, one need pay less attention to the pK of the amine used as the nucleophile, however to obtain reaction rates that are acceptably fast one must adjust the pH of the final precursor solution such that an adequate number of these amines are deprotonated.

In summary, thiols are the preferred strong nucleophile of this invention, for reasons of pH in the precursor solution and maximal self-selectivity, but there are situations in which amines will also serve as useful strong nucleophiles; the usefulness of particular nucleophiles depends upon the situation envisioned and the amount of self-selectivity desired.

The concept of nucleophilic group is extended herein, so that the term is sometimes used to include not only the functional groups themselves (e.g., thiol or amine), but also molecules which contain the functional group (e.g., cysteine or cystyl residue, or lysine or lysyl residue).

The nucleophilic groups may be contained in molecules with great flexibility in overall structure. For example, a difunctional nucleophile could be presented in the form of Nuc-P-Nuc, where P is used in the sense described herein and Nuc refers to the nucleophile. Likewise, a branched polymer P could be derivatized with a number of nucleophiles to create P-(Nuc)$_i$, where i=2 would be useful. Nuc needs not be displayed at the chain termini of P, for example, a repeating structure could be envisioned: (P-Nuc)$_i$, where i=2 would be useful. Clearly, not all of the P or the Nuc in such a structure need to be identical. It is only necessary that one nucleophilic precursor contain greater than or equal to two such Nuc groups.

Likewise, similar structures of P and the conjugated unsaturated groups described in detail above may be formed. It is only necessary that one conjugated unsaturated precursor contain greater than or equal to two such conjugated unsaturated groups.

It should be noted and understood, that it is not necessary that both precursor components, for example, both the nucleophilic precursor component and the conjugated unsaturated precursor component, actually be polymeric in the usual sense of the word. It is only the functionality that matters. In practice, it is convenient if at least one component is polymeric in the usual sense of the word, but this is not absolutely necessary. For example, useful materials result from the reaction of a PEG triacrylate with dicysteine, and likewise, useful materials result from the reaction of a PEG trithiol and a low molecular weight diacrylate. Finally, useful materials for some applications also result from reaction of a dicysteine and a low-molecular diacrylate.

In practice, it is convenient and useful when one or more precursor component is polymeric in the usual sense of the word. In these cases, P can be synthetic hydrophilic polymers, synthetic hydrophobic polymeric liquids, synthetic hydrophobic polymers that are soluble in solvents of acceptable toxicity or biological influence for the envisioned application, biosynthetic proteins or peptides, naturally occurring proteins or modified naturally occurring proteins, or polysaccharides.

Hydrophilic Polymers

In preferred embodiments, the synthetic polymer P can be poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly (vinyl pyrrolidone), poly(ethylene-co-vinyl pyrrolidone), poly(maleic acid), poly(ethylene-co-maleic acid), poly(acrylamide), or poly(ethylene oxide)-co-poly(propylene oxide) block copolymers This is not an exhaustive list as other hydrophilic polymers could also be used.

P can also be copolymers, block copolymers, graft copolymers, or random copolymers. Blocks, which are polymerized on the ends of the hydrophilic polymers, can be composed of, for example, lactic acid, glycolic acid, epsilon-caprolactone, lactic-co-glycolic acid oligomers, trimethylene carbonate, anhydrides, and amino acids, for example, to confer degradability by hydrolytic or enzymatic means. This list is not exhaustive; other oligomers may also be used for block copolymers.

Random copolymers can be based on vinyl alcohol, such as poly(N-vinylpyrrolidone-co-vinyl alcohol) or poly(ethylene-co-vinyl alcohol), with different compositions, can be derivatized with conjugated unsaturated groups, such as acrylates, benzoquinones, naphthoquinones and others. The vinyl alcohol copolymers can be functionalized with $(CH_2)_n COOH$ groups by reaction with co-bromo-carboxylic acids. The resulting polymers or acrylic or methacrylic acid copolymers can be used for the attachment of quinone groups. Comonomer composition and extent of functionalization do not influence dramatically the reaction rates, unless they determine solubility or phase transition. On the other hand, they determine the final mechanical properties.

It should be noted that one component P could even be a solid, such as a colloidal particle with either nucleophiles or sites of conjugated unsaturation upon it.

Proteins and Biosynthetic Proteins

P may be a protein. The protein can be a naturally occurring or recombinant protein. In general terms, the recombinant proteins are any length amino acid material generated through recombinant DNA technology. Examples of components these can have include peptide sequences which encode degradation sites for proteases, peptide sequences for other biological signals and non biointeractive sequences.

Any naturally occurring protein can also be P. More specifically, a naturally occurring protein is composed of several Ps which are separated by nucleophiles. For example, serum albumin, a 584 amino acid protein, contains 5.7% cysteine, 9.9% lysine and 3.1% tyrosine. The amino acid sequences which occur between, for example, cysteine, tyrosine and lysine make up distinct Ps. While albumin in its natural state may be less than useful for the purposes of cross-linking by conjugate addition reactions between conjugated unsaturations and thiols on the protein, albumin can be readily processed by reduction so as to form a poly(amino acid) with some or all of its cysteine residues free or it can be chemically derivatized to introduce multiple thiol groups.

Peptides

In some instances, P may be a peptide or a polypeptide, where the nucleophile is the amino acid cysteine, resulting in peptides of structures similar to $H_2N$-CXXXXXX-CXXXXXC-COOH (SEQ ID NO: 4) or $H_2N$-CXXXXXC-COOH (SEQ ID NO: 5), where C is the one-letter representation of cysteine, and X represents any amino acid except cysteine, in one embodiment, or Acetyl-NH-YXXXXX-YXXXXXY-COOH (SEQ ID NO: 6) where Y is the one-letter representation of tyrosine, and X represents any amino acid except cysteine or tyrosine, in another embodiment. The length of XXXXX (SEQ ID NO: 7) or the number of X (e.g., Xn) can be any length or number (n=0). It is particularly useful when the sequences in the domains shown as XXXXX above are substrates for enzymes that are involved in cell migration (e.g., as substrates for enzymes such as collagenase, plasmin or elastase), although the domains need not be limited to these. One such particularly useful sequence, as a substrate for the enzyme plasmin, is described in the examples. A variety of such peptides may be learned from a study of the literature of these enzymes. For example, such a study shows substrate sites for the important protease plasmin (Table 1; SEQ ID NOS: 8-24):

TABLE 1

Plasmin Substrate Sites found in Fibrin (ogen) (Fg)**

| P3 | P2 | P1 | P1' | P2' | P3' | Fg chain and site | Reference | SEQ ID NO: |
|---|---|---|---|---|---|---|---|---|
| Arginyl Sites | | | | | | | | |
| G | P | R+ | V* | V* | E- | α 19 | 3 | 8 |
| N | N | R+ | D- | N | T | α 104 | 2, 4 | 9 |
| Y | N | R+ | V* | S | E- | α_110 | 2 | 10 |
| Q | M* | R+ | M* | E- | L* | α 239 | 1 | 11 |
| G | F* | R+ | H+ | R+ | H+ | α 491 | 5 | 12 |
| G | Y | R+ | A* | R+ | P | β 42 | 2, 3 | 13 |
| Lysyl Sites | | | | | | | | |
| Y | Q | K+ | N | N | K+ | α_78 | 3 | 14 |
| L* | I* | K+ | M* | K+ | P | α 206 | 1, 2 | 15 |
| N | F* | K+ | S | Q | L* | α_219 | 1 | 16 |
| E- | W | K+ | A* | L* | T | α_230 | 1 | 17 |
| S | Y | K+ | M* | A* | D | α_583 | 5 | 18 |
| T | Q | K+ | K+ | V* | E- | β_53 | 3 | 19 |
| R+ | Q | K+ | Q | V* | K+ | β_130 | 2 | 20 |
| Q | V* | K+ | D- | N | E- | β_133 | 4 | 21 |
| L* | I* | K+ | A* | I* | Q | γ_62 | 4 | 22 |
| T | L* | K+ | S | R+ | K+ | γ_85 | 2, 3 | 23 |
| S | R+ | K+ | M* | L* | E- | γ_88 | 2 | 24 |

Ref. 1: Takagi T. and R. F. Doolittle, Biochemistry 14: 5149-5156, 1975;
Ref. 2: Hantgan R. R., et al., Hemostasis and Thrombosis: Basic Principles and Clinical Practice, Third Edition. Edited by R. W. Colman et al. J. B. Lippincott Company: Philadelphia, 1994;
Ref. 3: Takagi T. and R. F. Doolittle, supra.;
Ref. 4: Nomura S. et al., Electrophoresis 14: 1318-1321 1993.;
Ref. 5: Standker L. et al., Biochemical and Biophysical Research Communications 215: 896-902 (1995).
*Indicates a hydrophobic amino acid; +/− Indicates a charged side chain, either cationic (+) or anionic (−).
**Single letter amino acid code: A, alanine; C, cysteine; D, aspartic acid; E, glutamic acid; F, phenylalanine; G, glycine; H, histidine; I, isoleucine; K, lysine; M, methionine; N, asparagine; P, proline; Q, glutamine; R, arginine; S, serine; T, threonine; V, valine; W, tryptophan; Y, tyrosine.

Given that plasmin is an important enzyme in cell migration and tissue/clot remodeling, these substrates or parts of these substrates represent useful sequences within the sites indicated above as XXXXX in P.

Likewise, collagenase is an important enzyme in cell migration and tissue remodeling. A study of the literature on collagenase indicates also a variety of substrate sites, which represent useful identities for XXXXX in P (Table 2; SEQ ID NOS: 25-31):

TABLE 2

Collagenase Substrate Sites found in Collagen

| P3 | P2 | P1 | P1' | P2' | P3' | Collagen type and site | Ref. | SEQ ID NO: |
|---|---|---|---|---|---|---|---|---|
| P | Q | G | I* | A* | G | calf & chick α1(I); human cartilage α 1 (II) | 6 | 25 |
| P | Q | G | L* | L* | G | calf α 2 (I) | 6 | 26 |
| P | Q | G | I* | L* | G | chick α 2 (I) | 6 | 27 |
| P | Q | G | L* | A* | G | chick α 2 (I); human skin α 1 (III) | 6 | 28 |
| P | L* | G | I* | A* | G | human liver α 1 (III) | 6 | 29 |
| P | L* | G | L* | W | A* | human | 7 | 30 |
| P | L* | G | L* | A* | G | human | 8 | 31 |

Ref. 6: Netzel-Arnett S. et al., The Journal of Biological Chemistry 266: 6747-6755, 1991;
Ref. 7: Upadhye S. and V. S. Ananthanarayanan, Biochemical and Biophysical Research Communications 215: 474-482, 1995;
Ref. 8: Liko Z., et al., Biochem Biophys Res Commun 227: 351-35, 1996.

The use of enzyme degradation sites within P, either in the nucleophile precursor component (most easy, since cysteine in the sequence may be used to provide a thiol as a nucleophile) or as the conjugated unsaturated precursor component, is that the rate of biomaterial resorption or remodeling may be linked to the rate and progress of healing, for example, as indicated by cell infiltration.

It is particularly powerful to note that the rate of biomaterial resorption may be modulated by adjustments to the oligopeptide sequence so as to alter the $K_m$ and $k_{cat}$ of the substrate site. For example, a study of the literature on the enzymology of collagenase substrate sites shows that it is possible to adjust the rate of degradation of substrates by the design of the sequence of the substrates (Table 3 SEQ ID NOS: 32-38):

TABLE 3

Design of Collagenase (Matrix metalloproteinase I)-Sensitive Peptide Sequences

| No. | Sequence | $k_{cat}/K_m$ relative to that of PQGIAG | SEQ ID NO: |
|---|---|---|---|
| 1 | GPQGIAGQ | 100% (normal) | 32 |
| 2 | GPVGIAGQ | 30% (slow) | 33 |
| 3 | GPQGVAGQ | 9% (slower) | 34 |
| 4 | GPQGRAGQ | <5% (very slow) | 35 |
| 5 | GPQGIASQ | 130% (fast) | 36 |
| 6 | GPQGIFGQ | >300% (faster) | 37 |
| 7 | GPQGIWGQ | >700% (very fast) | 38 |

Netzel-Arnett S. et al.. The Journal of Biological Chemistry 266: 6747-6755, 1991

Accelerators

Poorly reacting nucleophiles are referred to as having a pseudo-first order half-life of more than approximately 15 minutes (with the conjugated unsaturated group present in excess; slower reactions might be useful in some medical circumstances), at a pH generally defined as pH more than 5 and less than 9, and at a temperature greater than 25° C. and less than 40° C. Radical initiators are referred to as organic or water-soluble molecules undergoing spontaneous, thermally- or photochemically-initiated homolytic scission of carbon-heteroatom or heteroatom-heteroatom bonds, to produce carbon- or heteroatom-based radicals. The use of such radical initiators as accelerators, while not preferred, should be understood to be superior to polymerization, in that the concentration of free radicals employed can be much lower. The addition rate of poorly reacting nucleophiles to conjugated unsaturated groups can be enhanced by the presence of accelerating substances; these can be radical initiators, photosensitizers; (alone or in combination with radical initiators; Pathak, supra), low molecular weight Lewis acids (Pathak, supra), solid-state catalysts characterized by Lewis acidity or by the presence of quaternary ammonium ions, such as an Amberlyst resin (Pathak, supra) or a montmorillonite clay (Pathak, supra), or hydrogen bonding receptors, based on N,N-disubstituted urea or peptidic structures (Pathak, supra). In the last case, the acceleration mechanism is based on the stabilization by hydrogen bonding of the enolate-like transition state, following the attack of the nucleophile on the conjugated olefin; tailor-made antibodies can be used on this purpose (Pathak, supra).

In a typical experiment a concentrated (typically greater than or equal to 10% w/w, but simply at a sufficiently high concentration to achieve the desired behavior) solution of a P derivative containing a number of conjugated unsaturated groups greater than one per P residue is quickly mixed with a concentrated (>10%, but simply at a sufficiently high concentration to achieve the desired behavior) solution of a thiol- or suitable amino-containing compound (especially thiols, in applications where the highest degree of self-selectivity may not be required), with a number of nucleophilic species greater than two. An accelerating species in catalytic quantities (<1-2% w/w) can be introduced during the mixing stage. Higher temperatures (up to 60° C.) can be used for a short time after the mixing to activate the cross-linking reaction. For situations when the material is to be injected into the body and then allowed to react in situ to form the final biomaterial, injection temperatures up to approximately 50° C. may be acceptable.

III. Polymer Network Formation

Functionality

Utilizing terminology from polymer science, polymers can be made by reaction of monomers with a functionality of 2. Cross-linked networks of polymers can be made if some or all of the monomers have a functionality greater than 2. Molecules are described herein having a functionality greater than or equal to 2 (monomers or macromers), which can be reacted together to form a cross-linked network, where functionality is defined in terms of addition reactions. As used herein, polymerization refers to the reaction of monomers or macromers with functionality of 2, and cross-linking refers to the reaction of monomers or macromers some or all of which have a functionality greater than 2. The term monomers here is not limited to small molecules, but can also refer to polymers and biopolymers.

The monomers described are of two classes, which when reacted together form a linear or cross-linked biomaterial. Both classes of monomers are required to be mixed together for cross-linking to occur (different approaches for mixing are described immediately below). One class of monomer contains 2 or more conjugated unsaturated groups (thus, a functionality of 2 or more), preferably conjugated. The other class of monomer contains 2 or more nucleophiles (thus, a functionality of 2 or more), preferably nucleophiles that are stronger nucleophiles than others present as other components of the system, for example, thiols when compared with amines that may be present as desirably non-reactive components of the system.

When water-soluble precursor monomers are mixed together (referred to as the final precursor solution), linear or cross-linked gels or networks are formed, and such reactions can proceed in water at physiologic or nearly physiologic salt concentrations and pH. It is not necessary that the monomers be entirely soluble in water, and indeed it is sometimes beneficial that they not be soluble in water. In such cases, gels may not be obtained as the final material, but rather more hydrophobic, less water-swelling materials. These can be particularly useful in the delivery of hydrophobic drugs and in the formation of materials with substantial structural strength. It is only necessary that the two components be either soluble in each other or at least finely dispersible in each other, perhaps in the presence of an emulsifying agent. In this manner, the two components can come close enough to each other to react to form the linear or cross-linked material.

It is also possible to work with solutions of monomers formed in a solution other than water. For example, the use of N-methylpyrrolidone (NMP) as a solvent in injectable biomaterial systems is known, and as such it is possible, when one wishes to work with the precursor components in solution, but with precursor components that are not freely soluble in water, to employ certain organic solvents that are acceptable for use with the sensitive biological material under consideration.

When a drug is being incorporated in the laboratory or in a manufacturing line, then there is great flexibility in the selection of this organic solvent, since at least most of it will be removed before the implant is provided to the subject. When a material is being formed on the skin, then a great deal of flexibility also exists, due to the low skin toxicity of many organic solvents, including NMP, acetone, ethanol, isopropanol and ethyl acetate. When a material is being formed in the body, then the list of acceptable solvents is considerably smaller and is dominated by toxicity concerns. In such cases, NMP is a particularly favorable organic solvent. The toxicity of the solvent system can also be modulated by employing a mixed solvent system, comprising the organic solvent and water, to lower the overall concentration of organic solvent but to still provide good solubility or dispersability in the mixed solvent system.

Mixing to form the final precursor solution can occur by several means. Most straightforwardly, one solution contains the nucleophilic precursor component and one solution contains the conjugated unsaturated precursor component. These two components are formulated in solvent and buffer systems such that the pH and concentrations obtained after mixing are appropriate for the chemical reaction to proceed. Such mixing could occur in a static mixer at the function of two syringes, for example.

Other mixing approaches can be imagined. For example, mixing can occur between fine particles of each of the two precursor solutions in an air spray. One solution could be prepared from both precursor components, but at a pH, for example, such that the reaction did not proceed or proceeded only slowly. After placement of the pre-mixed precursor solution, pH could be adjusted (e.g., by change of temperature, or mixing with acid or base, or by a chemical reaction to create an acid or base, or diffusion of an acid or base), to result in a final condition in the final precursor solution that was appropriate for the chemical reaction to proceed. Another approach can be to prepare the final precursor solution at a temperature such that the reaction did not proceed or proceeded only very slowly, either related to the activation energy of the reaction or to a buffer with temperature-sensitive characteristics or both. Upon warming or cooling (most usefully warming) to the final application temperature (e.g., to body temperature after injection), the conditions in the final precursor solution would be appropriate for the chemical reaction to proceed.

Medical Applications

Since the biomaterials are useful as medical implants or devices, or for drug delivery in humans, the system of molecules used in the precursor solution must meet certain criteria. These include:

1. The rate of the Michael-type reaction must occur over a clinically relevant period of time at a clinically relevant temperature and pH. Generally, gelation over a period of less than approximately 15 minutes, at a pH generally more than 7 and less than 9 and at a temperature greater than 25 and less than 40° C. is desirable.

2. The reaction must be sufficiently self-selective, with self-selectivity considerations including the following. For the formation of gels in the presence of drugs containing amines or where reaction with cell and tissue components is undesirable, the conjugated unsaturation must react very slowly with amines at the pH of application of the final precursor solution. Preferably, a ratio of reactivity of the conjugated unsaturation for the nucleophile of intentional reactivity to the amine, in this case the nucleophile of unintentional or undesirable reactivity, in excess of ten and more preferably even higher is desired. Typically, the approach of Michael-type addition between conjugated unsaturations and thiols will not be useful for drugs that contain themselves conjugate unsaturations or thiols. Exceptions include cases when the reactivity of the group on the drug is considerably less than the reactivity on the corresponding group in the biomaterial precursor and cases when such reactions are not detrimental, for example, when grafting to the biomaterial network are not detrimental.

3. The reactants must be stable in water, when the precursor solutions are prepared in water. Stable is defined as reacting slowly, with slowly defined as sufficiently slow to allow the reaction between the two components to proceed and still result in the formation of the desired biomaterial.

4. The addition reaction in the final precursor solution must not be exothermic to the point of causing tissue damage, drug breakdown or other detrimental results to the biological material under consideration. The temperature of the gelling solution generally should not be raised above 60° C. during gelation, and preferably even cooler maximum reaction temperatures are desirable.

5. The components of the precursor solution must not be toxic at concentrations which diffuse out of the final precursor solution as it is applied, with the word toxic being defined as inducing a medically unacceptable tissue reaction in a medically relevant context.

The criteria defined above in this section limit the identity of the molecules which may be useful in the precursor solution, by limiting the identity of the chemical group used for the cross-linking.

Additional Biofunctionality

One strong benefit of the use of the addition reactions described herein is that other bioactive bifunctional groups can be incorporated into the biomaterial, for example, to provide sites for binding of adhesion-promoting receptors on the cell surface or sites for growth factor binding.

Adhesion Peptides

A variety of adhesion-promoting peptides have been identified as being the active domains of adhesion-promoting proteins such as fibronectin, vitronectin, laminin, collagen, von Willebrand factor, osteonectin, and so forth. These peptides can be readily incorporated into the biomaterial, when they are designed with a strong nucleophile in the peptide chain, such as a cysteine. Such an example is demonstrated in the examples. A partial list of the peptides that would be of interest follows (Table 4; SEQ ID NOS: 39-49):

TABLE 4

Cell Binding Domain Sequences of Extracellular Matrix Proteins

| Protein | Sequence | Role | SEQ ID NO: |
|---|---|---|---|
| Fibronectin | RGDS | Adhesion of most cells, via $\alpha_5\beta_1$ | 39 |
|  | LDV | Adhesion | N/A |
|  | REDV | Adhesion | 40 |
| Vitronectin | RGDV | Adhesion of most cells, via $\alpha_v\beta_3$ | 41 |
| Laminin A | LRGDN | Adhesion | 42 |
|  | IKVAV | Neurite extension | 43 |

TABLE 4-continued

Cell Binding Domain Sequences of Extracellular Matrix Proteins

| Protein | Sequence | Role | SEQ ID NO: |
|---|---|---|---|
| Laminin B1 | YIGSR | Adhesion of many cells, via 67 kD laminin receptor | 44 |
|  | PDSGR | Adhesion | 45 |
| Laminin B2 | RNIAEIIKDA | Neurite extension | 46 |
| Collagen I | RGDT | Adhesion of most cells | 47 |
|  | DGEA | Adhesion of platelets, other cells | 48 |
| Thrombospondin | RGD | Adhesion of most cells | N/A |
|  | VTXG | Adhesion of platelets | 49 |

After Yamada, Y., and Kleinman, H. K., Curr. Opin. Cell Biol. 4: 819, 1992.

These peptides are potentially useful in controlling a variety of cellular reactions, such as cell attachment, migration and overgrowth upon a material surface (especially when the material is not degradable or is slowly degradable), cell migration through a material (especially when the material is more readily degradable by the incorporation of protease substrates within one of the two precursor components), and the induction of particular cellular phenotypes (e.g., stimulating a macrophage to release beneficial growth factors but not to form foreign body giant cells). The peptides shown in Table 5 (SEQ ID NOS: 50-57) bind to cell surface receptors that are glycoproteins. There are other such peptide sequences that bind to cell-surface heparin-sulfate and chondroitin-sulfate containing proteoglycans, called as a family heparin-binding peptides. These can also be incorporated to confer cell adhesion via binding to such cell-surface components.

TABLE 5

Proteoglycan Binding Domain Sequences of Extracellular Matrix Proteins

| Protein | Sequence | SEQ ID NO: |
|---|---|---|
| χBBχBχ* | Consensus sequence | 50 |
| PRRARV | fibronectin | 51 |
| YEKPGSPPREVVPRPRPGV | fibronectin | 52 |
| RPSLAKKQRFRHRNRKGYRSQRGHSRGR | vitronectin | 53 |
| RIQNLLKITNLRIKFVK | laminin | 54 |
| K(βA)FAKLAARLYRKA | antithrombin III | 55 |
| KHKGRDVILKKDVR | neural cell adhesion molecule | 56 |
| YKKIIKKL | platelet factor 4 | 57 |

References for first five entries given in Massia, S. P., and Hubbell, J. A. J. Biol. Chem. 267: 10133-10141, 1992; Antithrombin III sequence from Tyler-Cross, R., et al., Protein Sci. 3: 620-627, 1994; Neural cell adhesion molecule sequence from Kallapur, S. G., and Akeson, R. A., J. Neurosci. Res. 33: 538-548, 1992; Platelet factor 4 sequence from Zucker, M. B., and Katz, I. R., Proc. Soc. Exp. Biol. Med. 198, 693-702, 1991.
*χ indicates a hydrophobic amino acid.
Basic amino acids are shown underlined.

It should be noted that the practical method for incorporation of the adhesion peptide by the method of the present invention is much easier than the state of the art (Pathak, supra). By such method as used in the prior art (taking the example of the formation of a Peptide-PEG-Acrylate), a heterobifunctional PEG must be synthesized, with an activated ester on one end and an acrylate on the other end. This must be grafted to the peptide, and purified. This agent is then useful for either incorporation by the method of this invention or by polymerization of the acrylate end groups, for example in a PEG diacrylate as taught by Hubbell et al. By contrast, the present method of peptide incorporation is much easier. The nucleophile (e.g., cysteine with a free thiol) containing peptide is simply mixed with the PEG diacrylate (or the multifunctional PEG conjugate unsaturated structure), is allowed to react for a short period of time, and then either the remainder of a different multinucleophile is added or the system is photopolymerized. There is no synthesis of a heterobifunctional agent, and there is no purification after coupling. This is possible due to the self-selectivity of the system.

Growth Factor Binding Peptides

A second sort of biofunctionality that is useful in biomaterials are structures that bind growth factors. These can be used in the controlled delivery and release of growth factors. An excellent example can be found for heparin-binding growth factors, which include aFGF, bFGF, VEGF, TGFβ, and BMP. It is straightforward to incorporate peptides that bind heparin (as described above, and further below). Heparin can be added to this mixture, along with the growth factor. Because of the self-selectivity of the system, chemical reaction with the heparin and the growth factor would not be expected to occur. Thus, if a heparin-binding peptide containing a single free thiol at a cysteine residue were mixed with heparin and a heparin-binding growth factor, and if these components were mixed with, for example, a PEG-triacrylate, and if this were mixed with a protease substrate peptide with two thiols by the incorporation of two cysteine residues (one each on both sides of the substrate domain), the following biomimetic biomaterial would result: the biomaterial would be degradable by cell-associated proteases, and the growth factor would be bound into the biomaterial by non-covalent binding to heparin, which is in turn non-covalently bound to the heparin-binding peptide, which is, in turn, covalently bound to the hydrogel biomaterial. Alternatively, one could functionalize heparin directly so that it contains a single strong nucleophile and is directly chemically bound into the polymer network. Another related way to sequester heparin-binding growth factors would be more directly through the use of covalently incorporated heparin mimics (e.g., peptides with negatively charged side chains) that directly bind growth factors.

Controlled Release of Covalently Bound Pharmaceutically Active Compounds

Methods and compounds have been developed for the covalent attachment of pharmaceutically active compounds to biomaterials and their subsequent release. Linkers are described that have qualities that facilitate the coupling to biomaterials and preferably promote the eventual release of the original, unmodified pharmaceutically active compound. The biomaterials or precursor components of biomaterials to which pharmaceutically active compounds can be attached are suitable for placement at many sites within the body of an animal.

The systems describe herein are similar to the Type IVb systems in which a free radical polymerizable group is added to a drug, with subsequent free radical polymerization of the drug alone or with other co-monomers to form a material (Baker, supra and Duncan et al., supra). However, the groups of the present invention can be polymerized by either conjugate addition reactions or free radical polymerization. As in other Type IVb systems, a linker molecule can be used to connect a drug to an active group on a polymer.

In contrast to the nucleophilic substitution reactions used by others to couple a drug to a polymer, the methods of the current invention involve a conjugate addition reaction between a pharmaceutically active compound or a modified pharmaceutically active compound and a conjugated unsaturated group on a polymer. Conjugate addition reactions, which have been described above, are a subset of nucleophilic addition reactions, and thus are chemically distinct from the nucleophilic substitution reaction used by others. In conjugate addition reactions, there is no leaving group as required for nucleophilic substitution reactions, and a nucleophile adds across a double or triple bond. The high self-selectivity of conjugated additions reactions compared to nucleophilic substitution reactions is advantageous for the application of this method to the in situ formation of biomaterials in the presence of sensitive biological molecules.

The process involves the coupling of a linker molecule to an alcohol or amine on the pharmaceutically active compound through an ester or amide bond, wherein the linker molecule then presents a chemical group useful in conjugate addition reactions. Following the coupling of the pharmaceutically active compound to a polymer through a conjugate addition reaction, a thioether or secondary amine is present on the linker molecule near the carbonyl ester or amide that attaches the linker to the pharmaceutically active compound. The half-life at physiologic temperature and pH of this ester or amide is much longer than the half-lives of many of the linkages previously described for drug delivery from materials, however, the half-life of this bond will be shorter than the half-life of a completely aliphatic ester or amide due to the thioether. These therapeutically relevant release rates are an important aspect of the invention, since most of the prodrugs that have been previously described have demonstrated half-lives at physiologic conditions on the order of hours, whereas many of the compounds of the present invention have bonds onto the pharmaceutically active moiety or between the pharmaceutically active moiety and the polymer that hydrolyze on the order of weeks or months. Such an improvement may allow the incorporation of higher amounts of pharmaceutically active compound within the biomaterials, and may lengthen the time over which the biomaterial releases the pharmaceutically active compound.

Pharmaceutically active compounds can contain a variety of chemical groups, some of which are nucleophilic and some of which are electrophilic. In terms of drug stability, highly reactive groups are typically undesirable, and thus highly reactive groups are rarely found on pharmaceutically active compounds. Many examples of pharmaceutically active compounds can be found that do not contain nucleophilic groups other than alcohols. The reactivity of these alcohol groups is generally so low that coupling the pharmaceutically active compound to a material is challenging. Long reaction times would be required, and any competing reactions would be very problematic because purification of a pharmaceutically active compound-polymer complex would be very difficult. The separation techniques that are commonly used in chemistry were developed for relatively small molecules and are not very effective with polymers due to their high molecular weight. The greater purity that can be obtained for a pharmaceutically active moiety coupled to a linker compared to a polymer coupled to a linker is important for the clinical use of precursor components or biomaterials made from these compounds since the remaining impurities could cause undesired side-effects in mammals. Thus, several advantages can be gained by converting a single alcohol on the pharmaceutically active compound to a thiol or amine using a linker. In the case of oligonucleotides or peptides, this may be quite simple, since the thiol containing group can be easily added during the synthesis of the molecule. In the case of organic molecules, this requires more effort, but is often feasible. Modifications to the synthesis of a particular pharmaceutically active compound, especially one that has already passed government regulatory approval, is highly undesirable. Preferably, any modification performed to couple a pharmaceutically active compound to a biomaterial is done in such a way that the original pharmaceutically active compound is eventually regenerated by the hydrolysis of the ester or amide bond onto the pharmaceutically active moiety. Because some pharmaceutically active compounds retain their therapeutic activity after modification of a reactive group, such as an alcohol or amine, biomaterials that release compounds with such modifications can also be therapeutically useful.

The current invention converts an alcohol or amine on the pharmaceutically active compound to a more reactive thiol or amine group. Because of the superior nucleophilicity of the thiol group as compared with an amine group and because amine groups are often found on pharmaceutically active compounds, a linker containing a thiol group is preferred over one containing an amine group. In some instances, however, the presence of an amine instead of a thiol in the linker may give a more desirable rate of release of the pharmaceutically active compound. The methods described herein include adding a linker molecule to the pharmaceutically active compound, rather than to the biomaterial or polymer. The chemical nature of this linker molecule can be quite diverse, but consists of the general structure $R_1$—COOH before reaction with the pharmaceutically active compound, where $R_1$ is an organic moiety that does not contain a substantially nucleophilic or electrophilic group. This carboxylic acid containing molecule is then condensed with an alcohol or amine from the pharmaceutically active compound. In one case, a poorly reactive sulfur or nitrogen atom is contained within the $R_1$ group, and by the use of suitable deprotection chemistries a free thiol or amine can then be generated. In another case, $R_1$ is CH2=CH—, which can be reacted with a second linker molecule of the structure $R_2$—SH or $R_2$—NH$_2$. A poorly reactive sulfur or nitrogen atom is included in $R_2$, and by the use of suitable deprotection chemistries a free thiol or amine can then be generated. The attachment of the linker molecule is then followed by extensive purification, which would not be possible if the pharmaceutically active compounds were directly attached to a biomaterial or polymer. Additionally, the attachment of such linkers can be incorporated into the overall synthesis of a pharmaceutically active compound, rather than occurring after the complete synthesis of the compound. Additionally, new pharmaceutically active compounds can be designed, based on the structures of existing pharmaceutically active compounds, that are more easily attached to a polymer using the methods described herein, but which have similar pharmacokinetics to the original compound.

Attachment of Pharmaceutically Active Compounds to Thiol- or Amine-containing Linkers In one method of the invention, a pharmaceutically active compound whose nucleophilic character consists of the presence of amines, alcohols, or weaker nucleophiles, is reacted so that the amine groups are protected against further reaction using standard techniques. An alcoholic group on the protected pharmaceutically active compound or a pharmaceutically active compound containing only alcoholic reactive groups is targeted for further reaction with a derivative of mercaptopropionic acid or mercaptoacetic acid in which the mercapto group is protected or aminopropionic acid or glycine in which the amine group is protected. An ester linkage is formed by condensing the carboxylic acid in the protected thiol or amine-containing compound acid with the alcohol on the pharmaceutically active compound. The protecting group on the amine or mercapto group and the protecting groups, if any, on the pharmaceutically active moiety are then removed using standard techniques. This product is then reacted with a water-soluble polymer containing conjugated unsaturated groups as described in more detail below. In a related method, a pharmaceutically active compound containing a free primary or secondary amine can be reacted as described above to form an amide-containing compound that can be attached to a polymer.

Attachment of Pharmaceutically Active Compounds to Acryloyl Derivatives

In another method, an acryloyl derivative, such as acrylic acid, is reacted with an alcohol on a pharmaceutically active compound, that may contain protected amine groups, to produce an ester. Alternatively, the acryloyl derivatives can be reacted with an amine on the pharmaceutical active compound to produce an amide. The resulting acrylate on the pharmaceutically active compound is then reacted with a linker molecule containing one free thiol or amine and one protected thiol or amine. The protecting group on the thiol or amine of the linker molecule can be removed, and this thiol or amine can then be reacted with a water-soluble polymer containing 2 or more conjugated unsaturated groups.

Roles Performed by the Linkers

An important aspect of the invention is that the thiol or amine groups in the linker provide a dual function. First, the groups allow a rapid and quantitative reaction with a polymer via a conjugate addition reaction, so that the pharmaceutically active compound can be coupled to the polymer. Second, the presence of a thioether near the ester or amide bond that attaches the pharmaceutically active compound to the linker enhances the rate of hydrolysis of the bond, relative to a simple aliphatic ester or amide. Typically, a completely aliphatic ester is expected to have a half-life of hydrolysis in buffered water at pH 7.4, 37° C. on the order of years, because of the hydrophobicity of the aliphatic chain. If an acrylate group is attached to polyethylene glycol via an ester, the increased access of water to the acrylate ester bond reduces the half-life in buffered water at pH 7.4, 37° C. to about 3 months. Similarly, if an acrylate group attached to a polyethylene glycol is reacted with a thiol-containing compound, the resulting thioether near the ester reduces the half-life of hydrolysis to approximately three weeks. The compounds of the invention having the formula D-O$_2$C—(CH$_2$)n-SH have a half-life of approximately 4 days when n is 1 and 18 days when n is 2. The corresponding amide containing compounds have a longer half-life, approximately 4 times longer than the esters, that is still clinically relevant. Additionally, it is known that a thiol attached to the alpha carbon relative to an ester bond has a half-life at pH 7.4, 37° C. of approximately four days (Nicolaou et al., U.S. Pat. No. 5,817,840). Compounds having the formula D-O$_2$C—(CH$_2$)—NH have a half-life of about 4 months. In terms of the delivery of pharmaceutically active compounds, the preferred dosing schedule for the administration to a mammal of precursor components of a biomaterial or a biomaterial is not more than once a day, preferably about once per week to once per month. Thus, a half-life of hydrolysis of between 1 hour and 1 year, preferably between 1 day and 9 months, more preferably between 2 days and 6 months, and most preferably between 4 days and 3 weeks is desirable for clinical applications.

Additionally, a highly water-soluble linker can facilitate the reaction of the modified pharmaceutically active compound with a polymer by increasing the solubility of the modified compound. If the linker is hydrophilic, the linker may increase the rate of release of the pharmaceutically active compound by exposing the hydrolyzable linkage to water. If the linker is hydrophobic, the linkage may be removed from the water environment, and the hydrolysis may be slower. If the linker contains a nucleophilic group such as an amine, then the nucleophile may react with the ester or amide bond that couples the pharmaceutically active compound to the polymer, and thus may speed the release of the original, unmodified pharmaceutically active compound. Additionally, the linker may comprise one or more amino acids, an enzymatically degradable peptide, an adhesion site, a growth factor binding site, a protease site, a hydrocarbon moiety, or a peptide sequence for targeting to a desired site.

Modified Pharmaceutically Active Compounds Containing a Free Thiol or Amine

In addition to naturally occurring or synthesized organic molecules, therapeutic DNA, RNA, peptides, or proteins can be covalently bound within the biomaterial as described above. Additionally, the DNA, RNA, peptide, or protein can be modified so that is has only a single free thiol, which is then reacted directly with a water-soluble polymer containing multiple conjugated unsaturated groups and the product is cross-linked. In this case, the original pharmaceutically active compounds is not regenerated, however, the modification of DNA, RNA, peptide, and protein therapeutics is much more common and acceptable than the modification of traditional pharmaceuticals. The modification to the DNA, RNA, peptide, or protein usually does not affect the activity of the molecule if the modification is made at a site on the molecule that is distant from the active site.

In the case of peptides or oligonucleotides, a thiol or amine can be added at a site distant from the active site of the molecule, by the inclusion of the amino acid cysteine or by the use of a derivatized oligonucleotide. In these cases, the thiol or amine containing molecule can be directly reacted with an acrylate group on the polymer. The molecule that is released due to hydrolysis is not the original molecule, but contains a thiol or amine that is modified with propionic acid. Since portions of therapeutic peptides and oligonucleotides that are distant from the active site can be varied greatly without a loss in activity, these compounds usually retain their therapeutic activity.

Coupling of Pharmaceutically Active Compounds to a Polymer and Subsequent Cross-linking The free thiol or amine that is added to, or originally present in, the pharmaceutically active compound is then used to couple the pharmaceutically active compound to a polymer. Biomaterials are often formed from hydrophobic polymers, but these are not desirable here since the release of the covalently attached pharmaceutically active compound depends on the presence of water around the pharmaceutically active compound. Thus, the pharmaceutically active compound can be attached to water-soluble polymers or water-swellable polymers. Water-soluble polymers can be formed into a material in a variety of ways, through the formation of covalent or physical cross-links. Covalent cross-links can be established by adding groups to the polymers that are capable of free-radical polymerization (Hubbell et al., U.S. Pat. No. 5,410,016), nucleophilic substitution (Zhao et al., Polymer Preprints 38(1):526-527 1997), and other chemical methods, including conjugate addition reactions.

The attachment of the pharmaceutically active compound to the water-soluble or water-swellable polymer must be performed in a manner that is complementary with the subsequent cross-linking of the water-soluble polymer to form a biomaterial. To accomplish this coupling of pharmaceutically active compound to a polymer and the subsequent cross-linking of the polymer, others have used bifunctional water-soluble polymers containing one class of chemical groups for the attachment of the pharmaceutically active compound and another class of chemical groups for the cross-linking reaction. As would be expected, bifunctional polymers are more expensive and more difficult to produce than monofunctional polymers. Here, monofunctional refers to the fact that only one type of functional group is present on the polymer, not that each polymer molecule contains only a single functional group. In the present invention, monofunctional polymers having a single type of functional group are used for two different types of reactions. One type of reaction is used for the attachment of pharmaceutically active compounds, and the other type of reaction is used for cross-linking. The type of functional group that is useful in this context is a group that is an acceptor in a conjugate addition reaction. These groups include acrylates, methacrylates, acrylamides, methacrylamides, acrylonitrile derivatives, quinones, derivative thereof, and other groups with conjugated double bonds. Such reactions between a thiol and an acrylate proceed rapidly in buffered water at near neutral pH (with a half-life on the order of minutes). Thus, the reaction to couple the pharmaceutically active compound to the polymer can occur under very mild conditions that will not harm the pharmaceutically active compound. The reaction may also be performed in an organic solvent or a mixture of water and a polar organic solvent.

In buffered water at near neutral pH, the reaction between the thiol and acrylate occurs much faster than the reaction between two thiols (to form a disulfide bond) or the reaction between two acrylates (to form a polymer, assuming an absence of free radical initiators). Preferably, the reaction between the thiol and the acrylate occurs 10, more preferably 100, and most preferably 1000 times faster than the reaction between two of the thiols. The reaction between the thiol and the acrylate is also preferably 100, more preferably 1000, and most preferably 10,000 times faster than the reaction between two of the acrylates in the absence of free radical initiators. For the corresponding reaction between an amine and the acrylate, the reaction rate is preferably 10, more preferably 100, and most preferably 1,000 times faster the reaction between two of the acrylates in the absence of free radical initiators.

The subsequent cross-linking reaction can generally occur by two main routes, utilizing either free-radical polymerization (Lau et al., *Bioorg. Med. Chem.* 3: 1305-1312, 1995) or conjugate addition reactions. The conjugated unsaturated groups of the present invention that are reacted with good nucleophiles via conjugate addition reactions can generally also be polymerized by free-radical mechanisms. Thus, as long at least one conjugated unsaturated group remains on the polymer following the coupling of the pharmaceutically active compound, then that polymer can be incorporated into a biomaterial by free-radical mechanisms. The presence of at least one unreacted unsaturated group on the polymer is assured by keeping the number of unsaturated groups in excess compared to the thiol or amine groups present in, or coupled to, the pharmaceutically active moiety. The second route to cross-link these materials involves reacting the remaining conjugated unsaturated groups on the polymer coupled to a pharmaceutically active moiety with cross-linker molecules containing 2 or more nucleophiles, such as the peptide GCNNRGDNNCG (SEQ ID NO: 75) that increases cell adhesion to basement membranes. The cross-linking to form a material then occurs through another conjugate addition reaction.

Such cross-linking reactions as described above can occur in the presence of living cells and tissues (Lau et al., supra). Thus, the drug-containing material can be placed or cross-linked at practically any site within the body. The material serves as a depot for the delivery of therapeutic agents at the desired site of activity. A useful example consists of the delivery of a therapeutic agent from a biomaterial placed or polymerized in the tissue containing a malignant growth. Alternatively, a malignant growth can be removed from a tissue surgically, and a biomaterial containing a covalently bound pharmaceutically active moiety can be placed or polymerized near the site of removal of the malignant growth. The release of the original or modified pharmaceutically active compound from this biomaterial may prevent the seeding of tumor cells that are ejected from the tumor during its removal or may prevent the further growth of malignant cells that could not be removed during the surgery.

While the preferred embodiment of the invention is the use of conjugate addition reactions to attach a polymer to a thiol or amine group coupled to a pharmaceutically active compound, a nucleophilic substitution reaction can be used to react the thiol or amine group with the polymer. This embodiment uses a linker to enhance the reaction of the pharmaceutically active compound with the polymer to allow the release of the original pharmaceutically active compound over a period of time due to hydrolysis of the linker.

There now follow particular examples that describe the preparation of compositions of the invention, and the methods of the invention. These examples are provided for the purpose of illustrating the invention, and should not be construed as limiting.

EXAMPLE 1

Preparation of Basic Reagents

Acrylation of Poly(Ethylene Glycol) Diol

Polyethylene glycol, mol. wt. 8000 (50 g, 6.25 mmol, 12.5 mmol hydroxyl groups, Aldrich, Milwaukee, Wis., USA) was added to toluene (500 ml) and dried by azeotropic distillation. The mixture was cooled to 0° C. and 100 ml of anhydrous dichloromethane (Aldrich) was added. Triethylamine (2.61 ml, 18.75 mmol, 1.5 eq. based on hydroxy groups, Aldrich) was added, followed by dropwise addition of acryloyl chloride (2.03 ml, 18.75 mmol, 1.5 eq., Aldrich). The reaction was kept under Ar overnight in the dark. The product was filtered and then recovered by precipitation in hexane with stirring. The product was redissolved in 75 ml of dichloromethane and precipitated again in hexane with stirring. The product was dried overnight under vacuum. The product was dissolved in 500 ml of water with 25 g NaCl, and the pH was adjusted to pH 6. The solution was extracted with dichloromethane (Aldrich) 3 times (the first extraction with dichloromethane should not be shaken vigorously to avoid the formation of an emulsion). The dichloromethane fractions are combined and added to stirring hexane. The product is recovered by filtration and dried under vacuum overnight. By 1H-NMR, 80% of alcohols on the polyethylene glycol are acrylated (product is referred to as polyethylene glycol diacrylate)

Acrylation of Poly(Ethylene Glycol) Triol

PEG-triacrylate (PEG-3A) is a three-armed PEG with glycerol core. Molecular weight notations (PEG-2500-3A, PEG-3500-3A) refer to total average molecular weight and not to the molecular weight of a single arm. The acrylation was carried out using exactly the same molar ratios of reactants as described for the PEG diol.

Crotonylation and Dimethylacrylation of Poly(Ethylene Glycol) Diol

Crotonoyl PEG-8000 (PEG-8000-2C) (crotonyl, —OOC—CH═CHCH$_3$) and dimethacryloyl PEG-8000 (PEG-8000-2DMA) (dimethacryloyl, —OOC—CH═C(CH$_3$)$_2$) were synthesized simultaneously in side by side reactions. 27 g PEG-8000 (3.375 mmol, 6.75 mmol hydroxyl groups; Aldrich) was dissolved in benzene and azeotropically distilled until the distillate appeared clear. The PEG-benzene solution was allowed to cool to room temperature. Then 100 ml of the solution was anhydrously transferred to a separate round bottom flask. Triethylamine (1.1 ml to the 100 ml sample and 1.7 ml to the larger (150 ml) sample, 3 equivalents based on hydroxyl groups; Aldrich) was added to each flask. Crotonoyl-Cl (1.2 ml, 3 equivalents based on hydroxyl groups; Fluka) was added dropwise to the 150 ml sample. Dimethacryloyl-Cl (0.9 ml, 3 equivalents based on hydroxyl groups; Fluka) was added dropwise to the 100 ml sample. The reactions were run 20 hours in the dark. The solutions were filtered through paper and precipitated in hexane. Both precipitates were dried in vacuo. The degrees of modification were determined by 1H NMR to be 85% for the PEG-8000-2C and 89% for the PEG-8000-2DMA (by degree of esterification).

Preparation of Bis(Benzoquinones) PEG

Step A) Preparation of Bis-carboxyl PEG 17 g (5 mmol) of 3400 PEG diol are dissolved in 500 ml of toluene and dried by azeotropic distillation; 15 ml of 1M TIE solution of potassium term-but oxide (15 mmol) are added and the reaction mixture is refluxed for 10 minutes, then cooled to room temperature. 5.4 ml (50 mmol) of ethyl 2-bromoacetate are then added; the solution is stirred for 24 hours at 40° C. then filtered to remove KBr, concentrated at the rotary evaporator and precipitated in cold diethyl ether. The solid is then dissolved in 250 ml of 0.2 N NaOH (the pH is kept at 12 by dropwise addition of 4 N NaOH); the solution is stirred for 12 hours, and after the pH drops to 4 by dropwise addition of concentrated HCl, is extracted with dichloromethane; the organic phase is dried on sodium sulfate and precipitated in cold diethyl ether. The degree of modification is determined by 1H-NMR.

Step B) Preparation of bis(carboxyl 2,5-dimethoxyaniline) PEG 10 g (2.8 mmol, 5.7 meq) of 3400 bis-carboxyl PEG are dissolved in 200 ml of THF together with 2.0 g (6 mmol) of 2,5-dimethoxyaniline (recrystallized three times from hexane); 0.73 g (5.8 mmol) of diisopropyl carbodiimide are then added and the solution is stirred for 24 hours at room temperature. The precipitated diisopropyl urea is filtered off, the THF evaporated at the rotary evaporator; the polymer is then redissolved in toluene, the solution is filtered and then precipitated in cold diethyl ether. The procedure is repeated twice. The degree of modification is determined by 1H-NMR.

Step C) Preparation of Bis(Carbonyl 2,5-hydroxyanilide) PEG 5 g (1.4 mmol, 5.2 meq) of 3400 bis(carboxyl 2,5-dimethoxyaniline) PEG are dissolved in 50 ml of dry dichloromethane in dry nitrogen atmosphere; 1.2 g (6 mmol, 0.82 ml) of iodotrimethylsilane are then added and the solution is stirred for 24 hours at room temperature. The dichloromethane solution is then washed with water till neutrality, dried over sodium sulfate, concentrated to small volume and precipitated in hexane. The reaction yield is determined by 1H-NMR.

Step D) Preparation of bis(carboxamide 2,5-benzoquinones) PEG 5 g (1.4 mmol, 5.6 meq) of 3400 bis(carbonyl 2,5-hydroxyanilide) PEG are dissolved in 50 ml of ethanol and 1.2 g (7.4 mmol) of iron (III) chloride. The solution is stirred for 24 hours at room temperature, then 150 ml of dichloromethane and 150 ml of water are added and two phases separate; the dichloromethane phase is washed three time with water, then concentrated and precipitated in cold diethyl ether. The reaction yield is determined by 1H-NMR.

Preparation of α,ω-Bis(Benzoquinones) Poly(Lactic Acid)-PEG-poly(Lactic Acid) Block Copolymer (Example with 2.5 Monomeric Units of Lactic Acid Per PEG End)

Step A) Preparation of Poly(Lactic Acid)-PEG-Poly(Lactic Acid) Block Copolymer 17 g (5 mmol) of dry 3400 PEG diol, 3.60 g (0.025 mol) of dl lactide and 15 ml of stannous octanoate are mixed together under dry nitrogen atmosphere. The reaction mixture is stirred at 200° C. for 2 hours and at 160° C. for 2 hours and subsequently cooled to room temperature. The resulting solid is dissolved in dichloromethane and precipitated in cold diethyl ether.

Steps B to E)

Steps B to E are analogous to the steps A to D in the preparation of bis(benzoquinones) PEG.

Preparation of poly(ethylene-co-vinyl alcohol-co-2-oxyvinyl-(2',5'-benzoquinones)acetamide)

Step A to D) Preparations of poly(ethylene-co-vinyl Alcohol-co-2-oxyvinyl-acetic acid)

These preparations are analogous to the STEPS A to D in the preparation of bis(benzoquinones) PEG.

Preparation of bis(4-vinylpyridyl) PEG 10 g (2.7 mmol) of freshly prepared 3400 PEG triflate were reacted for 24 hours at 0° C. with 0.75 g (8 mmol) of 4-vinyl pyridine in 30 ml of dry NMP. The solution was precipitated in cold diethyl ether, the solid redissolved in dichloromethane and precipitated again in cold diethyl ether.

Peptide Synthesis

Peptides were synthesized on a Perseptive Biosystems (Framingham, Mass., USA) Pioneer peptide synthesizer using the standard Fmoc protection scheme. Peptides were cleaved from the resin using 8.8 ml trifluoroacetic acid (Perseptive Biosystems), 0.5 ml of water 0.5 ml phenol (Aldrich), and 0.2 ml triisopropylsilane (Aldrich) per gram of resin, for 2 hr at room temperature. The solution was precipitated in ether, and product recovered by filtration, and dried under vacuum. Peptides were purified by C18 chromatography, and fractions containing product were identified by MALDI-TOF mass spectrometry. Peptides were stored under Ar at −20° C.

Prior to application, cysteine-containing peptides were handled wet in acidic solutions and/or degassed solutions, or dry under vacuum or under argon as much as possible to prevent oxidation.

EXAMPLE 2

Gel Formation by Conjugate Addition Reactions

Gels Formed by Conjugate Addition with a Low Molecular Weight Tri-thiol and a PEG-linked Unsaturation: Trimethylolpropane Tris(3-mercaptopropionate) and PEG Diacrylate 50 mg PEG-8000-2A was dissolved at 0.1 g/ml in 500 microliters of 4:1 50 mM bicarbonate buffer (pH 8.4): acetonitrile. 1.1 microliters of trimethylolpropane tris(3-mercaptopropionate) (1.25 equivalents based on acrylates) were added and the solution mixed by vortexing. The trimethylolpropane tris(3-mercaptopropionate) was not perfectly miscible in the solution but formed a suspension of small droplets in the aqueous phase. The material did not gel in two hours but was let to sit overnight. At approximately 12 hours after addition of the trimethylolpropane tris(3-mercaptopropionate), a solid cross-linked material had formed. Water was added to the material, which swelled with the water but did not dissolve (time scale: weeks before gel finally discarded due to contamination).

Likewise, a gel of higher concentration of PEG and with stronger mechanical properties was formed by first dissolving 0.2 g PEG-8000-2A in 750 microliters of unbuffered water and 250 microliters acetone. 4.4 microliters of trimethylolpropane tris(3-mercaptopropionate) (1.25 equivalents based on acrylate groups) were added. While trimethylolpropane tris(3-mercaptopropionate) is soluble in acetone at these concentrations (4.4 microliters trimethylolpropane tris(3-mercaptopropionate)/250 microliters acetone), it still formed an visibly insoluble suspension with the PEG solution upon vortexing. After 2-4 hours, a highly cross-linked water insoluble material had formed.

Gels Formed by Conjugate Addition with a Peptide-linked Nucleophile and a PEG-linked Conjugated Unsaturation The peptide GCYKNRDCG (SEQ ID NO: 58) was designed to be sensitive to hydrolysis by the enzyme plasmin. to contain more than one thiol (cysteine) for addition reaction with conjugated unsaturated groups, and to be very water soluble. The peptide was synthesized according to the methods described above. The peptide was extremely water soluble, up to at least 120 mg/ml.

Gels were formed from PEG-2500-3A and GCYKNRDCG (SEQ ID NO: 58) as well as from PEG-3500-3A and GCYKNRDCG (SEQ ID NO: 58). Gels have been formed at three ratios of acrylates to sulfhydryls (1:1, 1.1:1, and 1.25:1). Gels were formed in 10 mM phosphate buffered saline with triethanolamine to adjust the pH to 8.0-9.0 as tested by paper pH strips (gel formation reactions were performed at 50 microliter and smaller scales). Gels have been made by: predissolving the peptide and then adding peptide solution to PEG-3A; by predissolving the PEG-3A and adding its solution to the peptide; and by predissolving both solutions and then mixing them in appropriate ratios.

The following protocol has been used for gel formation at the 40 microliter scale. The amount of PEG-2500-3A weighed into an Eppendorf varies due to the sticky qualities of the material that make is somewhat difficult to maneuver. However, the buffer volume added to the PEG-2500-3A is always adjusted to give the same final concentration on a mass/volume basis.

2.5 mg of GCYKNRDCG (SEQ ID NO: 58) were weighed into an Eppendorf tube. 7.0 mg of PEG-2500-3A were weighed into a separate Eppendorf tube. 62 microliters of phosphate buffered saline (PBS).TEA (10 mM PBS with 13 microliters of triethanolamine/ml) were added to the PEG-2500-3A to give a solution of 4.5 mg/40 microliters. The PEG solution was allowed to sit until the PEG-3A had dissolved (less than five minutes). 40 microliters of the PEG-3A solution were added to the peptide, which dissolved extremely rapidly. The pipet tip used for the transfer was used to stir the mixture for approximately 3 seconds. A 1 microliter sample was withdrawn to test the pH by a paper strip (pH range 1-11). The pH was approximately 8.0. After 20-30 minutes, a gel had formed.

Controlling the Rate of Gelation by Modulating Charge Near a Nucleophile (e.g., Thiol)

Two collagenase (MMP-1) sensitive peptides were synthesized: GCDDGPQGIWGQDDCG (SEQ ID NO: 59) and GCRDGPQGIWGQDRCG (SEQ ID NO: 60) using standard Fmoc techniques described in Example 1. In one peptide, the thiol (in cysteine, C) was close to a residue bearing negative charge (aspartic acid, D) when near neutral pH, the pH of interest. In the other peptide, the thiol was near a residue bearing positive charge (arginine, R) when close to neutral pH. Each peptide was reacted separately with acrylate containing polymers of PEG at pH 8. The rate of conjugate addition was followed by the consumption of thiols by using DTNB, Ellman's reagent. Results are shown in FIG. 1. The exchange of D->R (negative charge->positive charge) next to the thiol increased the rate of reaction such that the half life of thiol consumption during gel formation was decreased almost 3 fold. This was accomplished by design in order to increase the likelihood that the thiol exists in the S-form which participates in the conjugate addition and thus to increase the rate of reaction and gelation.

Swelling (Water Content) of Gels Made by Conjugate Addition Gels were made with 0.1 g/ml, 0.15 g/ml, and 0.2 g/ml PEG-2500-3A at a 20 microliter scale. The gels contained 1.1 acrylates per sulfhydryl in the peptide (nucleophile) component, GCYKNRDCG (SEQ ID NO: 58). For gel formation, PBS buffers were adjusted to account for added acidity of additional peptide in higher concentration gels and to give reactions at pH 8.0-8.5. Gels were made in quadruplicate.

TABLE 6

Conjugate addition gels for swelling studies

| | PEG-2500-3A (mg) | GCYKNRDCG (mg) | Triethanolamine (µl/ml) | % water in swollen gel |
|---|---|---|---|---|
| 10% | 2.0 | 1.1 | 13.0 | 96.5% |
| 15% | 3.0 | 1.7 | 20.1 | 95.8% |
| 20% | 4.0 | 2.2 | 26.0 | 94.8% |

Gels were swollen in 10 µM PBS, pH 7.3 for 48 hours before the first wet weight measurements were made. Gels were weighed wet four times over three consecutive days with no significant increase in wet masses over this time. Then the gels were soaked in deionized water, with exchanges of the solution phase, for four days after which time the gels were lyophilized in order to obtain dry masses. Water contents based on the maximum possible dry masses (due to variability in actual dry masses) are all approximately 95% by mass of the swollen gels.

Gels Formed by Mixing Two Powder Components

Material precursors may also be delivered to tissues in the dry state. For example, PEG dithiol can be formulated as a powder, PEG tetraacrylate can be formulated as a powder, one or the other but preferably both components containing buffer components such that when the two powder components are mixed and dissolved in water, saline or physiological fluids a solution forms at a pH such that reaction of the two precursor components occurs, e.g. pH 8. These powder components may be sprayed upon a tissue surface, either along with an aqueous stream or without one. In the case that the powders are sprayed with an aqueous stream or without one. In the case that the powders are sprayed with an aqueous stream, the polymer components dissolve in the aqueous steam, along with the layer of biological fluids on the tissue surface, and then react to form the final biomaterial implant. In the case of application of the powder components to the tissue surface, the polymeric precursors and the buffer components dissolve in the biological fluids and form a precursor solution, capable of reaction to form the final biomaterial implant. In the case where the biological fluids provide the moisture for dissolution of the polymeric precursor components, the concentration of the polymeric precursor components may be high, resulting in a strong biomaterial implant and good adhesion to the tissue. In the application of the powder streams, the powders may be mixed together and then applied as a single powder mixture to the moist tissue surface, or they may be mixed in a spray from two components. The powder components may be formed by methods know to those skilled in the art of powder technology, such as precipitation, grinding, milling, lyophilization, spray drying, and so forth. Small particles will lead to more effective and rapid dissolution, either in an aqueous stream or in moisture at the tissue surface. The two polymeric precursor components should be mixed together at a ratio such that the thiol components and the acrylate components are approximately equi-equivalent on a mole of thiol per mole of acrylate basis. Furthermore, the nature of the biomaterial implant may be controlled by adding other agents to the precursor powders, such as particles that are slow to dissolve in aqueous solution or gas formers, both of which will lead to the formation of pores within the material implant after curing.

EXAMPLE 3

General Protocols for Immobilizing Peptides and Testing Activity with Cells in Culture Peptide Immobilization in Gels in which the Peptide is Immobilized by Conjugate Addition and the Gel is Formed by Conjugate Addition 13.9 mg PEG-2500-3A was dissolved in 69.5 microliters (5.0 mg/25 microliters) of PBS·TEA (10 mM PBS containing 13 microliters of triethanolamine/ml) containing GCGYGRGDSPG (SEQ ID NO: 61) at a concentration of 3.2 mg GCGYGRGDSPG (SEQ ID NO: 61)/ml. 7.0 mg GCYKNRDCG (SEQ ID NO: 58) was dissolved in 65 microliters of PBS.TEA (2.7 mg/25 microliter). The GCYKNRDCG (SEQ ID NO: 58) was filtered through a 0.22 micron filter. After 9 minutes of reaction time, the PEG-2500-3A/GCGYGRGDSPG (SEQ ID NO: 61) solution was separately filtered through a 0.22 micron filter. As soon as the filtrations were complete, equivolumes (25 microliters) of the two solutions were added to wells of a Corning flat-bottomed tissue culture treated polystyrene 96 well plates. As the second of the two precursor solutions was added, the pipet tip was used to stir the mixture for 2-3 seconds. Then the gels were allowed to set at 37° C.

Cell-resistance of Gels Made by Conjugate Addition Lacking Incorporated Adhesion Peptides Conjugate addition gels were made with 0.1 g/ml PEG-2500-3A and 1.1 acrylates per sulfhydryl in GCYKNRDCG (SEQ ID NO: 58). The gels were swollen for 24 hours in Dulbecco's modified Eagle's medium (some in serum-free conditions and some in 10% fetal bovine serum) containing 1% antibiotic and antimycotic agents. Human foreskin fibroblasts (passage 7; passaged with trypsin/EDTA) were seeded onto the gels. From time points two hours to 48 hours, the cells remained round and did not spread. The cells became increasingly clumped together. The cellular behavior was independent of serum in the medium. Control cells seeded on tissue culture treated polystyrene spread normally.

Cell Interaction with Gels Made by Conjugate Addition Containing Incorporated Adhesion Peptides Conjugate addition gels were made with PEG-2500-3A. GCYKNRDCG (SEQ ID NO: 58), and an RGD-containing peptide (GCGYGRGDSPG (SEQ ID NO: 61)) incorporated in a pendant fashion. The gels were made with 0.1 g PEG-2500-3A/ml and 1.1 acrylates per sulfhydryl in GCYKN-RDCG (SEQ ID NO: 58). The gels were swollen for more than 36 hours in Dulbecco's modified Eagle's medium (some in serum-free conditions and some in 10% fetal bovine serum) containing 1% antibiotic and antimycotic agents. When the RGD peptide was incorporated on one of every 12 acrylates of the PEG-2500-3A, human foreskin fibroblasts (passage 8; passaged by trypsin/EDTA) adhered to the gels (both those swollen in serum-free conditions and those in serum-containing medium). At 6 hours post-seeding, the cells were uniformly distributed over the gel surface, and approximately 50% of the seeded cells were spread (in both medium conditions).

Cell Interactions with the Polyethylene Glycol Networks

Cell interactions with the polyethylene glycol networks were tested by seeding human cells onto the gels using standard tissue culture methods. Human foreskin fibroblasts or human umbilical vein endothelial cells were purchased from Clonetics (San Diego, Calif., USA). Fibroblasts were cultured in Dulbecco's Modified Eagles Medium containing 10% fetal bovine serum and 1% antibiotics (all from GIBCO BRL, Grand Island, N.Y., USA) at 37° C. and 5% $CO_2$. Endothelial cells were cultured in M199 media with 10% fetal bovine serum and 1% antibiotics (all from GIBCO BRL). Per 50 ml of media were added 100 µg/ml heparin (Sigma, St. Louis, Mo., USA) and 3 mg of Endothelial cell growth supplement (Becton Dickinson Labware, Bedford, Mass., USA). Cells were removed from culture substrates using Trypsin/EDTA (GIBCO BRL), centrifuged (500 g for 5 min for fibroblasts, 250 g for 5 min for endothelial cells), and resuspended in the normal cell culture media before seeding onto polyethylene glycol gels.

EXAMPLE 4

Chemical Analysis of Reaction Products

Reaction Kinetics Measured with Ellman's Reagent

Ellman's reagent was used to measure the concentration of thiols in a solution. The assay utilized a solution of 40 mg Dinitrobisthiol nitrobenzene (Sigma) in 10 ml of 0.1 M phosphate buffer pH 8 (Ellman's reagent). A solution was tested for the presence of thiols by the addition of the solution to 3 ml of the phosphate buffer. Ellman's reagent (100 µl) was added and mixed. After 15 min. the absorbance of the solution was measured 412 nm. A molar absorption coefficient of 14150 was assumed.

Figure 2:
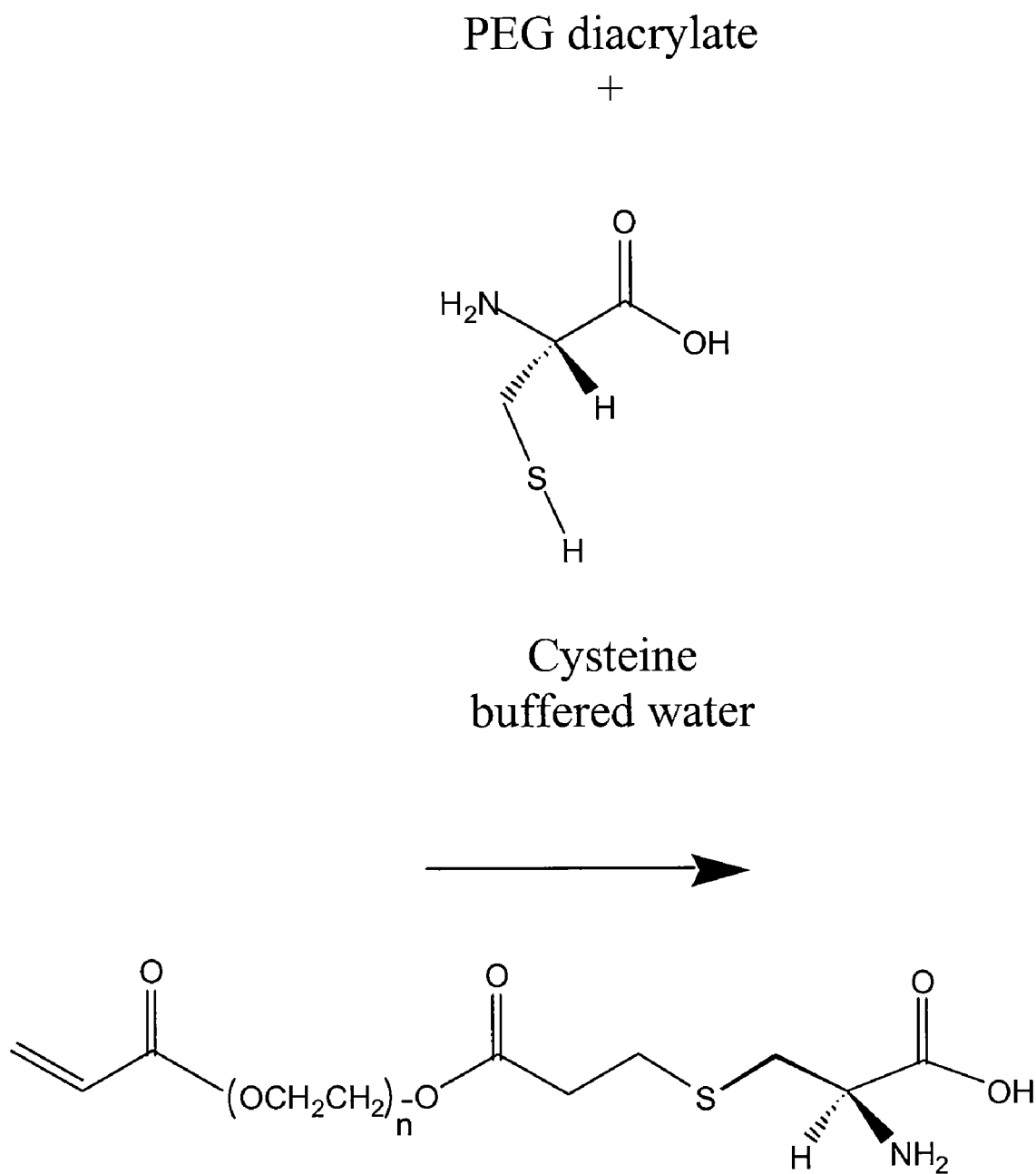
FIG. 2 is a schematic representation of a conjugate addition reaction, used as a model to study kinetics of a thiol (on cysteine) addition to the acrylate on PEG diacrylate.

Using the amino acid cysteine, Ellman's reagent revealed no detectable disulfide bond formation at pH 10 within 30 min at room temperature. If cysteine were added to an excess of PEG diacrylate, mol. wt. 8000, at the same conditions, the concentration of thiols dropped to 0.2% of the original value within seconds, and did not decrease further out to 30 min. demonstrating the rapid disappearance of thiols in the presence of PEG diacrylate. The conjugate addition reaction between PEG diacrylate and the amino acid cysteine is shown in FIG. 2.

Figure 3:
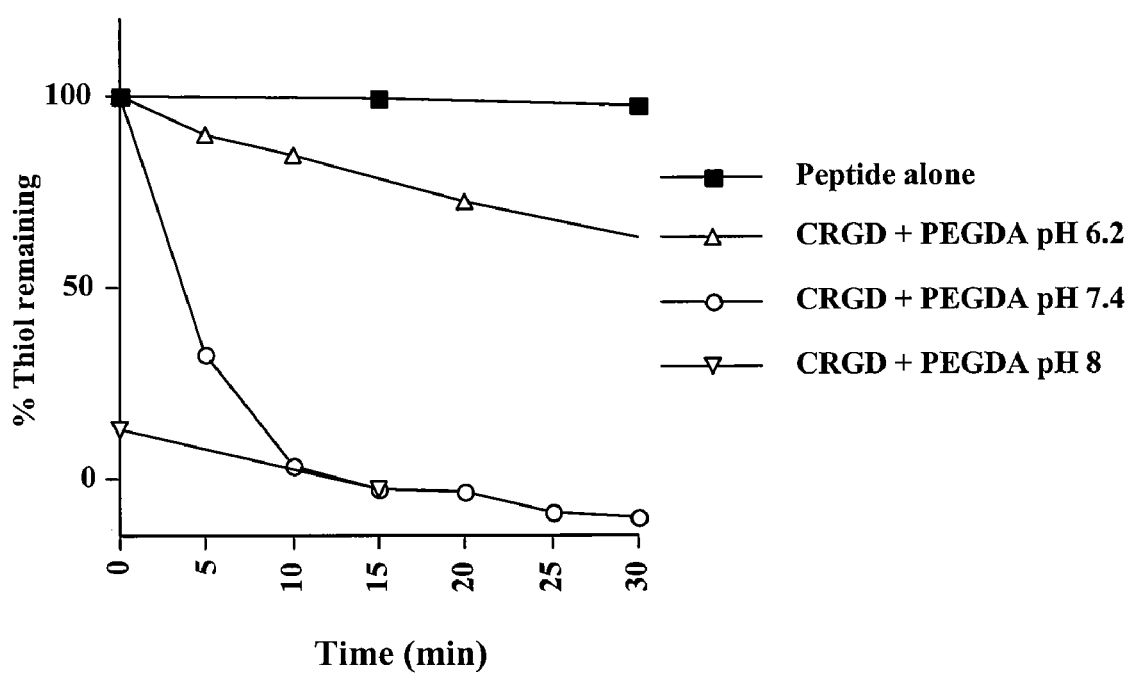
FIG. 3 is a graph showing the effect of pH on the addition reaction between a thiol (on cysteine) and PEG diacrylate.

The peptide with the amino acid sequence Ac-GCGYGRGDSP-$NH_2$ (SEQ ID NO: 62) was tested similarly. PEG diacrylate was dissolved in the phosphate buffer at pH 8 at a concentration of 25 µmol in 1 ml. The peptide (1 µmol) was added to the PEG diacrylate solution, and the disappearance of thiols was monitored using Ellman's reagent (see FIG. 3). The reaction was performed at different pH, and additionally, the formation of disulfide bonds was assessed by dissolving the peptide at the same concentrations but in the absence of PEG diacrylate. The half life for the reaction was about 3 min at pH 7.4, and only a few seconds at pH 8, at room temperature.

Another method to on-line follow the reaction between thiols and PEG diacrylate is monitoring the absorbance of the reaction mixture at 233 nm. At this wavelength, the absorbance is in principle due to four substances: the thiol components, the disulfide impurities in the thiol component, the acrylate and the product (the β-alkylthio propionic ester). The experiments were conducted in $10^{-2}$ M PBS buffer at various temperatures between 20° C. and 37° C.

Figure 4:
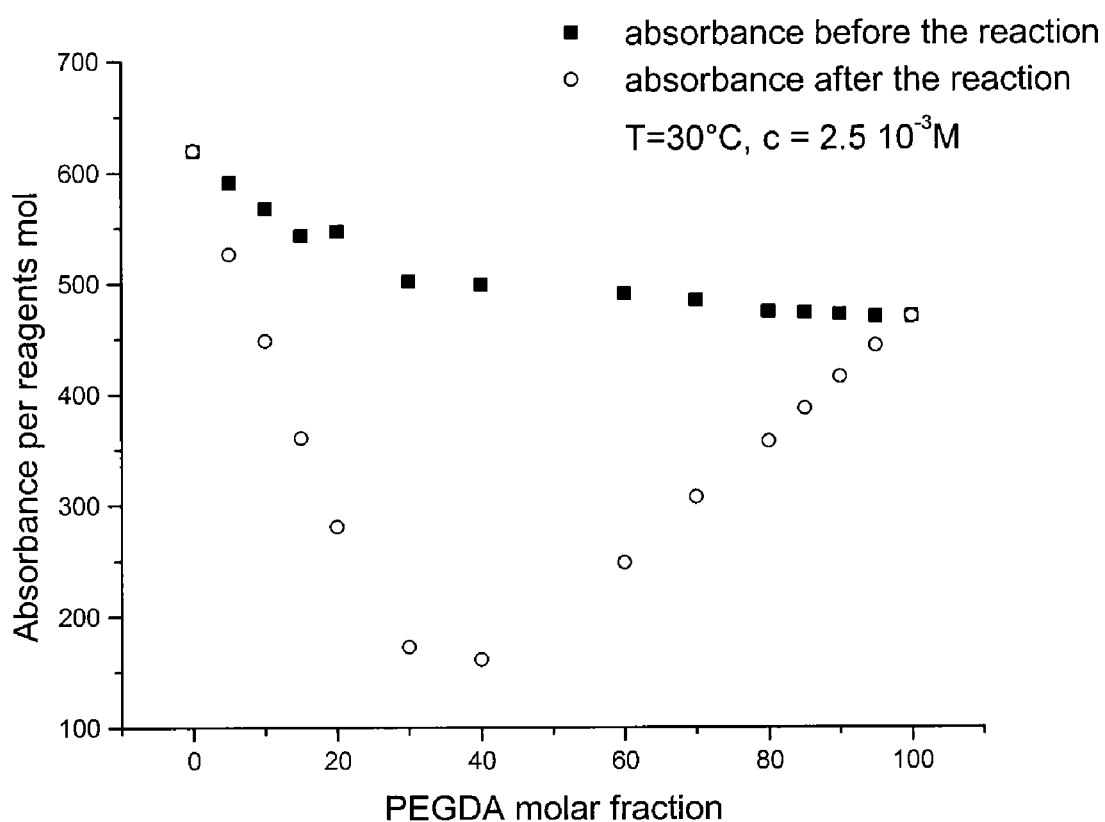
FIG. 4 is a graph of the effect of different PEGDA contents on the absorbance per mole of reagent, the average extinction coefficient (i.e., absorbance divided by the sum of the PEGDA and cysteine concentration; this sum is kept constant to $2.5 \times 10^{-3}$ M).

Performing experiments at several reactants ratios, but keeping constant the overall molar concentration of reactive groups (FIG. 4), the extinction coefficients of all the species can be calculated fitting the absorption values before and after the reaction. This procedure allowed to follow independently the time evolution of the concentration of reactants and products: PEGDA and cysteine showed a single exponential behavior, with same kinetic constants and this proofed the reaction to be first order for every reactant. Half-life times between 2 and 10 minutes, depending on temperature and reactants concentration have been recorded. In Table 7, the kinetic constants are listed.

TABLE 7

First-order kinetic constants for PEGDA-cysteine reaction at different PEGDA content, with a 2.5 × $10^{-3}$ M overall cumulative concentration

| PEGDA equivalent fraction | k ($min^{-1}$) |
|---|---|
| 0.18 | 0.14 |
| 0.33 | 0.12 |
| 0.46 | 0.06 |
| 0.57 | 0.10 |
| 0.75 | 0.28 |
| 0.82 | 0.32 |
| 0.88 | 0.42 |
| 0.95 | 0.59 |

Reaction of the PEG diacrylate with primary amines was also assessed. PEG diacrylate was mixed with a peptide with the amino acid sequence GDGSGYGRGDSPG (SEQ ID NO: 63), which contains only one primary amine at the amine terminus of the peptide. The presence of amines was measured using the fluorescamine assay. Fluorescamine (Sigma) was dissolved in dry acetone at 1.5 mg/ml. The peptide (1 mg) was added to 100 µl of 0.1 M phosphate buffer at pH 8. PEG diacrylate, mol. wt. 8000 (100 mg), was dissolved to 900 µl in 0.1 M phosphate buffer, pH 8 and mixed with the peptide solution. Samples were taken from the reaction and added to 100 µl of 1.5 mg fluorescamine in dry acetone, and raised to 1 ml with 50 mM borate buffer at pH 9.

The fluorescence intensity was measured using a spectrofluorimeter, and concentrations calculated by comparison with a standard curve produced using the amino acid glycine. The half life for the reaction of the amine with an acrylate was about 90 min at pH 8 and 37° C.

Production of PEG-peptide Adducts Assessed Using Size Exclusion Chromatography

Aqueous size exclusion chromatography was performed using a Shodex OHpak SB-803 column (Showa Denko, Tokyo, Japan), using UV detection, measuring absorbance from 200-400 nm. The eluent was phosphate buffered saline (10 mM sodium phosphate, 140 mM NaCl, pH 7.4). PEG diacrylate has maximum absorbance at 205 mu, whereas the peptide used, GCGYGRGDS (SEQ ID NO: 64) has absorbance maxima at 220 and 270 nm, due to the presence of amide bonds, and a tyrosine. PEG diacrylate was dissolved in 0.1 M phosphate buffer at pH 8 at a concentration of 25 µmol in 1 ml. A sample of the solution was separated using size exclusion chromatography, and the polyethylene glycol eluted as a single peak with an absorbance maximum at 205 nm, and no absorbance at 220 or 270 nm. Next, the peptide (12.5 µmol) was added to the PEG diacrylate solution, and reacted at room temperature for 5 min. A sample was then separated using size exclusion chromatography, and a single peak was detected, with absorbance maxima at 205, 220, and 270 nm, with the same retention time as PEG diacrylate. This indicated that the peptide reacted with the PEG diacrylate. Similar studies were performed using C18 chromatography, using a gradient from 95% water with 0.1% trifluoroacetic acid, 5% acetonitrile to 40% water with 0.1% trifluoroacetic acid, 60% acetonitrile. The peptide Ac-GCGYGRGDSP-NH$_2$ (SEQ ID NO: 62), eluted at about 20% acetonitrile, whereas PEG or PEG-3400 diacrylate eluted at about 40% acetonitrile. Incubation of 1 mol of the peptide per 2 mol of PEG-3400 diacrylate in buffered water at pH 8 led to the disappearance of the peptide-related peak that elutes at 20% acetonitrile, with the emergence of absorbance bands at 220 and 270 nm that coeluted with the PEG peak at 40% acetonitrile. Collecting the peaks and analyzing by MALDI-TOF mass spectrometry indicated that the PEG-associated peak contained a mixture of unmodified PEG-3400 diacrylate, and a new species with molecular weight that was the sum of the PEG-3400 diacrylate and the peptide molecular weights.

Figure 5:
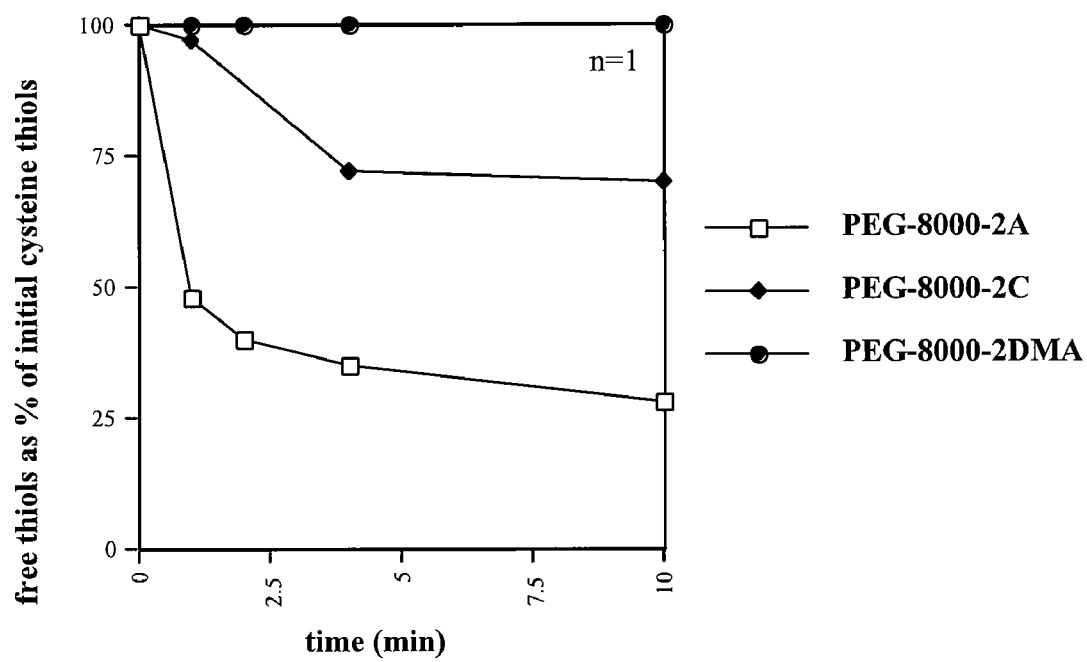
FIG. 5 is a graph showing the effect the steric influence of groups near the site of the conjugated unsaturation has on the reaction between a thiol (on cysteine) and an acrylate, crotonoate, or dimethylacrylate of an accordingly functionalized PEG.

Analysis of Reaction Kinetics of Acrylate, Crotonylate and Dimethylacrylate-terminated PEGs with Cysteine The amino acid cysteine was mixed in solution (0.1M phosphate, pH 8.0) with functionalized PEGs (PEG-8000-2A, PEG-8000-2C, and PEG-8000-2DMA) such that thiols and conjugated unsaturated groups were initially in equimolar concentrations (20 micromolar). In the presence of dimethacryloyl functionalities, the rate of thiol consumption was essentially zero over the time scale followed (10 minutes). In the presence of the less sterically hindered crotonoyl functionalities (one methyl substitution on the double bond), the rate of thiol consumption was increased. In the presence of the even less hindered acrylates, the concentration of thiols decreased more rapidly, but did not go to completion in the time course followed. See FIG. 5.

In a similar experiment where the concentration of conjugated unsaturated groups was ten times that of the thiol groups, the consumption of thiols by acrylates was extremely rapid. The reaction was complete by the taking of the first sample at time 1 minute (data not shown).

EXAMPLE 5

Demonstration of Hydrolysis of the Bond Formed Between a Cysteine-containing Peptide and Acrylated Polymers Hydrolysis in Solution The peptide Ac-GCGYGRGDSP-NH$_2$ (SEQ ID NO: 62) was dissolved in deionized water, and PEG-8000 diacrylate was dissolved in deionized water buffered with 10 mM HEPES and 115 mM triethanolamine at pH 8. After mixing 1 mol of the peptide per 2 mol of the PEG-8000 diacrylate, the reaction was followed by C18 chromatography, using a gradient from 95% water with 0.1% trifluoroacetic acid, 5% acetonitrile to 40% water with 0.1% trifluoroacetic acid, 60% acetonitrile. The peptide Ac-GCGYGRGDSP-NH$_2$ (SEQ ID NO: 62), eluted at about 20% acetonitrile, whereas PEG or PEG-8000 diacrylate eluted at about 40% acetonitrile. Rapidly, the free peptide peak at 20% acetonitrile disappeared, and the peptide then coeluted with the PEG peak at 40% acetonitrile. The solution containing the PEG-peptide adduct was then incubated at 37° C., and C18 chromatographic injections were made at later time points to detect hydrolysis of the peptide from the polymer. This was measured by observing the decrease in signal at 273 nm that coeluted with the PEG peak, and the reappearance of the free peptide peak at about 20% acetonitrile. MALDI-TOF mass spectrometry of the new peak eluting at about 20% acetonitrile revealed a product of molecular weight which corresponded to the molecular weight of the original peptide plus 72 mass units. This indicated that the new peak contains peptide modified with propionic acid, which was the product that would be expected following conjugate addition between the cysteine on the peptide and an acrylate group, followed by hydrolysis of the ester of the modified acrylate. A half-life for hydrolysis of the ester between the peptide and the PEG was found to be 4.86 days. This corresponds to a half-life of hydrolysis of about 3 weeks at pH 7.4.

Degradation of Gels Formed by Reaction of Polymers Containing Thiols and Acrylates PEG-3400 triacrylate was dissolved in 50 mM HEPES buffered saline, pH 8 at a concentration of 20% (w/v). PEG-3400 dithiol (Shearwater Polymers, Huntsville, Ala., USA) was dissolved in 1 mM MES buffered saline, pH 5.6 at a concentration of 20% (w/v). The solutions were mixed at a ratio of 1 acrylate:1 thiol. Gels formed after a few minutes at 37° C., and the gels were then transferred to tubes containing 10 mM HEPES buffered saline at pH 7.4, and were incubated at 37° C. The HEPES buffered saline was replaced daily for the first week, and the presence of a gel remaining in the tube was assessed daily. Solid gels were found to be gone from the tubes after about 3 weeks, with solid gels absent from the tubes between 18 and 24 days after cross-linking. This is compared with gels formed from PEG-8000 diacrylate by free-radical cross-linking (Pathak, supra), which are still present after 4 months at pH 7.4, 37° C.

Degradation of Gels Formed by Reaction of Molecules Containing Thiols and Acrylates 13.9 mg PEG-2500-3A was dissolved in 69.5 microliters (5.0 mg/25 microliters) of PBS·TEA (10 mM PBS containing 13 microliters of triethanolamine/ml). 7.0 mg of GCYKNRDCG (SEQ ID NO: 58) was dissolved in 65 microliters of PBS·TEA (2.7 mg/25 microliter). Equivolumes (25 microliters) of the two solutions were added to wells of a Corning flat-bottomed tissue culture treated polystyrene 96 well plates. As the second of the two precursor solutions was added, the pipet tip was used to stir the mixture for 2-3 seconds. Then the gels were allowed to set at 37° C. The gels were then transferred to tubes containing 10 mM HEPES buffered saline, pH 7.4. The gels were incubated at 37° C. and the disappearance of the solid gels was followed visually. Between 14 and 21 days, all of the solid gels were gone, indicating that they had degraded by hydrolysis of the ester bond between the peptide and the PEG.

Control of the Rate of Hydrolysis via Change in the Local Environment 13.9 mg PEG-2500-3A is dissolved in 69.5 microliters (5.0 mg/25 microliters) of PBS·TEA (10 mM PBS containing 13 microliters of triethanolamine/ml). 7.0 mg of GKKKKGCYKNRDCG (SEQ ID NO: 65) is dissolved in 65 microliters of PBS·TEA (2.7 mg/25 microliter). Equivolumes (25 microliters) of the two solutions are added to wells of a Corning flat-bottomed tissue culture treated polystyrene 96 well plates. As the second of the two precursor solutions is added, the pipet tip is used to stir the mixture for 2-3 seconds. Then the gels are allowed to set at 37° C. The gels are then transferred to tubes containing 10 in M HEPES buffered saline, pH 7.4. The gels are incubated at 37° C., and the disappearance of the solid gels is followed visually. The extra lysines found in the peptide ("GKKKK . . . " (SEQ ID NO: 73)) are added so as to provide additional nucleophiles to the local environment of the ester bond. Additionally, the cationic nature of the groups may also lead to a raising of the local pH. The combination of these two effects is expected to enhance the rate of hydrolysis of the ester bond between the peptide and the polymer.

EXAMPLE 6

Demonstration of Plasmin Hydrolysis of Gels Formed by Conjugate Addition with a Peptide Containing Two Cysteine Residues with a Plasmin Substrate Sequence in Between, and Lack of Hydrolysis of a Substituted Peptide Synthesis of Gels by Conjugate Addition Since enzymes and peptides are chiral, the stereochemistry of GCYKNRDCG (SEQ ID NO: 58) was altered to make a plasmin-stable nucleophile for gels made by conjugate addition. This plasmin stable peptide was: GCY-DLys-N-DArg-DCG (SEQ ID NO: 66). The sequence was otherwise not altered in order to maintain the extremely good water solubility properties of GCYKNRDCG (SEQ ID NO: 58).

Analytical C18 HPLC (linear acetonitrile gradient over 0.1% TFA in water) was used to confirm the relative plasmin-stability of GCY-DLys-N-DArg-DCG (SEQ ID NO: 66). The following samples were run: plasmin; GCYKNRDCG (SEQ ID NO: 58); plasmin+GCYKNRDCG (SEQ ID NO: 58); GCY-DLys-N-DArg-DCG (SEQ ID NO: 66); and plasmin+GCY-DLys-N-DArg-DCG (SEQ ID NO: 66). Plasmin (micromolar) was present at $^1/_{1000}$ the concentration of the peptide (millimolar) and hence did not affect overlaid absorbance chromatograms. Overlaying the traces (absorbance at 220 nm or 278 nm) of the peptide elutions vs. those of the peptide+plasmin. demonstrated that most of the GCYKNRDCG (SEQ ID NO: 58) peptide was degraded in approximately 1 hour at 37° C. The GCY-DLys-N-DArg-DCG (SEQ ID NO: 66) peptide however, was unaffected by the plasmin at 24 hours, and remained unaffected over the lifetime of the plasmin in the sample (sample injected for C18 at 2 weeks).

Demonstration of Plasmin-sensitivity and Plasmin-resistance

Gels were made according to the 40 microliter protocol given above. Some contained the GCYKNRDCG (SEQ ID NO: 58) peptide with Lys and Arg in the L configuration. Another contained the GCY-DLys-N-DArg-DCG (SEQ ID NO: 66) instead. All were exposed to 0.2 units of plasmin in 200 microliters and incubated at 37° C. The L-Lys, L-Arg configuration of the peptide was readily degraded by the enzyme. In one case, after 6 hours no gel remained. The DLys, DArg configuration gel has not been shown to degrade by plasminolysis.

EXAMPLE 7

Incorporation of Peptides into Polyethylene Glycol Gels Formed by Photopolymerization Gel Synthesis Polyethylene glycol diacrylate of mol. wt. 8000 (230 mg/ml) was allowed to dissolve in HEPES buffered saline (10 mmol HEPES, Sigma, 8 g/L NaCl, pH 7.4) for 1 hr. Triethanolamine (Aldrich, 15.3 µl/ml) was added, and the pH of the solution was adjusted to pH 8 with 6 N HCl. Cysteine containing peptides were dissolved in 116.5 µl of HEPES buffered saline, and added to 870 µl of the PEG solution with vortexing. After 5 min 3.5 µl of N-vinyl pyrrolidone and 10 µl of a 10 mM solution of Eosin Y were added, followed by vortexing. Gels were formed by exposure to light at 75 mW/cm$^2$ for 1 min (Cermax Xenon Lightsource, transmitting light between 470 and 520 nm; ILC Technology, Sunnyvale, Calif., USA). Gels were allowed to swell in Tris buffered saline, pH 7.4 (4.36 g Tris HCl, 0.64 g Trizma base, 8 g NaCl, 0.2 g KCl per 1 L, all from Sigma) for 36 hr.

Cell interaction with PEG gels containing peptides incorporated by conjugate addition in which the gel is formed by photopolymerization.

Figure 6:
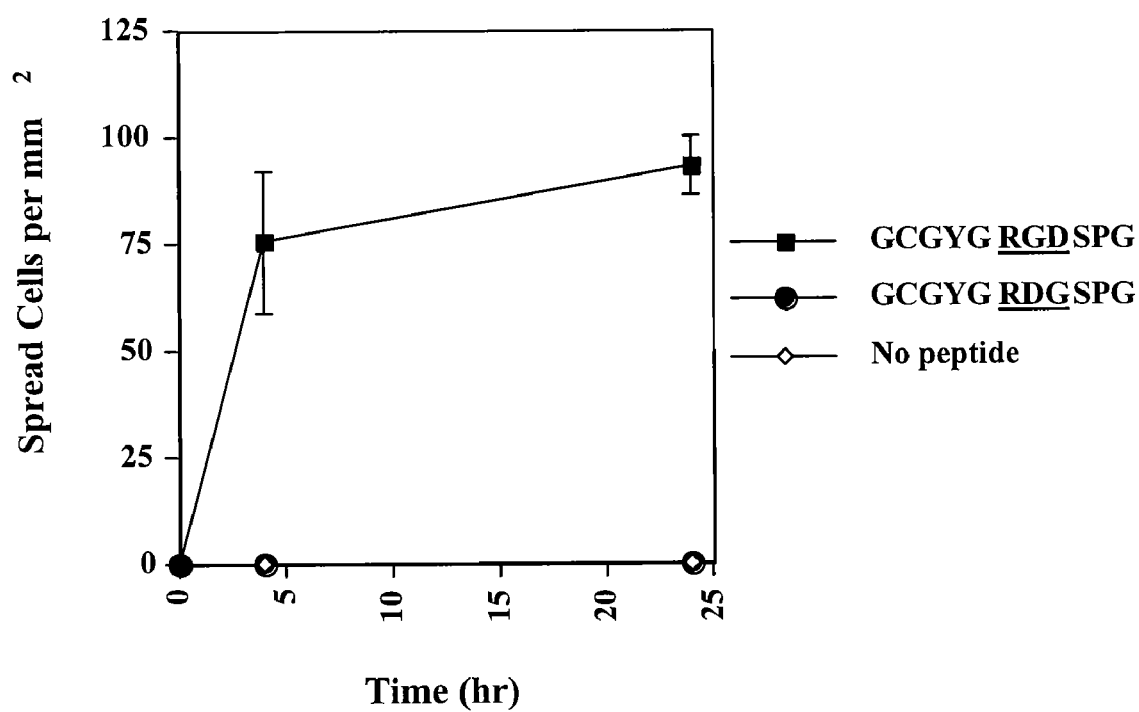
FIG. 6 is a graph showing the effect of the incorporation of an RGD peptide sequence into hydrogels of the present invention on cell adherence and spreading.

PEG gels were prepared as described above, using the peptide GCGYGRGDSPG (SEQ ID NO: 61). Most cells have receptors that recognize the sequence GRGDSPG (SEQ ID NO: 74), and cells will interact with surfaces displaying immobilized RGD containing peptides. To test cellular interactions of cells with PEG gels containing peptides incorporated via conjugate addition, gels were formed and human umbilical vein endothelial cells were seeded onto the gels. The change in the shape of the cells on the surface was observed, which indicated that the cells were interacting with the peptides on the surface. The change in shape is referred to as spreading, and refers to the change of the cell shape from spherical to flattened and polygonal on the surface. No cell spreading occurred on the PEG gels without peptide, and the specificity of the GCGYGRGDSPG (SEQ ID NO: 61) peptide was confirmed by comparison with gels containing the peptide GCGYGRDGSPG (SEQ ID NO: 68), which contains the same amino acids, but in a different sequence, and which has no biological activity. Cells were seeded onto the gels at a concentration of 400 cells per mm$^2$, and the number of spread cells per area was counted at different times (see FIG. 6). The experiments were performed using the normal cell culture medium. Cells could only spread on gels that contained the peptide GCGYGRGDSPG (SEQ ID NO: 61), which was incorporated into the gels utilizing a conjugate addition reaction.

EXAMPLE 8

Formation of pH Sensitive Gels Using Conjugate Addition Reactions

The peptide GCCGHHHHHGCCG (SEQ ID NO: 67) was synthesized as described above. The peptide (10 mg) was dissolved in 15 µl of 10 mM phosphate buffered saline, pH 7.4 and 25 µl ethanol. The pH of the solution was adjusted to pH 5.8 using 1N NaOH, and then PEG diacrylate, mol. wt. 400 (7.5 µl, Aldrich), was added. The mixture was incubated at 37° C. for 5 min. A hydrogel was formed, that demonstrated about a 50% increase in diameter upon changing from pH 7.4 to pH 5.8.

Gels were polymerized as spheres by adding the gelling solution from above to 1 ml of cyclohexane containing 94 mg of Hypermer B239 (ICI Surfactants, Wilmington, Del., USA), with vortexing at 37° C. for 10 min. Spheres were produced with diameters ranging from 2 µm to 20 µm, which demonstrated about a 50% increase in diameter upon changing from pH 7.4 to pH 5.8.

EXAMPLE 9

Formation of Particles for Protein Delivery Applications

PEG-3400 triacrylate is dissolved in 50 µM HEPES buffered saline, pH 8 at a concentration of 20% (w/v), with 2% albumin (Sigma, St. Louis, Mo., USA). PEG-3400 dithiol (Shearwater Polymers, Huntsville, Ala., USA) is dissolved in 1 mM MES buffered saline, pH 5.6 at a concentration of 20% (w/v). The solutions are mixed at a ratio of 1 acrylate: 1 thiol. The liquid solution (50 µl) is rapidly added to 1 ml of cyclohexane containing 100 mg Hypermer B239 (ICI Surfactants, Wilmington, Del., USA), with rapid stirring. The mixture is heated to 37° C. for 30 min. The polymerized, protein-containing spheres are then washed with additional cyclohexane to remove surfactant, followed by drying in vacuum to remove cyclohexane. The particles are then resuspended in HEPES buffered saline, pH 7.4. Release of protein from the microspheres is measured by changing the resuspending medium daily, and protein in the resuspending medium is assessed using size exclusion chromatography combined with UV detection at 280 nm. Protein concentrations in the resuspending medium are determined from a concentration standard curve for albumin at 280 nm.

EXAMPLE 10

Targeting PEG-Triacrylate Microspheres to Cells and Tissues Using Peptides Incorporated Via Conjugate Addition Microspheres are formed via conjugate addition cross-linking of PEG-triacrylate and the peptide GCYdKNdRDCG (SEQ ID NO: 66) as in Example 7, but additionally the peptide GCGYGRGDSPG (SEQ ID NO: 61) is also included in the reaction mixture, at a ratio of 1 GCGYGRGDSPG (SEQ ID NO: 61) to 8 GCYdKNdRDCG (SEQ ID NO: 66). The bioactive peptide is tested for the ability to localize microspheres to the surfaces of cells, as compared with microspheres containing no bioactive peptide.

EXAMPLE 11

Drug Encapsulation and Delivery by Gels Made by Conjugate Addition

Because the conditions for forming the PEG gels by conjugate addition are quite mild (room temperature to 37° C., pH approximately 8.0, in aqueous solvent), drugs such as protein drugs are incorporated into the gels for delivery. Such mild conditions do not denature most proteins. The drug is incorporated in a number of fashions. In one method, protein or other drug (soluble in water, ethanol, acetonitrile or other solvent for both the PEG and the enzyme sensitive peptide and which can be exchanged for aqueous buffer) is entrapped in the pore spaces of the gel during gel formation. Because free cysteines are relatively rare in natural proteins, one need only worry in the minority of cases that the protein will be cross-linked to the gel. Also, selectivity of the reaction is quite good since the addition of conjugated unsaturated compounds to other nucleophiles in proteins (hydroxyls and amines) is extremely slow compared to sulfhydryls. When the drug is larger than the pore spaces of the gel in its swollen state, as controlled by the molecular weight and concentrations of the precursors, then the drug does not diffuse out of the gel at an appreciable rate but is rather released by surface enzymatic degradation of the gel.

Figure 7:
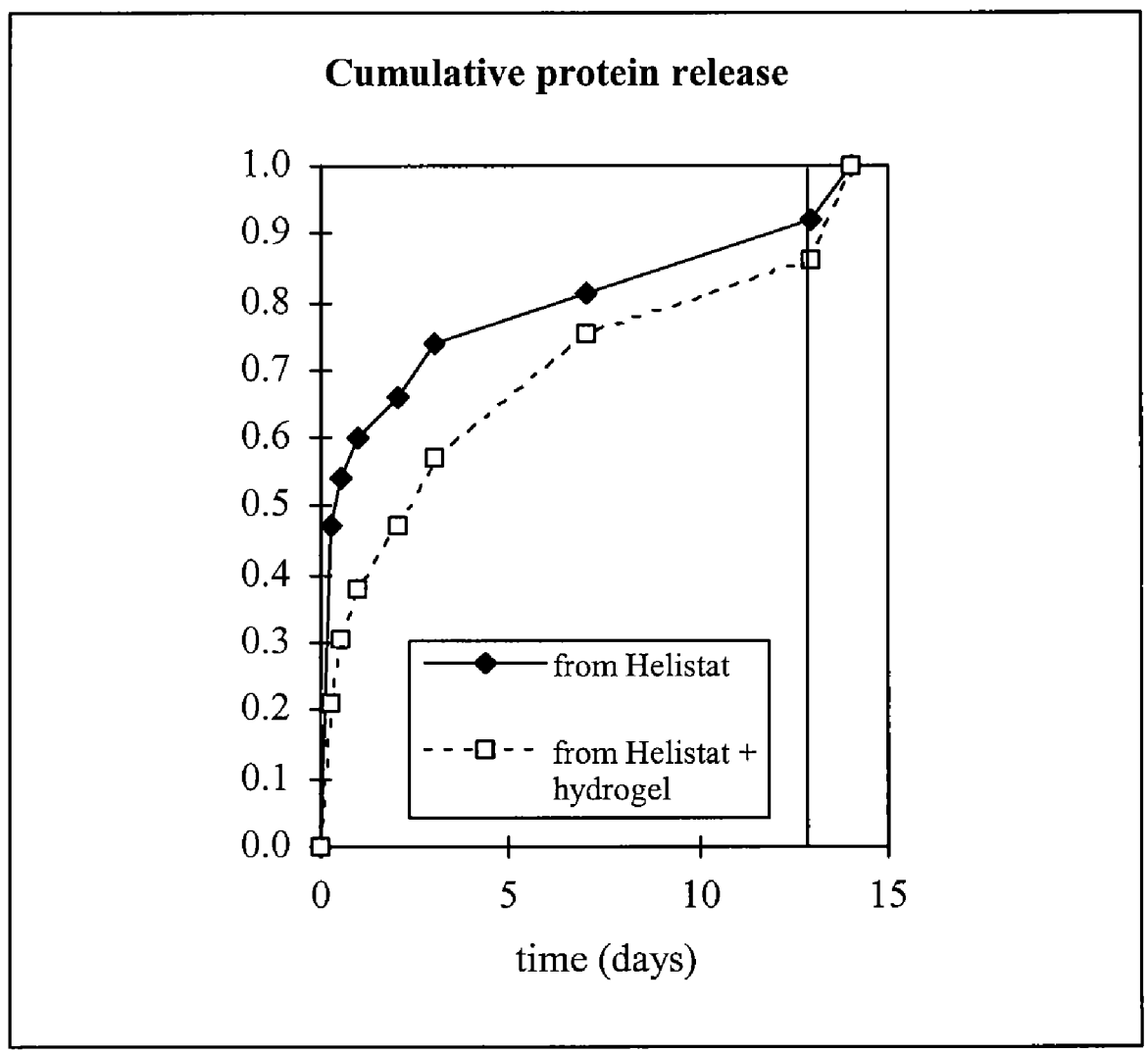
FIG. 7 is a graph showing the release of myoglobin from hydrogel-embedded collagen (Helistat) sponges. Note that at day 14, plasmin was added to the materials and this lead to the release of more myoglobin from the plasmin-sensitive hydrogels.

Diffusive and Degradative Control of Protein Release: Myoglobin Release Following Entrapment in Gel Pore Spaces The protein myoglobin (17,000 Da) was released from hydrogels made by conjugate addition between thiols and acrylates. PEG-3500-3A at 0.2 g/ml in PBS, pH 7.4 was mixed with a solution of the plasmin sensitive peptide GCYKNRDCG (SEQ ID NO: 58) such that the concentration of thiols and acrylates was the same and the final concentration of PEG-3500-3A was 10% (precursor solution). To some of the precursor solution, myoglobin was added (5.2 µl of 9.8 mg/ml myoglobin solution per 195 µl of precursor solution). Myoglobin was chosen as a model protein for growth factors, such as BMP-2, because of its similar size. 200 µl aliquots of precursor solution with and without myoglobin were made onto hemostatic collagen sponges. To some control sponges 5.2 µl of the 9.8 mg/ml myoglobin solution were added without gel precursors. To some sponges, PBS was added instead of myoglobin. After gels had solidified within the sponges, each sample was incubated in 4 ml of 10 mM PBS, pH 7.4, containing 0.1% sodium azide to prevent bacterial and fungal contamination. At 6 hr, 12 hr, 24 hr, 2 d, 3 d, 7 d, and 13 d the solution phase was removed from each sample and replaced with fresh PBS with 0.1% sodium azide. After day 13, the solutions were replaced with 0.08 units of plasmin in 4 ml PBS, the discontinuity marked by the vertical line in FIG. 7. Solutions were developed using the BIORAD/Bradford protein microassay and compared to a standard curve made from myoglobin solutions of known concentration. The samples with myoglobin within the hydrogel material showed a delayed release of the myoglobin (diffusion limited) but did, following hydrogel degradation by the enzyme plasmin. release a total amount of protein not different from the total released from the sponges alone (no hydrogel) (data not shown).

Release Employing Incorporated Affinity Sites

In another method, drugs such as heparin binding growth factors are electrostatically sequestered within the gel. This method is effective for trapping relatively low molecular weight compounds that otherwise diffuse out of the gel through its pores, especially in the swollen state of the gel. The sequestering is accomplished in a variety of methods.

In a first approach, one includes during gel formation by conjugate addition a heparin-binding peptide that contains one or more cysteines (i.e., the peptide can be pendant or serve as cross-linker), heparin, and the heparin-binding growth factor. In a second approach, one makes one's unnatural proteins with molecular biological techniques and engineers in heparin-binding regions where none (or where only low affinity ones) existed before. In a third approach, one makes unnatural proteins that contain unpaired cysteines. Then one covalently couples the protein via this cysteine linker to the gel during the gel formation process. In a fourth approach, one engineers both an unpaired cysteine and an enzyme-sensitive region into an unnatural protein. This protein is also covalently incorporated into the conjugate addition gels at gel formation, but this protein is released in the presence of the proper protease, which can be the same that degrades the bulk of the gel or a distinct enzyme. In a fifth case one makes a heparin mimic containing a thiol, for example, a cys residue, or a conjugated unsaturation and covalently incorporates it into the material in the presence of a heparin-binding growth factor such that the growth factor is electrostatically sequestered.

Incorporation of Growth Factor Affinity and Sequestering Growth Factors for Prolonged Release Heparin-binding proteins including heparin-binding growth factors are non-covalently bound to the material at material formation. If the protein to be bound does not contain a native heparin-binding sequence, a fusion protein is constructed (using molecular biological techniques and starting from the DNA level) to contain the native protein sequence and a synthetic heparin-binding domain.

For example, nerve growth factor (NGF) is expressed as a fusion protein in *E. coli* such that the protein contains a heparin-binding domain at the N-terminus and the NGF sequence at the C-terminus of the protein. This is accomplished by constructing a synthetic gene containing the DNA which codes for the desired fusion protein. The protein sequence to expressed is as follows:

(SEQ ID NO: 69)
*MGSSHHHHHHSSGLVPRGS*HMKDPKRLYRSRKLPVELESSSHPIFHRGEF

SVCDSVSVWVGDKTTATDIKGKEVMVLGEVNINNSVFKQYFFETKCRDPN

PVDSGCRGIDSKHWNSYCTTTHTFVKALTMDGKQAAWRFIRIDTACVCVL

SRKAVRZ where the region in italics is the Histidine tag derived from the expression vector, and the bold and italicized region is the thrombin cleavage site. Amino acids appearing in bold type without italics denote the heparin-binding sequence.

The cloning plasmid used for gene assembly is pUC 18. The DNA sequence of the gene is as follows from 5' to 3':

(SEQ ID NO: 70)
GAATTCCCATGGCATATGAAAGACCCGAAACGTCTGTACCGTTCTCGTAA

ACTGCCCGTGGAACTCGAGAGCTCTTCCCACCCGATTTTCCATCGTGGCG

AGTTCTCCGTGTGTGACTCTGTCTCTGTATGGGTAGGCGATAAAACCACT

GCCACTGATATCAAAGGCAAAGAGGTGATGGTGCTGGGAGAAGTAAACAT

TAACAACTCTGTATTCAAACAGTACTTCTTCGAAACTAAGTGCCGTGACC

CGAACCCGGTAGACTCTGGGTGTCGCGGCATCGATTCTAAACACTGGAAC

TCTTACTGCACCACTACTCACACTTTCGTTAAAGCGTTGACTATGGATGG

TAAACAGGCTGCCTGGCGTTTCATCCGTATCGATACTGCATGCGTGTGTG

TACTGTCCCGTAAAGCTGTTCGTTAAGGATCC

This gene is inserted between the EcoRI and HindIII sites in the polylinker cloning region of pUC 18. After assembly, this gene is inserted into the expression vector. Expression and purification are then performed.

Using standard Fmoc peptide synthesis described above in Example 1, a heparin binding peptide, such as GCGK(βA) FAKLAARLYRKA (SEQ ID NO: 71; see Table 5) is synthesized. For material formation, the peptide is preincubated with the conjugated unsaturated precursor; the fusion protein is preincubated with heparin; then the fusion protein-heparin complex is added to the peptide-unsaturation such that the peptide is covalently coupled to the conjugated unsaturation and simultaneously heparin forms a non-covalent bridge between the peptide and the protein. Then the thiol containing cross-linking precursor is added, and the material is formed with the heparin-bound protein throughout.

Covalent Incorporation of Proteins and Potential for Enzymatically Controlled Release A fusion protein is constructed to contain the protein of interest and at one terminus a short peptidyl sequence degradable by an enzyme, such as plasmin, and a cysteine distal to the site for proteolysis. The cysteine allows covalent incorporation of the protein in the material at material formation. The site for proteolysis allows for release of the protein in its native form at a rate determined by cellular activity, for example, activation of proteases such as plasmin or collagenase used in cell migration. The release of the protein can be controlled by the same or by a different enzyme than the one that degrades the material itself. There are also cases where covalent binding of the protein to the material without enzymatic release is desired. In these cases, the protein is engineered starting from the DNA level to contain an unpaired cysteine (e.g., at one of the termini of the protein) but no new site for proteolysis.

For example, the DNA for vascular endothelial growth factor (VEGF) is modified using site directed mutagenesis to introduce a cysteine near the N terminus of the protein. Molecular biological techniques are used to synthesize, purify and fold the protein. The protein is incubated with PEG-triacrylate with acrylates in excess of thiols in the protein. A plasmin sensitive peptide containing two thiols (GCYKNRDCG (SEQ ID NO: 58)) is added to cross-link the material with the growth factor incorporated throughout.

EXAMPLE 12

Drug (Including Non-Protein Drug) Delivery from a Material Via Covalently Linked Prodrugs which can be Released as Drugs by Proteolysis Another method for the covalent incorporation of prodrugs within a material is described. One can deliver a prodrug from a material where the material is soluble. Large molecular weight modifications of drugs are used to modulate circulation time, prodrug targeting, immune tolerance and mode of cellular uptake. A stable carrier-drug linkage is desired for transport. However, a bond that can be cleaved upon arrival at the desired location is of interest. An amide bond where one constituent of the bond is an L-amino acid recognized by a proteolytic enzyme is appropriate. Kopecek et al. (Pato, J., M. Azori, K. Ulbrich, and J. Kopecek, Makromol. Chem. 185: 231-237, 1984.) have published a great deal with regard to such enzymatically degradable soluble macromolecular drug carriers. However, little work appears with regard to enzymatically controlled drug delivery from solid materials, such as hydrogels. Delivery from a solid material serves to localize drug delivery to a desired site, for example, the site of material formation. Delivery from a solid material where the drug release is performed by cellular activity, such as expression of proteolytic enzymes, controls the rate of release such that cellular activity (e.g., cell migration) determines the rate of release.

The functional groups of a drug (such as anti-cancer drugs doxorubicin or daunorubicin) are protected with the exception of amine functional groups. The amine groups on the drug are coupled to an amino acid or peptide by formation of an amide bond. The amino acid or peptide is chosen to be degradable amino-terminal to the amino acid (Y) or peptide (XXXXY; SEQ ID NO:72), hence at the amide bond that joins the amino acid or peptide to the drug, by a proteolytic enzyme, such as plasmin which cleaves amino-terminal to lysine and arginine. Either a thiol (e.g., cysteine) is included in the coupled peptide or is next coupled to the amino acid or peptide portion of the peptide-drug conjugate. The drug and peptide functional groups are deprotected (to give SH-XXXXY-drug). At material formation, the thiol-peptide-drug conjugate is covalently coupled to the material by way of conjugate addition of the thiol on a conjugated unsaturation in the material precursor. The drug is released from the material by enzymatic activity, such as plasminolysis, that cleaves the amide bond (Y-drug) linking the drug to the material.

Alternatively, the functional groups of a drug (such as the prostaglandin antagonist diclofenac) are protected with the exception of carboxyl functional groups. The carboxyl groups are activated and coupled to a peptide by formation of an amide bond at the peptide amino terminus. The peptide is designed to contain a thiol (e.g., cysteine) and to be degradable carboxyl-terminal to the peptide, hence at the amide bond that joins the peptide to the drug, by a proteolytic enzyme which cleaves carboxyl-terminal to specific amino acids (Y). The drug and peptide functional groups are deprotected. At material formation, the thiol-peptide-drug conjugate (drug-YXXXX-SH) is covalently coupled to the material by way of conjugate addition of the thiol on a conjugated unsaturation in the material precursor. The drug is released from the material by enzymatic activity that cleaves the amide bond (drug-Y) linking the drug to the material.

EXAMPLE 13

Tissue Regeneration

Ectopic (Subcutaneous) Bone Formation in the Rat

Materials were made essentially according to Example 3, but under sterile conditions and with PEG-3500-3A, a molar ratio of acrylates: thiols of 1:1, and a molar ratio of GCGYGRGDSPG (SEQ ID NO: 61): acrylates of 1/12. At the time of gel formation, a recombinant human growth factor, BMP-2, which induces bone formation was added to the precursor solution at a concentration of 250 µg/ml of precursor solution. Precursor solution was added to hemostatic collagen sponges (Helistat; 8 mm diameter, approximately 3.5 mm height). Precursor solution was added until the sponges could not absorb more solution (approximately 160 µl). The gels were allowed to solidify in the sponges. Gels were briefly washed with PBS then kept minimally wet until implantation subcutaneously in rats. The implants were removed after two weeks, fixed, and hematoxylin and eosin stained. The materials were well infiltrated by cells with very little residual material remaining and promoted bone formation (mineralization and marrow formation) and vascularization. This indicates that the materials can deliver active biomolecules (e.g., growth factors) and can be infiltrated by cells in vivo.

Bone Regeneration

Hydrogel materials can be useful in bone regeneration in a variety of healing situations, for example, following trauma, tumor removal, or spinal fusion. In one example, hydrogel material, for example, as described above, is applied in the space within a spinal fusion cage, containing within that material a bone morphogenetic protein, such as BMP-2, TGF-β, or BMP-7. This bioactive formulation is useful in enhancing the probability of successful spinal fusion within the case. Use of such a material can circumvent some of the difficulties with current surgical methods, such as filling the space within the cage with amorphous bone allograft (associated with disease transmission and high cost) and filling the space with bone autograph, for example, obtained from the iliac crest (associated with additional morbidity and hospitalization cost).

Skin Regeneration

Hydrogel material can be useful in skin healing and regeneration, for example, in the closure of diabetic foot ulcers, pressure sores, and venous insufficiency ulcers. A hydrogel, for example, as described above, can be used to delivery growth factors that enhance the closure of these wounds, such as vascular endothelial cell growth factor, a TGFβ, activin, keratinocyte growth factor, platelet-derived growth factor, epidermal growth factor, or a number of other growth factors. These growth factors may be incorporated within the hydrogel either by entrapment or by biospecific affinity (e.g., by affinity for heparin).

EXAMPLE 14

Figure 8:
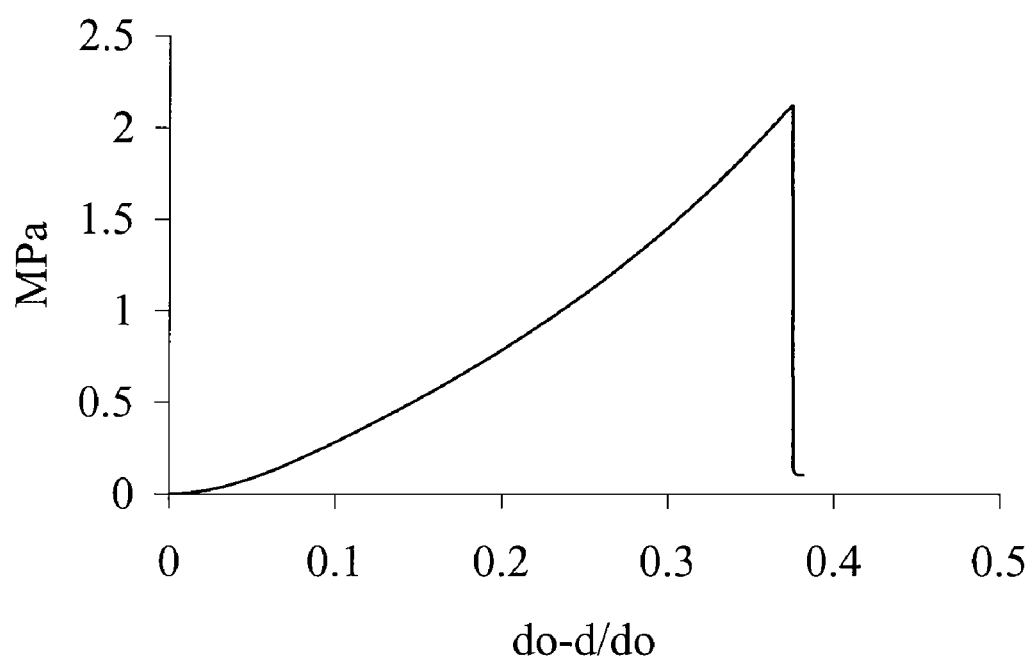
FIG. 8 is a strain-stress curve for a 75% solid gel prepared in an aqueous system. The gels were prepared using pentaerythritol tetrakis (3-mercaptopropionate) and PEG diacrylate 570 at 75% solid in phosphate buffered saline at pH 9.0. The gels showed approximately 37% deformation and 2 MPa ultimate strength when submitted to compressive loads.

Hydrogel and Non-hydrogel Materials for Bearing Structural Loads Structural Materials Formed by Conjugate Addition Reactions Pentaerythritol tetrakis (3-mercaptopropionate) (QT) (424 mg) and 997 mg of polyethylene glycol diacylate 570 (PEGDA) were combined neat and mixed well by vortexing. Air bubbles were removed by sonicating. PBS 0.01 M solution prepared at pH 9.0 (10 mM PBS adjusted to pH 9.0 with triethanolamine (EtOH$_3$N) mixed with an equal volume of 10 mM PBS adjusted to pH 9.0 with 1N NaOH) (473 mg) was add to the mixed precursors. The mixture was again vortexed for about 2 minutes to mix well and disperse the precursors in the aqueous solution. Following vortexing, the mixture was again sonicated to remove air bubbles. At room temperature the material gelled in about 20 to 30 minutes. The resulting gel demonstrated ultimate strength of about 2 MPa and withstood deformations of about 35% in compression (FIG. 8).

Control of Mechanical Properties by Hydrophobicity (Pentaerythritol Triacrylate)

Figure 9:
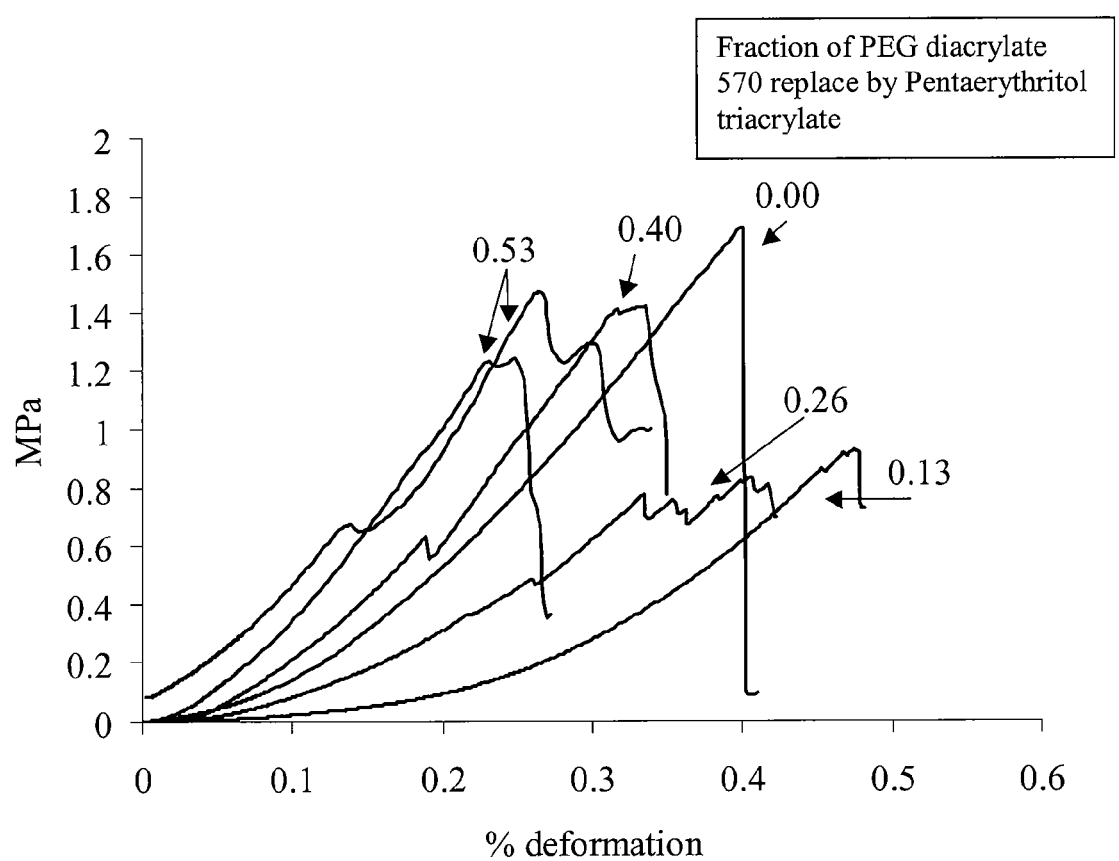
FIG. 9 shows stress-strain curves for a 75% solid gel prepared in an aqueous system with various contents of pentaerythritol triacrylate replacing the PEG diacrylate 570. The gels were prepared using pentaerythritol tetrakis (3-mercaptopropionate) and PEG diacrylate 570 and pentaerythritol triacrylate at 75% solid in phosphate buffered saline at pH 9.0. The gels showed that the stiffness of the gel was manipulated by the content of the hydrophobic triacrylate.

QT and pentaerythritol triacrylate were mixed neat at a ratio of 489 mg to 596 mg (mixture 1). QT and PEGDA 570 were mixed at the ratio indicated above (mixture 2). 100 mg of mixture 1 was combined with 650 mg of solution 2 and 250 mg of PBS pH 9.0 was added and the entire mixture was vortexed to mix. Similar gels were prepared for 200, 300, and 400 mg of mixture 1. To these were added 550, 450 and 350 mg of mixture 2 respectively. To all of these 250 mg of the activating buffer was added. The resulting gels demonstrate a modulation of the mechanical properties using the addition of a hydrophobic coprecursors. An increase in the content of the hydrophobic TA increased the stiffness of the resulting gel (FIG. 9).

Varying Thiols to Acrylate Ratio

QT and PEGDA 570 were combined neat to achieve ratios of thiol to acrylate of 0.8, 0.9, 1.0, 1.1, 1.3 by adding the appropriate amount of QT to 1000 mg of PEGDA 570 and adding PBS 9.0 in a quantity to make 75 wt % solid gels. As an example, for the 0.8 thiol to acrylate ratio, 343 mg of QT were added to 1000 mg of PEGDA. The two components were mixed by vortexing and then 448 mg of PBS 9.0 was added. Again the mixture was vortexed and then allow to gel. At thiol acrylate ratios from 1, the resulting gels exhibit significant decreases in ultimate strength. At ratios from 1.0 to 1.3, the gels were less sensitive to changes in the thiol/ acrylate ratio. The table below (Table 8) presents the ultimate strengths obtain at each of the thiol/acrylate ratios.

TABLE 8

Ultimate strength of gels with various thiol/acrylate ratios

| Thiol/acrylate | Ultimate Strength |
| --- | --- |
| .8 | 0.89 ± 0.79 |
| .9 | 0.64 ± 0.07 |
| 1.0 | 2.21 ± 0.12 |
| 1.1 | 2.29 ± 0.13 |
| 1.2 | 1.93 ± 0.24 |
| 1.3 | 1.82 ± 0.23 |

Control of Mechanical Properties by Addition of Particles

Figure 10:
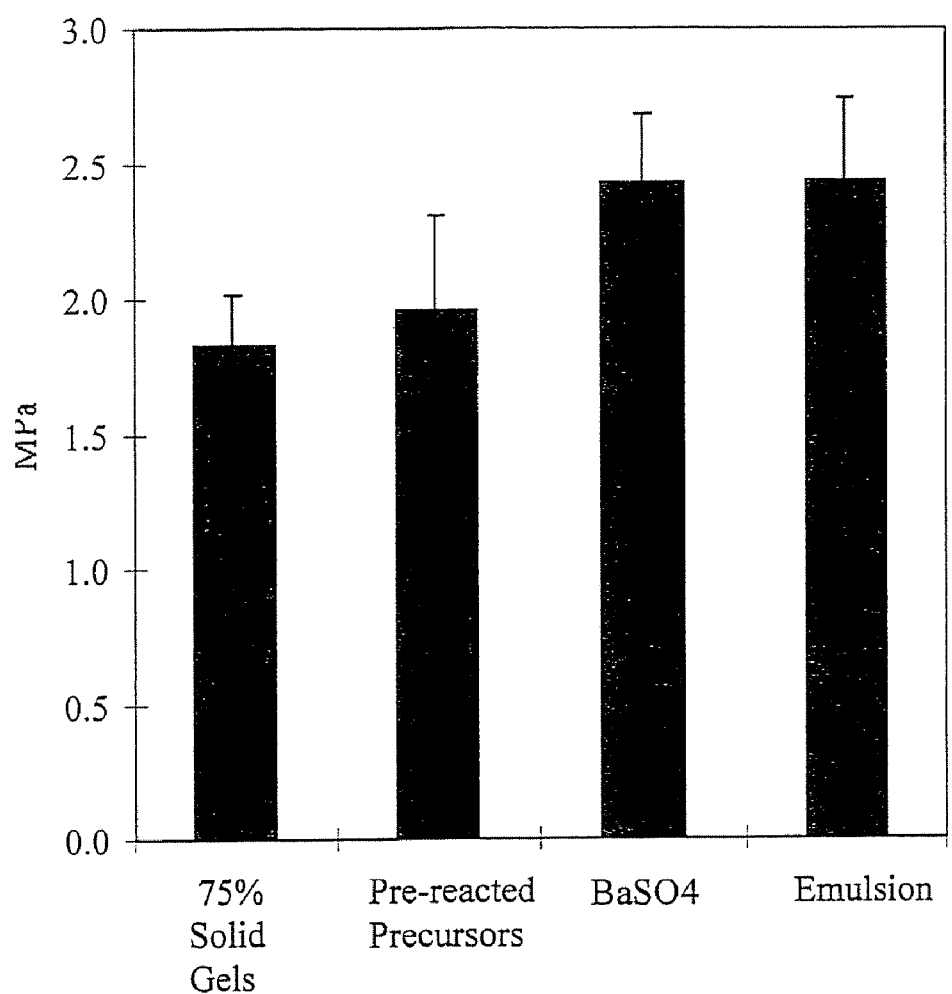
FIG. 10 is a graph showing the effect of the addition of inorganic particles or surfactants to the gels on the ultimate strength of the gels. Gels prepared in the aqueous system at 75% solid (75% solid gels) were compared to those in which $BaSO_4$ was added at 10%, or when a surfactant, sorbitan monooleate (Emulsion), was added at 1%. Gel obtained from precursors pre-reacted were also compared to gels obtained by the pentaerythritol tetrakis (3-mercaptopropionate) and PEG diacrylate 570 precursors (Pre-reacted precursors).
Figure 11:
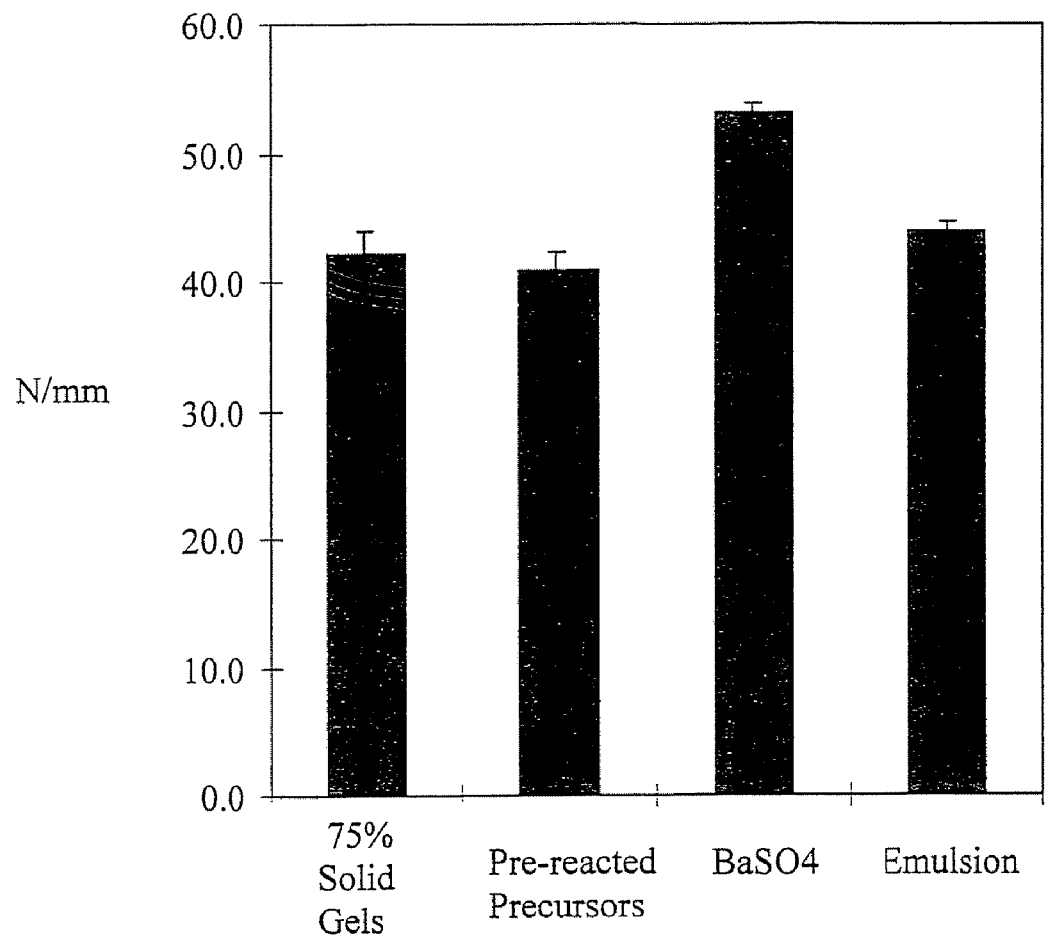
FIG. 11 is a graph showing the effect of the addition of inorganic particles or surfactants to the gels on the stiffness of the gels. Gels prepared in the aqueous system at 75% solid (75% solid gels) were compared to those in which $BaSO_4$ was added at 10%, or when a surfactant, sorbitan monooleate (Emulsion), was added at 1%. Gels obtained from precursors pre-reacted were also compared to gels obtained by the pentaerythritol tetrakis (3-mercaptopropionate) and PEG diacrylate 570 precursors (Pre-reacted precursors).
Figure 12:
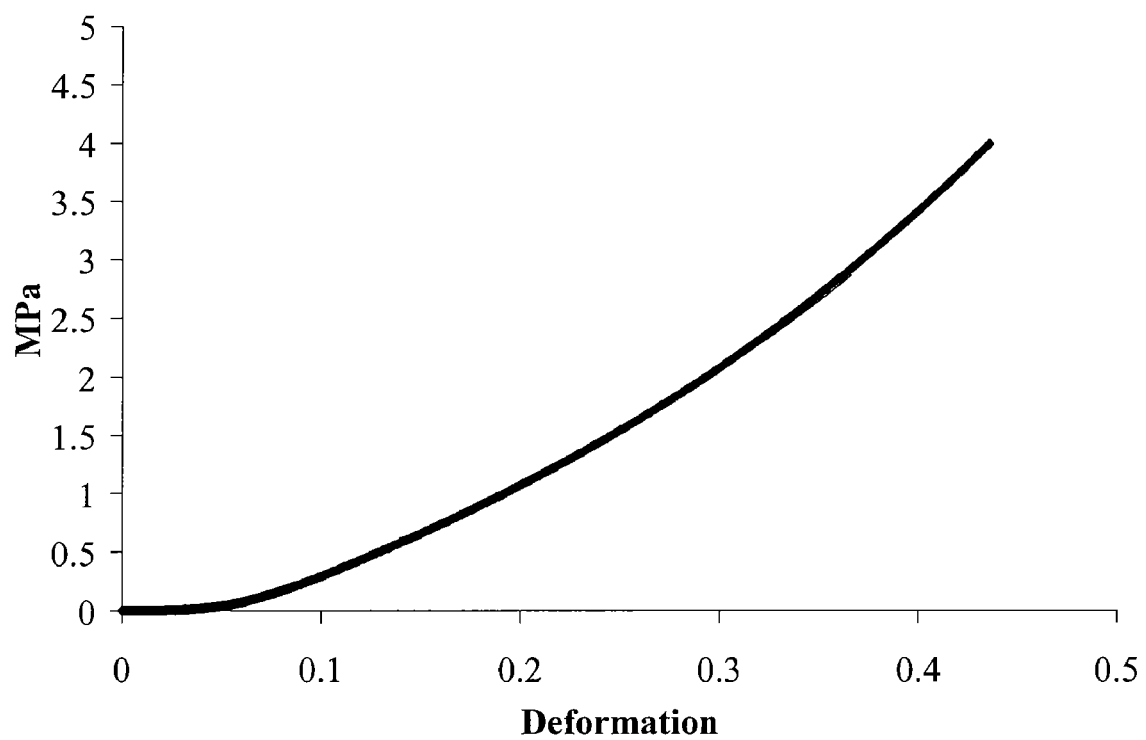
FIG. 12 is a stress-strain curve for a gel prepared in an aqueous system loaded with fumed silica (14 nm). The gels were prepared using pentaerythritol tetrakis (3-mercaptopropionate) and PEG diacrylate 570 in phosphate buffered saline at pH 9.0, reinforced with fumed silica particles (14 nm).

Precursors, QT and PEGDA 570, were combined as outlined above. Prior to addition of the activating buffer (pH 9.0 PBS), 10 wt % of BaSO4 particles, balance fixe (0.8 μm), were added to the mixed precursors. The activating buffer was added and then the entire mixtures were vortexed and then allowed to gel. The same quantities of the precursors, as noted in the example above, were used. The gels resulting from addition of the BaSO4 showed some increase in ultimate strength and substantial increase in stiffness (FIGS. 10 and 11). QT and PEGDA 570 gels were also prepared that were loaded with fumed silica particles (14 nm). 424 mg of QT was combined with 997 mg of PEGDA. Prior to addition of the PBS pH 9.0 buffer, the buffer was loaded with 10% fumed silica. 250 mg of the PBS-fumed silica mixture was add to the QT/PEGDA mixture and then vortexed to mix. The gels resulting from the addition of fumed silica showed significant increases in the ultimate strength. FIG. 12 presents the stress strain curve for the fumed silica gels in sub failure compression. At 4 MPa in compression these gels had not failed.

Improvement of Mechanical Properties by Use of Emulsifiers

Gels were prepared by emulsion by adding sorbitan monooleate to the PBS 9.0 buffer at 4 wt % prior to addition of the buffer to the mixed precursors. QT and PEGDA 570. The surfactant/pH 9.0 buffer mixture was then added to the mixed precursors. Otherwise the same quantities and procedures were used as noted above. The resulting gels exhibited a similar increase in ultimate strength compared to the gels with inorganic particles added but without the associated increase in stiffness (FIGS. 10 and 11).

Preparations of Materials in Solvents Including Organic Solvents

Figure 13:
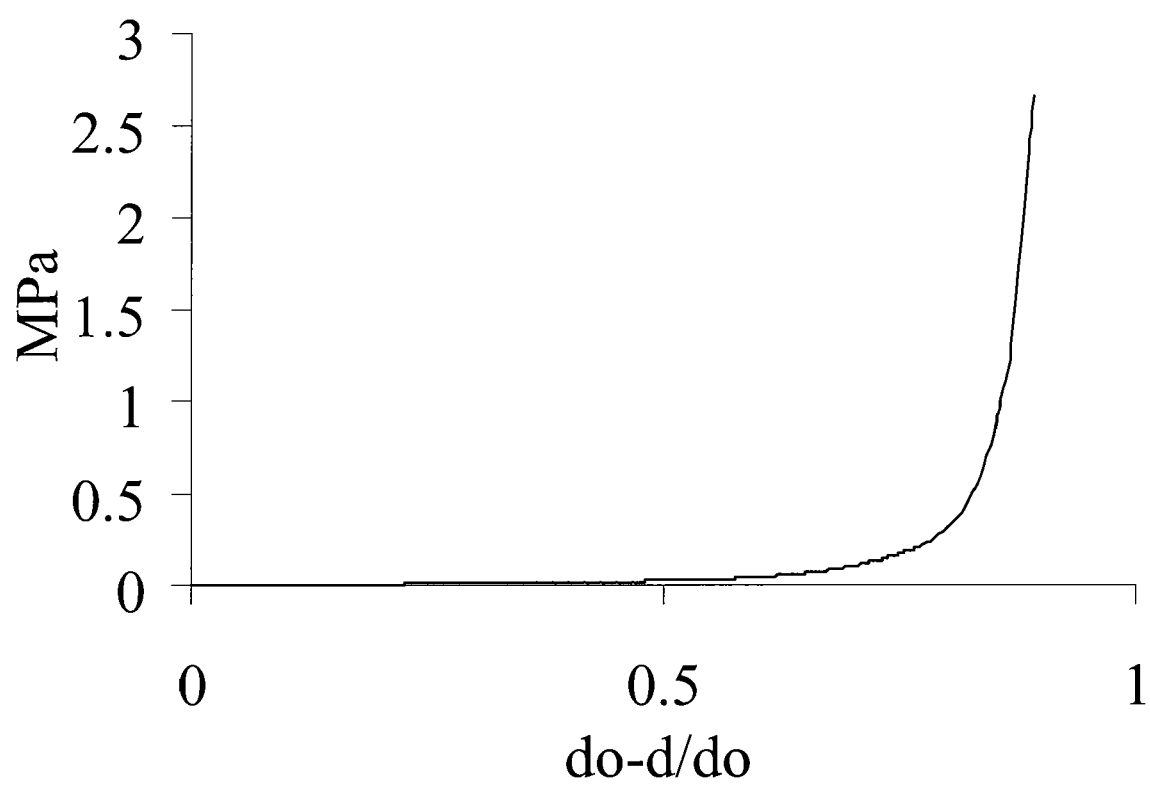
FIG. 13 shows a stress-strain curve for a 10% solid gel prepared in a N-methyl pyrrolidone/PEG 400 cosolvent. The gels were prepared using pentaerythritol tetrakis (3-mercaptopropionate) and PEG diacrylate 570 at 10% solid in N-methylpyrrolidone/PEG 400.

QT and PEGDA were combined in the ratios indicated above. These precursors were then dissolved at 10 wt % in N-methylpyrrolidinone (NMP) and then allowed to gel. After the gels cured for 24 hours, they were placed in deionized water to allow solvent exchange. During solvent exchange the volume of the gels reduced 60% to a new equilibrium volume. The resulting equilibrated gels showed soft elastic response to compression at low loads and an increase in stiffness with high deformation in compression. FIG. 13 shows a typical stress strain curve for this material.

Modulation of Mechanical Properties by Addition of Hydrophilic Additives

QT and PEGDA 570 were combined in the ratios indicated above. Poly(vinyl pyrrolidone) (40,000 MW) (PVP) was dissolved in the PBS 9.0 buffer at 1, 7, and 13%. The same quantities of the precursor mixture and the buffer/PVP solution were combined as indicated above. The mixture was vortexed and allowed to gel. These gels demonstrated the manipulation of mechanical properties due to the addition of the hydrophilic additive. The addition of PVP increased the equilibrium swelling of the gel and an increase in the PVP content further increased the swelling. An addition of PVP also resulted in a weaker softer gel.

Kinetics of QT and PEGDA 570 Gelation

Figure 14:
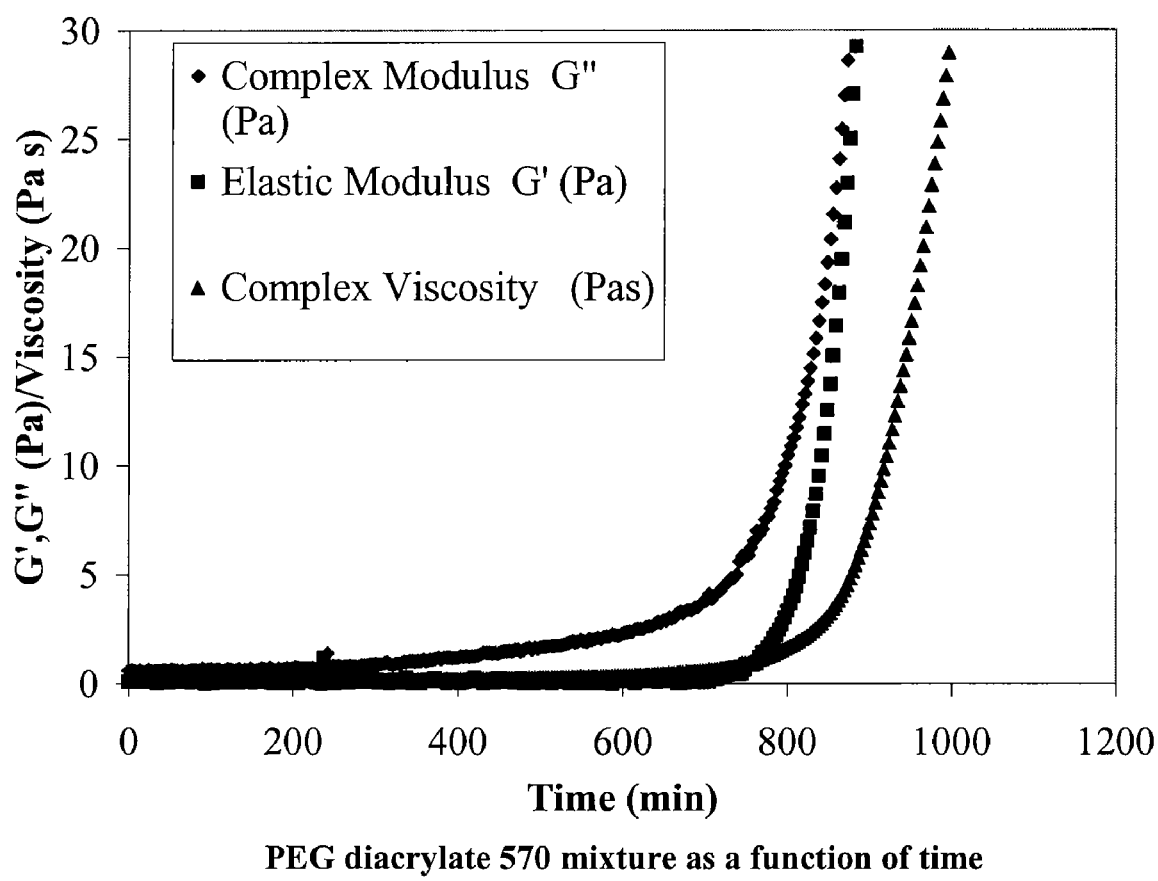
FIG. 14 shows elastic and complex moduli (G' and G") for pentaerythritol tetrakis (3-mercaptopropionate) and PEG diacrylate 570. Pentaerythritol tetrakis (3-mercaptopropionate) and PEG diacrylate 570 were mixed with a 1 SH to 1 C=C ratio without phosphate buffered saline pH 9.0 buffer. The mixture was vortexed and then the elastic and complex moduli were determined with time by rheology.

QT and PEGDA were combined neat in the ratios indicated above. After mixing the QT/PEGDA 570 by vortexing, the buffer was not added but instead 100 microliters of the mixture was placed between 20 mm plates of a CVO 120 rheometer with a gap of 100 um at room temperature. The mixture was maintained at room temperature while the elastic modulus, complex modulus and viscosity were followed with time using shear at 1 Hz with a strain amplitude of 0.3. With progression of the reaction the two combined precursors showed a gel point, defined by the time when the elastic modulus becomes greater than the complex modulus, of about 14 hours. FIG. 14 shows these two moduli for the combined precursors with time.

Figure 15:
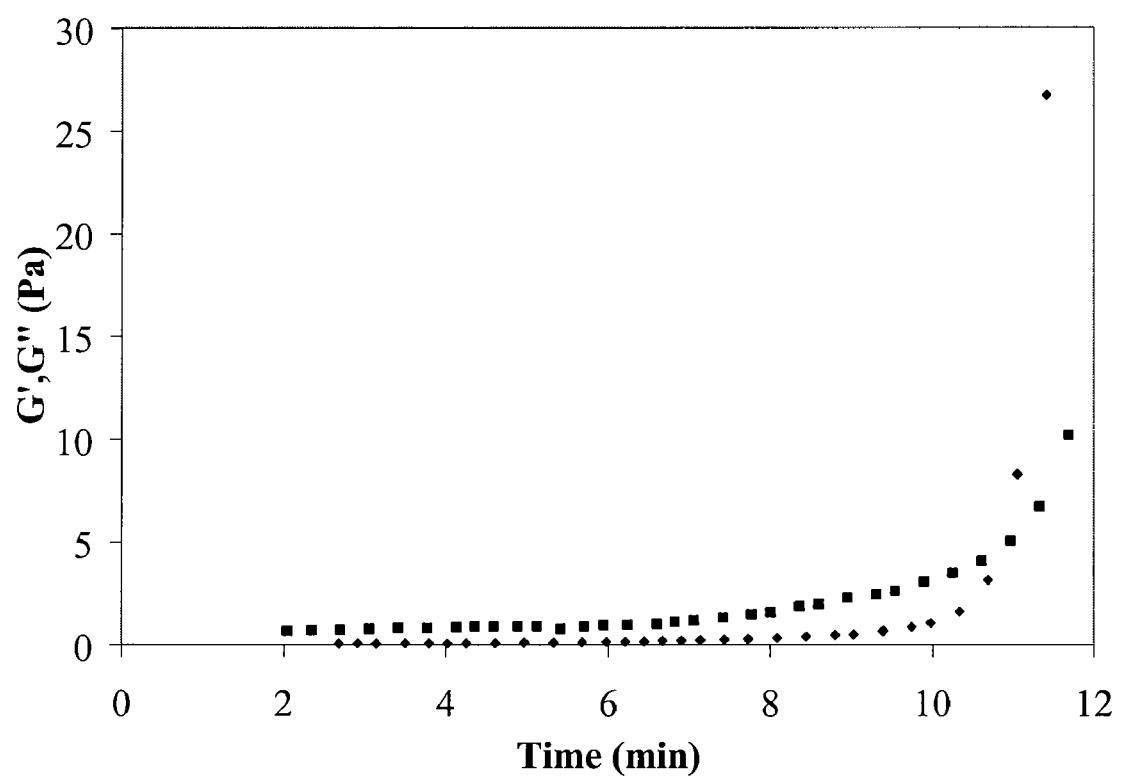
FIG. 15 shows elastic and complex moduli (G' and G") at 37° C. for pentaerythritol tetrakis (3-mercaptopropionate) and PEG diacrylate 570 activated with phosphate buffered saline at pH 9.0. Pentaerythritol tetrakis (3-mercaptopropionate) and PEG diacrylate 570 were mixed with a 1 SH to 1 C=C ratio and phosphate buffered saline pH 9.0 was added. The mixture was vortexed and then the elastic (♦) and complex (■) moduli were determined with time by rheology.

Next, more of the two precursors were combined as described above and the PBS 9.0 buffer was added, as described above. After mixing the precursors and buffer, the mixture was placed between the plates of the rheometer at 37° C. The frequency and amplitude were the same as the previous procedure. With the addition of the buffer, the kinetics of the gelation increased dramatically. At 37° C. the gel point occurred in about 11 minutes. FIG. 15 presents the moduli for the precursors activated with pH 9.0 buffer.

Biocompatibility of Gels in Tissue Sites

Precursors, QT and PEGDA 570, the buffers, and sorbitan monooleate were all filter sterilized. Blanc Fixe particles were sterilized by autoclave. Gel pins were prepared using the precursors, Blanc Fixe and sorbitan monooleate. Other pins were prepared using only the two precursors. The gel pins prepared with only the two precursors were prepared using the same procedure cited above, except that the activated and vortexed mixture was placed in molds to form pins prior to gelation and the gel pins containing the inorganic particle and the surfactant were prepared by combining the procedures described above. The pins were implanted into the right and left dorsal muscles of rabbits. Reference pins of polyethylene were also used. After 4 weeks histological sections of the implants and the surrounding tissue were performed. With both gel types tested, no significant differences were apparent compared to the reference materials. Rare macrophages, fibroblasts and neovessels were associated with the implanted gel pins. No necrosis, degeneration or any other local intolerance signs were induced by these gel compositions.

Toxicity and biocompatibility of the low molecular weight precursors can be improved by pre-reacting the precursors at quantities that result in higher molecular weight precursors with remaining functional groups. QT has been functionalized with 10 fold excess PEG-DA 570. The result of this process is a tetrafunctional acrylate consisting of each thiol of the QT capped with a diacrylate leaving a terminal acrylate free. A similar reaction with QT in excess gives a peg capped at each end with three free thiols giving a hexafunctional thiol. The combination of these precursors with 1:1 thiol to acrylate ratio gives similar gels as obtained by the direct application of QT and PEGDA 570 (refer FIGS. 10 and 11, noting the HT and QA values).

Control of Mechanical Properties by Preparation of Materials from Precursors of Mixed Molecular Weight End functional polymer cross-linked systems have shown that mechanical properties can be manipulated by using multimodal molecular weight distributions. Including a low molar content of a high molecular weight precursor in a low molecular weight system has a synergistic effect giving improved mechanical properties than are achievable by either molecular weight alone. Networks containing only short chains are brittle and networks containing only the larger component have very low ultimate strength. While, bimodal systems having predominately the small chains with a small molar ratio of the larger component show networks with a high ultimate strength compared to the larger molecular weight system and with improved extensibility compared to the short chain monomodal system (Pathak, supra, Llorente, M. A., et al., J Polym. Sci., Polym. Phys. Ed., 19:621, 1981.

Low molar content of a larger molecular weight precursor (i.e., PEGDA 20,000 or PEVAL 20,000) can replace some of the PEGDA 570, creating a bimodal system. The three precursor system can be combined (i.e., QT, PEGDA 570 and PEGDA 20,000) in an aqueous system at a pH providing sufficient reaction kinetics. The results are tougher gels. The hydrophilic/hydrophobic balance of this third (larger molecular weight precursor) can also be exploited to further modulate properties.

EXAMPLE 15

Preparation of Materials that are Responsive to Environmental Conditions

Temperature Sensitivity of the Precursors

If the precursors are temperature sensitive (i.e., soluble below a critical temperature below 37° C. and insoluble above the same temperature) but still possess thiol or conjugated unsaturated groups, they can be used to prepare gels with easy manipulation during mixing, but show the increased properties exhibited by gels obtained with the hydrophobic precursors. For this purpose either telechelic or grafted functional groups on poly(N-isopropylacrylamide), poly(propylene glycol-co-ethylene glycol), or other temperature sensitive polymers may be used. The precursors can be dissolved in water at a temperature below the critical temperature. The precursors solutions can be combined and allowed to gel. If the gel experiences a temperature increase above the critical temperature, then the gel will undergo a transition to a more hydrophobic state. The transition may or may not be associated with syneresis depending on the design of the temperature sensitive precursors and original concentrations.

pH Sensitivity of the Precursors

If the precursors are pH sensitive (i.e. soluble above or below a critical pH) but still possess thiol or conjugated unsaturated groups, they can be used to prepare gels with easy manipulation during mixing but show the increased properties exhibited by gels obtained with the hydrophobic precursors. For this purpose either telechelic or grafted functional groups on poly(N-isopropylacrylamide-co acrylic acid), poly (N-isopropylacrylamide-co dimethylaminoethylmethacrylate) or poly(acrylic acid) or other pH sensitive polymers may be used. The solubility of these materials can be altered by pH. The precursors solutions can be combined and allowed to gel. A pH change in the environment changes the hydrophobicity of the gel by protonating or deprotonating the gel. The transition may or may not be associated with syneresis depending on the design of the pH sensitive precursors and original concentrations.

EXAMPLE 16

Figure 16:
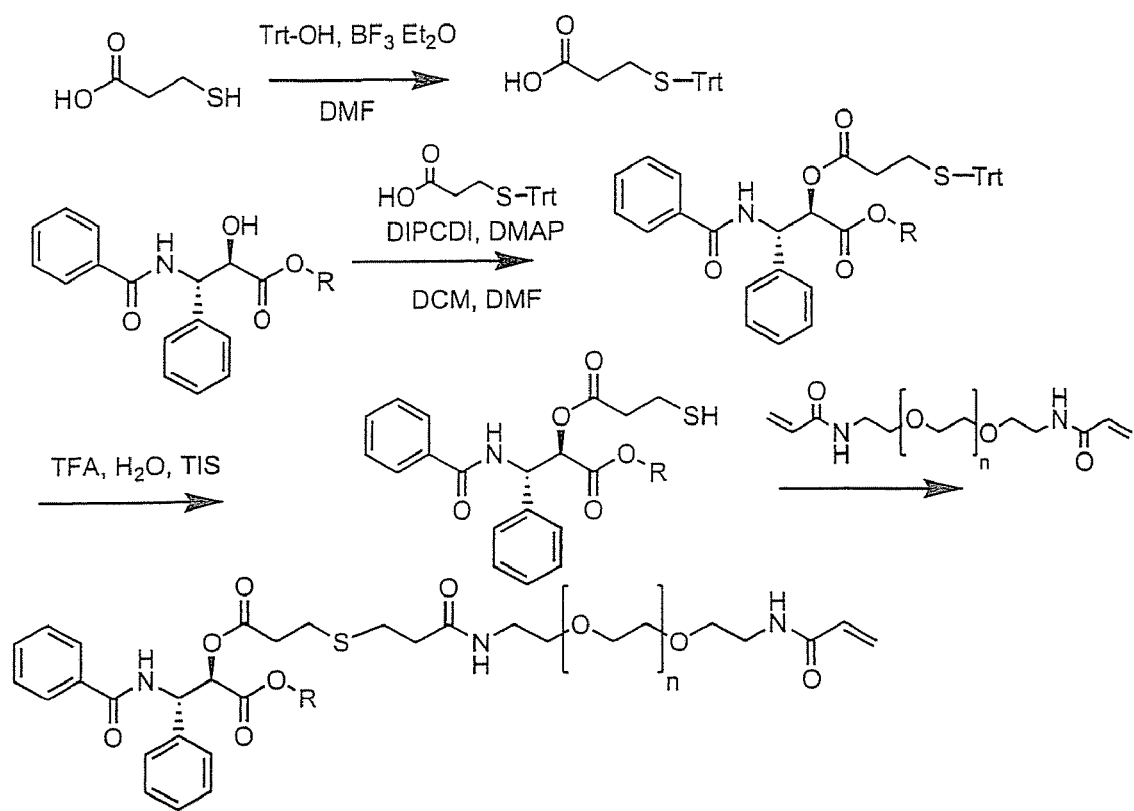
FIG. 16 is a schematic representation of the synthesis route for the modification of paclitaxel (Example 19) or the side chain of paclitaxel (Example 16) with a thiol-containing linker. This linker is than coupled to a PEG-linked unsaturation by a conjugate addition reaction, and the remaining PEG-linked conjugated unsaturated groups are cross-linked to form a biomaterial.

Formation of a Cross-linked Biomaterial Containing the Side Chain of Paclitaxel Coupled to PEG Through a Thiol-containing Linker A thiol-containing linker molecule was attached to a model compound, the side chain of paclitaxel (FIG. 16). This product was subsequently attached to a PEG-linked conjugated unsaturation (FIG. 16), and the remaining PEG-linked conjugated unsaturated groups were cross-linked to form a biomaterial. In terms of attachment chemistries, this model compound provides an inexpensive model of paclitaxel, and the results obtained with this derivative are relevant to work with the full paclitaxel molecule, as well as, other organic molecules containing an alcohol or amino group.

Preparation of Methyl Ester of Paclitaxel Side Chain-2'-O-3-thio-propionate

Step A) Preparation of 3-tritylthiol-propionic Acid

A solution of 0.87 ml (10 mmol) 3-mercaptopropionic acid and 2.86 g (11 mmol) triphenylmethanol in 40 ml N,N-dimethylformamide (DMF) was stirred for 30 min at 60° C. After the solution was cooled to ambient temperature, 1.43 ml (11.4 mmol) borontrifluor etherate was added and the reaction mixture was stirred at 60° C. for 4 hr. The solution was concentrated in vacuo and the residue was dissolved in 500 ml 5% $NaHCO_3$. The aqueous solution was washed with 250 ml diethyl ether, acidified to pH 3 using 1 M $KHSO_4$, and extracted twice with 500 ml ethyl acetate. The combined ethyl acetate fractions were washed with 250 ml brine and dried over $Na_2SO_4$. The product was obtained as a white solid in 90% yield.

$^1$H-NMR ($CDCl_3$) δ 2.23 (t, 2H, C$\underline{H}_2$S), 2.46 (t, 2H, C$\underline{H}_2$COOH), 7.23-7.43 (m, 15H, Trt)

Step B) Preparation of a Protected, Modified Paclitaxel Side Chain (N-Benzoyl-(2R,3S)-2-O-(3-tritylthio-propionate)-3-phenyl-isoserine methyl ester)

A solution of 120 mg (0.4 mmol) N-Benzoyl-(2R,3S)-3-phenyl-isoserine methyl ester and 280 mg (0.8 mmol) 3-tritylthio-propionic acid in 4 ml dichloromethane and 1 ml DMF was cooled to 0° C. Then 126 µl (0.8 µmmol) diisopropylcarbodiimide and a few crystals of dimethylaminopyridine were added and the reaction was stirred at 0° C. for 2 hr. After the reaction was complete based on TLC analysis of the reaction mixture, the solvents were removed in vacuo, and the crude product was dissolved in 50 ml dichloromethane. The organic solution was washed with 1 M $KHSO_4$, 5% $NaHCO_3$, and brine, consecutively, and dried over $Na_2SO_4$. After purification by column chromatography (silica, eluent: ethyl acetate/hexane 1:2 v/v), a white solid was obtained with a yield of 74%.

$^1$H-NMR ($CDCl_3$) δ 2.00-2.55 (m, 4H, C$\underline{H}_2$S and C$\underline{H}_2$COO), 3.67 and 3.73 (s, 3H, OC$\underline{H}_3$), 5.51 and 5.38 (d, 1H, C$\underline{H}$O), 5.72 and 5.83 (d d, 1H, C$\underline{H}$Ph), 6.35 and 6.96 (d, 1H, N$\underline{H}$), 7.15-7.59 (m, 23H, Ar Tax and Trt), 7.96 and 7.76 (d t, 2H, Ar Tax) $^{13}$C-NMR ($CDCl_3$) δ 27.71 and 26.68 ($\underline{C}H_2$S), 35.67 and 33.46 ($\underline{C}H_2$COO), 52.78 and 52.88 ($\underline{C}$HPh), 5.31 and 53.44 (H$\underline{C}$O), 66.96 and 67.14 ($\underline{C}$(Ph)$_3$ Trt), 74.82 and 74.53 (O$\underline{C}H_3$), 126.58-144.66 (Ar Tax and Trt), 165.41 and 166.86 ($\underline{C}$OOMe), 168.19 ($\underline{C}$OOCH), 170.48 ($\underline{C}$ONH)

Step C) Deprotection to Form Methyl Ester of Paclitaxel Side Chain 3-thio-propionate (N-Benzoyl-(2R,3S)-2-O-(3-thiopropionate)-3-phenyl-isoserine Methyl Ester)

A solution of the trityl protected compound in dichloromethane was added to a solution of TFA, triisopropylsilane, and water (95:2.5:2.5), and the reaction mixture was stirred at room temperature for 1 hr. The solvents were removed in vacuo, and the product was obtained after column chromatography (silica, eluent: ethyl acetate/hexane 1:2 v/v).

$^1$H-NMR (CDCl$_3$) δ 1.59-1.64 (m, 1H, S$\underline{H}$), 2.67-2.77 (m, 4H. C$\underline{H}_2$SH and C$\underline{H}_2$COO), 3.76 (s, 3H, OC$\underline{H}_3$), 5.50 (d, 1H, C$\underline{H}$O), 5.90 (d d, 1H, C$\underline{H}$Ph), 7.04 (d, 1H, N$\underline{H}$), 7.26-7.80 (m, 8H, Ar Tax), 7.81 (d t, 2H, Ar Tax) $^{13}$C-NMR (CDCl$_3$) δ 19.56 ($\underline{C}$H$_2$SH), 38.15 ($\underline{C}$H$_2$COO), 52.94 ($\underline{C}$HPh), 53.42 ($\underline{C}$HOCO), 74.63 (O$\underline{C}$H$_3$), 126.56-137.39 (Ar Tax), 166.89 ($\underline{C}$OOMe), 168.28 ($\underline{C}$OOCH), 170.41 ($\underline{C}$ONH)

Preparation of PEG-3400 Diacrylamide

Polyethylene glycol mol. wt. 3400 (100 g, 0.05882 mol —OH) was reacted overnight with mesylchloride (13.65 ml, 0.1764 mol, 3 equivalents (eq.)) in the presence of triethylamine (24.58 ml, 3 eq.) in 600 ml toluene/100 ml dichloromethane at room temperature. The product was filtered and recovered by precipitation in diethyl ether. The product was dried in vacuo and was then dissolved in 400 ml 25% ammonium hydroxide solution. This solution was stirred for 3 days at room temperature in a tightly closed bottle. The ammonia was then evaporated by stirring the solution in an open container for 5 days at room temperature. The product was recovered by addition of 1 M sodium hydroxide until a pH of 13 was reached and by three extractions with dichloromethane. The dichloromethane phase was concentrated in vacuo, and the product was precipitated by dropping into diethyl ether. The yield was 80 grams. $^1$H NMR. PEG 3.6 ppm, CH$_2$—C$\underline{H}_2$—NH, 2.85 ppm. The presence of an amine group on the PEG termini was detected by NMR, based on the presence of a triplet at 2.85 ppm, corresponding to the hydrogens on the carbon in the alpha position relative to the amine. By comparison with the PEG backbone peak (3.6 ppm), the product was calculated to contain 99.3% PEG diamine and 0.7% PEG α-monoamine, co-monohydroxyl.

The PEG-3400 diamine (20 g, 11.765 mmol —NH$_2$) was dried by azeotropic distillation in 400 ml toluene and then cooled to room temperature. Dichloromethane (50 mL) was added, and the mixture was cooled in an ice bath. The mixture was reacted overnight with acryloyl chloride (1.43 ml, 17.647 mmol, 1.5 eq.) in the presence of triethylamine (2.46 ml, 17.647 mmol, 1.5 eq.). The solution was filtered and precipitated in diethyl ether. The yield of PEG-3400 diacrylamide was 17 grams.

$^1$H-NMR (DCCl$_3$) δ 3.6 (168H, —C$\underline{H}_2$C$\underline{H}_2$O—), 5.6 (dd, 1H, CH$_2$—C$\underline{H}$—CON—), 6.1, 6.2 (dd, 2.27H, C$\underline{H}_2$—CH—CON—). The infrared spectrum contained amide I & II peaks at 1539.79 and 1673.90 cm$^{-1}$.

Conjugate Addition Reaction Between Methyl Ester of Paclitaxel Side Chain 3-thio-propionate and a PEG-linked Conjugated Saturation To a solution of 10 mg (25 µmol) methyl ester of paclitaxel side chain-2'-O-(3-thio-proprionate) [N-Benzoyl-(2R,3S)-2-O-(3-thio-propionate)-3-phenyl-isoserine methyl ester] and 361 mg (100 µmol) PEG-3400 diacrylamide in 1 ml methanol was added 3.3 µl (25 µmol) triethanolamine. The solution was stirred overnight in the dark under an argon atmosphere. The solvent was removed by a nitrogen gas flow, then the residue was dissolved in 1 ml water and purified using a PD10 column (Pharmacia). The fractions containing PEG were collected and lyophilized. The product was obtained as a white solid with a yield of 329 mg (91% based on PEG-3400 diacrylamide).

Formation of Cross-linked PEG Biomaterial Containing Covalently Bound Methyl Ester of Paclitaxel Side Chain To 1 ml of the mixture of PEG-3400 diacrylamide and PEG-3400 α-monoacrylamide, ω-mono(Paclitaxel side chain methyl ester) from above was added N-vinyl pyrrolidone (3.5 µl) and Eosin Y (10 µL of a 10 mM solution in HEPES buffered saline, pH 7.4). This solution was exposed to visible light at about 500 nm (75 mW/cm$^2$) for 1 minute, producing a cross-linked network.

Alternatively, to 1 ml of the mixture of PEG-3400 diacrylamide and PEG-3400 α-monoacrylamide, ω-mono(Paclitaxel side chain) is added the peptide GCCNNNNNCCG (15.4 mg, 13.8 mol, the sequence of this peptide is designed to provide water solubility) so as to produce a ratio of one thiol to one acrylamide. This solution is incubated at 37° C. for 1 hr for production of a cross-linked network. Gels can be polymerized as spheres by adding 50 µL of the gelling solution containing a 3.5:10 ratio of N-vinyl pyrrolidone to Eosin Y, as described above, to 1 mL of cyclohexane containing 94 mg of Hypermer B239 (ICI Surfactants, Wilmington, Del., USA), with vortexing at 37° C. for 1 hr. Spheres are expected to be produced with diameters ranging from 2 µm to 20 µm.

EXAMPLE 17

Figure 17:
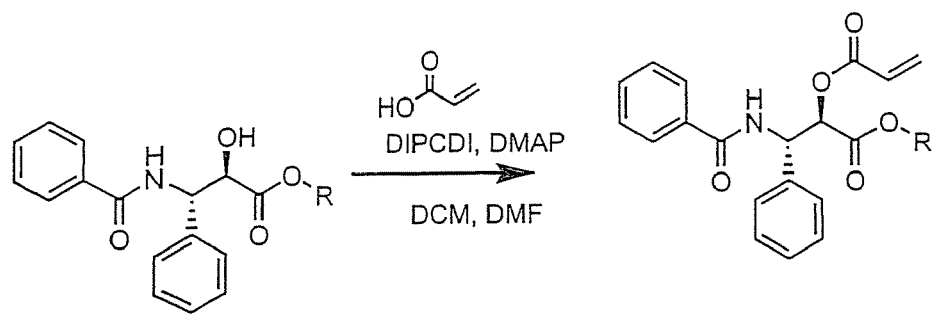
FIG. 17 is a schematic representation of the synthesis route for the modification of paclitaxel (Example 20) or the side chain of paclitaxel (Example 17) with an acrylate. This acrylate is than coupled to a PEG-linked unsaturation through a thiol- or amine-containing linker, and the remaining PEG-linked conjugated unsaturated groups are cross-linked to form a biomaterial.

Formation of a Cross-linked Biomaterial Containing a Modified Version Of the Side Chain of Paclitaxel Coupled to PEG Through a Peptide Linker An acrylate group was attached to the hydroxyl group on the paclitaxel side chain (FIG. 17). A water soluble peptide linker can then be added. If a linker containing a lysine residue were used in this method, then the nucleophilic lysine would increase the rate of hydrolysis of the drug from the biomaterial, or if a linker containing a hydrophobic residue were used, then the rate of hydrolysis would be decreased by the removal of water from the milieu of the ester bond.

Preparation of Methyl Ester of Paclitaxel Side Chain Acrylate (N-Benzoyl-(2R,3S)-2-O-acrylate-3-phenyl-isoserine methyl ester)

A solution of 120 mg (0.4 mmol) N-Benzoyl-(2R,3S)-3-phenyl-isoserine methyl ester and 55 µl (0.8 mmol) acrylic acid in 4 ml dichloromethane and 1 ml DMF was cooled to 0° C. Then 126 µl (0.8 mmol) diisopropylcarbodiimide and a few crystals of dimethylaminopyridine were added and the reaction mixture was stirred at 0° C. for 2 hr. The solvents were removed in vacuo and the crude product dissolved in 50 ml dichloromethane. The organic solution was washed with 1 M KHSO, 5% NaHCO$_3$, and brine and dried over Na$_2$SO$_4$. The pure product was obtained after column chromatography (silica, eluent: ethyl acetate/hexane 1:2 v/v). $^1$H-NMR (CDCl$_3$) δ 3.76 (s, 3H, OC$\underline{H}_3$), 5.53 (d, 1H, C$\underline{H}$O), 5.90 (d d, 1H, C$\underline{H}$Ph), 5.91 (d d, 1H, CHC$\underline{H}_2$), 6.18 (d d, 1H, C$\underline{H}$CH$_2$), 6.45 (d d, 1H, CHC$\underline{H}_2$), 7.06 (d, 1H, NH), 7.29-7.55 (m, 8H, Ar Tax), 7.80 (d t, 2H, Ar Tax) $^{13}$C-NMR (CDCl$_3$) δ 52.87 ($\underline{C}$HOH), 53.56 ($\underline{C}$HPh), 74.44 (O$\underline{C}$H$_3$), 126.63-137.44 (Ar-Tax), 126.97 ($\underline{C}$HCH$_2$), 132.78 (CH$\underline{C}$H$_2$), 164.82 ($\underline{C}$OO Acrylate), 166.84 ($\underline{C}$OOMe), 168.38 ($\underline{C}$ONH)

Preparation of Peptide Linker

A peptide is synthesized using standard Fmoc-based solid phase techniques so as to contain a single deprotected cysteine residue, with the sequence Acetyl-Gly-Cys-Gly-Tyr- Gly-Arg-Gly-Asn-Gln-Cys(tButhio)-NH$_2$. The Cys (tButhio) group is introduced using Fmoc-Cys(tButhio)-OH (Novabiochem). Following cleavage from the resin with 88:5:5:2 trifluoroacetic acid:water:phenol:triisopropylsilane, the peptide is precipitated in diethyl ether and collected by filtration. The crude peptide is purified by semi-preparative scale C18 chromatography, and the identity of the isolated peak is verified by MALDI-TOF mass spectrometry.

Conjugate Addition Reaction Between Methyl Ester of Paclitaxel Side Chain Acrylate and Peptide Linker The methyl ester of paclitaxel side chain acrylate (1.25 mg, 3.68 µmol) is dispersed in 1 ml of 10 µM HEPES buffered saline, containing 115 mM triethanolamine, pH 8, and reacted with the peptide above (8.4 mg, 7.36 µmol) for 1 hr at 37° C. Coupling of the paclitaxel derivative to the peptide is monitored using C18 chromatography and UV detection. Following complete reaction of the peptide with the methyl ester of paclitaxel side chain acrylate via a conjugate addition reaction, dithiothreitol (2.27 mg, 14.72 µmol) is added to the mixture for 1 hr at room temperature to deprotect the tButhio group on the cysteine residue of the peptide. Purification of the peptide linked paclitaxel side chain product is achieved using semi-preparative scale C18 chromatography.

Conjugate Addition Reaction Between Peptide Linker on Modified Paclitaxel Side Chain and a PEG-linked Conjugated Unsaturation The peptide linked paclitaxel side chain product from above (5.45 mg, 3.68 mol) is dispersed in 1 ml of 10 mM HEPES buffered saline, containing 115 mM triethanolamine, pH 8, and reacted with PEG-3400 diacrylamide from Example 16 (100 mg, 29.4 µmol) for 1 hr at 37° C. The product can then be cross-linked as described in Example 16.

EXAMPLE 18

Formation of a Cross-linked Biomaterial Containing the Side Chain of Paclitaxel Coupled to PEG Through an Amine-Containing Linker This example describes the synthesis strategy for methyl ester of paclitaxel side chain-2'-O-3-amino-propionate. The coupling of this modified paclitaxel side chain to a PEG-linked conjugated unsaturation and the cross-linking of this product to form a biomaterial can be performed as described in Example 16 for the corresponding thiol-containing compounds.

Preparation of methyl ester of paclitaxel side chain 3-amino-propionate

Step A) Preparation of a Protected, Modified Paclitaxel Side Chain (N-Benzoyl-(2R,3S)-2-O-(3-Boc-amino-propionate)-3-phenyl-isoserine methyl ester)

This reaction of N-Benzoyl-(2R,3S)-3-phenyl-isoserine methyl ester (0.4 mmol) and 3-Boc-amino-propionic acid (0.8 mmol) in 4 ml dichloromethane can be performed as described for the analogous reaction in Example 16 for the preparation of methyl ester of paclitaxel side chain 3-thio-propionate.

Step B) Preparation to Form Methyl Ester of Paclitaxel Side Chain 3-amino-propionate (N-Benzoyl-(2R,3S)-2-O-(3-amino-propionate)-3-phenyl-isoserine methyl ester)

A saturated solution of HCl in diethyl ether is added to a solution of the Boc-protected compound in dichloromethane, and the reaction mixture is stirred at room temperature for 1 hr. The solvents are removed in vacuo, and the product is obtained as its HCl salt.

EXAMPLE 19

Formation of a Cross-linked Biomaterial Containing Paclitaxel Coupled to PEG Through a Thiol-containing Linker 3-Mercaptoproprionate can be attached to the 2' alcohol on paclitaxel (FIG. 16). This product can then be attached to a PEG-linked conjugated unsaturation (FIG. 16) and cross-linked to form a biomaterial as described in Example 16 for the analogous reaction using compounds having the side chain of paclitaxel.

Preparation of Paclitaxel-2'-O-3-thio-propionate

Step A) Preparation of Protected Paclitaxel-2'-O-3-tritylthio-propionate

A solution of 85 mg (0.1 mmol) paclitaxel and 70 mg (0.2 mmol) 3-tritylthio-propionic acid (from Example 16) in 4 ml dichloromethane is cooled to 0° C. Then 32 µl (0.2 mmol) diisopropylcarbodiimide and a few crystals of dimethylaminopyridine are added, and the reaction mixture is stirred at 0° C. for 2 hr. The solvent is removed in vacuo, and the crude product is dissolved in 50 ml dichloromethane. The organic solution is washed with 1 M KHSO$_4$, 5% NaHCO$_3$, and brine, consecutively, and dried over Na$_7$SO$_4$. The pure product is obtained after column chromatography.

Step B) Deprotection to Form Paclitaxel-2-O-3-thio-propionate

A solution of the trityl protected compound in dichloromethane is added to a solution of TFA, triisopropylsilane, and water (95:2.5:2.5), and the reaction mixture is stirred at room temperature for 1 hr. The solvents are removed in vacuo and the product is obtained after column chromatography.

EXAMPLE 20

Formation of a Cross-linked Biomaterial Containing a Modified Version of Paclitaxel Coupled to PEG Through a Peptide Linker An acrylate group can be attached to the 2' alcohol on paclitaxel (FIG. 17). A water soluble peptide linker can then be added by a conjugate addition reaction, and this product can be coupled to a PEG-linked conjugated unsaturation as described in Example 16 and cross-linked as described in Example 16.

Preparation of Paclitaxel-2'-O-acrylate

A solution of 85 mg (0.1 mmol) paclitaxel and 70 mg (0.2 mmol) acrylic acid in 4 ml dichloromethane is cooled to 0° C. Then 32 µl (0.2 mmol) diisopropylcarbodiimide and a few crystals of dimethylaminopyridine are added, and the reaction mixture is stirred at 0° C. for 2 hr. The solvent is removed in vacuo, and the crude product is dissolved in 50 ml dichloromethane. The organic solution is washed with 1 M KHSO$_4$, 5% NaHCO$_3$, brine and dried over Na$_2$SO$_4$. The pure product is obtained after column chromatography.

EXAMPLE 21

Formation of a Cross-linked Biomaterial Containing Doxorubicin Coupled to PEG Through a Thiol-containing Linker As described for paclitaxel, the drug doxorubicin can be modified with a thiol-containing linker. The attachment of this product to a PEG-linked conjugated unsaturation and the cross-linking of the remaining conjugated unsaturated groups to form a biomaterial can be performed as described in Example 19 for the paclitaxel derivative.

Preparation of doxorubicin-O-3-thio-propionate

Step A) Preparation of N-Boc-Doxorubicin

A solution of 116 mg (0.2 mmol) doxorubicin HCl in 1 M NaOH is stirred and cooled in an ice-bath. A solution of 48 mg (0.22 mmol) di-tert-butyl dicarbonate in dioxane is added, and the reaction mixture is stirred for 2 hr at room temperature. The dioxane is removed in vacuo, and the aqueous solution is acidified with 1 M $KHSO_4$ to pH 2-3. The aqueous solution is extracted with ethyl acetate. The organic phase is washed with brine, dried over $Na_2SO_4$, and concentrated in vacuo.

Step B) Preparation of N-Boc-Doxorubicin-O-3-tritylthio-propionate

The reaction of N-Boc-doxorubicin (0.2 mmol) and 3-tritylthio-propionic acid (0.1 mmol) in dichloromethane using diisopropylcarbodiimide (0.1 mmol) and dimethylaminopyridine can be performed as described in Step A of Example 19 for paclitaxel instead of N-Boc-doxorubicin.

Step C) Deprotection to Form doxorubicin-O-3-thio-propionate

The deprotection of the N-Boc protected compound is analogous to Step B of Example 19 for the deprotection of the trityl protected paclitaxel derivative.

EXAMPLE 22

Formation of a Cross-linked Biomaterial Containing Methoxyestradiol Coupled to PEG Through a Thiol-containing Linker Thiolated 2-methoxyestradiol can be synthesized as described below. This compound can then be incorporated into a biomaterial as described in Examples 19 and 21 for paclitaxel and doxorubicin.

Preparation of thiolated 2-methoxyestradiol

The reaction of 2-methoxyestradiol (0.5 mmol) and 3-tritylthio-propionic acid (0.25 mmol) in dichloromethane using diisopropylcarbodiimide (0.25 mmol) and dimethylaminopyridine can be performed as described in Step A in Example 19 using for paclitaxel. The deprotection of this trityl protected compound is analogous to Step B in Example 19 for the deprotection of the trityl protected paclitaxel derivative.

EXAMPLE 23

Incorporation of a Thiol-containing Peptide into a Biomaterial and the Kinetics of Release of the Modified Peptide from the Biomaterial A therapeutic peptide that is known to affect cell adhesion to basement membrane was coupled to a PEG-linked conjugated unsaturation. The coupling occurred due to the addition of a single cysteine residue to the active peptide sequence. Upon release of the peptide from the cross-linked biomaterial, the original peptide was not regenerated, because the thiol of the cysteine residue was modified with propionic acid. However, the nature of this and other peptide therapeutics is such that the activity of the peptide should be unaffected by the presence of this modified cysteine at the end of the peptide.

Preparation of Peptide

A peptide, containing a single cysteine residue, was synthesized using standard Fmoc-based solid phase techniques with the sequence Acetyl-Gly-Cys-Gly-Tyr-Gly-Arg-Gly-Asp-Ser-Pro-$NH_2$. Following cleavage from the resin with 88:5:5:2 trifluoroacetic acid:water:phenol:triisopropylsilane, the peptide was precipitated in diethyl ether and collected by filtration. The crude peptide was purified by semi-preparative scale C18 chromatography, and the identity of the isolated peak was verified by MALDI-TOF mass spectrometry.

Preparation of Polyethylene Glycol Diacrylate

Polyethylene glycol mol. wt. 3400 (PEG-3400, 20 g, 11.765 mmol —OH) was dried by azeotropic distillation in toluene and cooled to room temperature. Dichloromethane was added to produce a clear solution at 0° C. The mixture was cooled in an ice bath and reacted overnight with acryloyl chloride (1.43 ml, 17.647 mmol, 1.5 eq.) in the presence of triethylamine (2.46 ml, 17.647 mmol, 1.5 eq.). The solution was filtered and precipitated in diethyl ether. Polyethylene glycol-3400 diacrylate was obtained with a yield of 17 g.

Conjugated Addition Reaction Between Peptide and a PEG Linked Conjugated Unsaturation The peptide (3.92 mg, 3.68 µmol) was dissolved in 115 µl 1 mM MES buffered saline, pH 5.8 and mixed with 870 µl PEG-3400 diacrylamide (100 mg, 29.4 µmol from Example 16) dissolved in 10 mM HEPES buffered saline, pH 8, containing 115 mM triethanolamine, and allowed to sit for 10 min at 37° C. Complete coupling of the peptide to the modified PEG was verified using Ellman's reagent.

Formation of Cross-linked PEG Biomaterial Containing Covalently Bound Peptide

To facilitate the photopolymerization/photocross-linking of the above peptide and PEG diacrylamide solution, N-vinyl pyrrolidone (3.5 µl) and Eosin Y (10 µl of a 10 mM solution in HEPES buffered saline, pH 7.4) were added. The solution was exposed to visible light at about 500 mm (75 mW/$cm^2$) for 1 minute, producing a cross-linked network containing hydrolyzable peptide. The release of the peptide from the material was monitored using C18 chromatography. After 10 days at pH 7.4, 37° C., about ⅓ of the peptide had been released from the material.

Kinetics of Release of the Modified Peptide from the Biomaterial

To study hydrolytic release of the peptide from the polymer, the peptide (15.7 mg, 14.71 µmol) was dissolved in 115 µl 1 mM MES buffered saline, pH 5.8, and the presence of a free thiol in the peptide was verified by Ellman's reagent. PEG-3400 diacrylate (100 mg, 29.41 µmol) was dissolved in 885 µl 10 mM HEPES buffered saline, pH 8, containing 115 mM triethanolamine. The attachment of the peptide to the PEG was followed using C18 chromatography. A gradient from 95% water with 0.1% TFA/5% acetonitrile to 40% water with 0.1% TFA/60% acetonitrile was used. The free peptide eluted at about 20% acetonitrile, and the PEG diacrylate eluted at about 40% acetonitrile. Within 10 min of mixing the peptide and the PEG diacrylate, the peptide peak was no longer observed, and the peptide-related absorbance at 273 nm was found to coelute with the PEG diacrylate. MALDI-TOF mass spectrometry verified that the peptide was coupled to the PEG. The mixture was then incubated at pH 8, 37° C., and the release of the peptide from the PEG was followed by the appearance of a peak that eluted at 20% acetonitrile. MALDI-TOF mass spectrometry analysis of this peak showed that it contained a compound with a molecular weight equal to that of the original peptide plus 72 mass units, indicating that the peptide was now modified with propionic acid. This result indicates that the thiol in the cysteine-containing peptide had reacted with the acrylate group on the PEG through a conjugate addition reaction and that the modified peptide was released due to hydrolysis of the ester bond between the modified peptide and the PEG. The rate of release of the modified peptide was measured, giving a half-life of 4.86 days for the release of the modified peptide at 37° C., pH 8. Based on the predicted pH dependence of this hydrolysis, the half-life for release at 37° C. is about three weeks at pH 7.4.

The rate of hydrolysis of PEG-3400 diacrylate in 10 mM HEPES buffered saline, pH 8, containing 115 mM triethanolamine was also measured. Acrylic acid was found to hydrolyze from PEG-3400 diacrylate with a half-life of 24 days at 37° C., pH 8.0 indicating a half-life for release of about three months at 37° C., pH 7.4.

EXAMPLE 24

Incorporation of a Thiolated Oligonucleotide into a Biomaterial and the Kinetics of Release of Thiolated Oligonucleotide from the Biomaterial This example describes a method for the incorporation of a thiolated oligonucleotide into a biomaterial and measuring the rate of release of the oligonucleotide due to hydrolysis of the biomaterial. An oligonucleotide containing a single thiol group is custom synthesized (Synthegen, LLC, Houston, Tex., USA). The oligonucleotide (3.675 µmol) is added to 100 mg PEG diacrylate from Example 23 (29.4 µmol) in 1 ml of 10 mM HEPES buffered saline with 115 mM triethanolamine, pH 8. After 15 minutes, N-vinyl pyrrolidone (3.5 µl) and Eosin Y (10 µl of a 10 mM solution in HEPES buffered saline, pH 7.4) are added to the solution. This solution is exposed to visible light at about 500 m (75 mW/cm$^2$) for 1 minute for production of a cross-linked network containing the oligonucleotide. The hydrolysis of the release of the thiolated oligonucleotide modified with propionic acid into the buffered water surrounding the material can be monitored by UV adsorption at 260 nm.

EXAMPLE 25

Formation of Colloidal Biomaterials

This example describes a method of producing a colloidal biomaterial via conjugate addition reactions. A colloidal biomaterial refers to a large copolymer of dimension greater than 5 nm and smaller than 1 µm. The colloidal biomaterial can contain molecules, such as peptides, that target the colloid to cells.

A mixture (1 mL) of PEG-3400 diacrylamide and PEG-3400 α-monoacrylamide, ω-mono(paclitaxel side chain methyl ester) (Example 16) is incubated at 37° C. for 1 hour. The peptide GCNNRGDNNCG (31.0 mg, 27.6 mol), which contains an RGD sequence for targeting to cells, can also be included in this mixture at a ratio of one thiol to one acrylamide. This method is expected to produce a linear high molecular weight copolymer of PEG-3400 and peptide which is end capped with PEG-3400 mono(paclitaxel side chain methyl ester) that can be formulated as an injectable composition.

Other Embodiments

From the foregoing description, it will be apparent that variations and modifications may be made to the invention described herein to adopt it to various usages and conditions. Such embodiments are also within the scope of the following claims. In addition, the use of an amine as a biomaterial precursor component is an embodiment which falls within the scope of the following claims.

All publications and patents mentioned in this specification are herein incorporated by reference to the same extent as if each individual publication or patent was specifically and individually indicated to be incorporated by reference.

What is claimed is:

1. A biomaterial comprising a pharmaceutically active moiety, a water-soluble or water-swellable polymer, and a linker comprising a thioether or secondary amine, wherein said linker connects said pharmaceutically active moiety and said polymer, and said pharmaceutically active moiety is connected to said linker via an ester or amide bond, said bond having a half-life of between 1 hour and 1 year in an aqueous solution at pH 7.4 and 37° C.

2. The biomaterial of claim 1, wherein the half-life of the ester or amide bond is between 1 day and 9 months in an aqueous solution at pH 7.4 and 37° C.

3. The biomaterial of claim 1, wherein the half-life of the ester or amide bond is between 2 days and 6 months, in an aqueous solution at pH 7.4 and 37° C.

4. The biomaterial of claim 1, wherein the half-life of the ester or amide bond is between 4 days and 3 weeks, in an aqueous solution at pH 7.4 and 37° C.

5. The biomaterial of claim 1, wherein said pharmaceutically active moiety is derived from one of the group consisting of synthetic organic molecules, naturally occurring organic molecules, nucleic acid molecules, biosynthetic proteins or peptides, naturally occurring peptides or proteins, and modified naturally occurring peptides or proteins.

6. The biomaterial of claim 1, wherein said pharmaceutically active moiety is derived from paclitaxel, doxorubicin, 5-fluorodeoxyuridine, estradiol, or 2-methoxyestradiol.

7. The biomaterial of claim 1, wherein said pharmaceutically active moiety connected to said linker has the formula:

D-Y—C(O)—$(CH_2)_n$—S—$(CH_2)_2$—COX—,

D-Y—C(O)—$(CH_2)_n$—NH—$(CH_2)_2$—COX—,

D-Y—C(O)—$(CH_2)_n$—NH—U—,

D-Y—C(O)—$(CH_2)_n$—S—U—,

D-Y—C(O)—$(CH_2)_2$—S-L-S—$CH_2$—$CH_2$—CO—X—,

D-Y—C(O)—$(CH_2)_2$—S-L-S—U—,

D-Y—C(O)—$(CH_2)_2$—NH-L-S—$CH_2$—$CH_2$—CO—X—,

D-Y—C(O)—$(CH_2)_2$—NH-L-S—U—,

D-Y—C(O)—$(CH_2)_2$—$CH_2$—$CH_2$—CO—X—,

D-Y—C(O)—$(CH_2)_2$—S-L-NH—U—,

D-Y—C(O)—$(CH_2)_2$—NH-L-NH—$CH_2$—$CH_2$—CO—X—, or

D-Y—C(O)—$(CH_2)_2$—NH-L-NH—U—, wherein D said pharmaceutically active moiety; Y is O, NH, or N; L is a linear or branched moiety; X is O or N; n is 1 or 2, and U is the product of the addition of a nucleophile to an electrophilic group that is attached to said water-soluble or water-swellable polymer.

8. The biomaterial of claim 1, wherein said water-soluble or water-swellable polymer is selected from the group consisting of poly(ethylene glycol), poly(ethylene oxide), poly(vinyl alcohol), poly(acrylic acid), poly(ethylene-co-vinyl alcohol), poly(vinyl pyrrolidone), poly(acrylic acid), poly(ethyloxazoline), poly(ethylene oxide)-co-poly(propylene oxide) block copolymers, or water-soluble or water-swellable copolymers comprising these polymers, and their derivatives comprising conjugated unsaturated groups.

9. The biomaterial of claim 1, wherein said linker comprises a hydrocarbon moiety containing between 1 and 4 carbon atoms, inclusive.

10. A biomaterial comprising a first component cross-linked to a second component, wherein (i) said first component comprises a first pharmaceutically active moiety, a first water-soluble or water-swellable polymer, and a first linker comprising a thioether or secondary amine, wherein said linker connects said pharmaceutically active moiety and said polymer, and said pharmaceutically active moiety is connected to said linker via a first ester or amide bond, said first bond having a half life of between 1 hour and 1 year in an aqueous solution at pH 7.4 and 37° C.; and (ii) said second component comprises a second pharmaceutically active moiety, a second water-soluble or water-swellable polymer, and a second linker comprising a thioether or secondary amine, wherein said linker connects said pharmaceutically active moiety and said polymer, and said pharmaceutically active moiety is connected to said linker via a second ester or amide bond, said second bond having a half-life of between 1 hour and 1 year in an aqueous solution at pH 7.4 and 37° C., wherein said first and second components are the same or different.

11. The biomaterial of claim 10, wherein said first and second components are cross-linked with a third polymer that comprises two or more conjugated unsaturated groups but does not comprise a pharmaceutically active moiety.

12. The biomaterial of claim 10, wherein said first and second components are cross-linked with a linker comprising two or more nucleophilic groups.

13. The biomaterial of claim 10, wherein said first or second water-soluble or water-swellable polymer is selected from the group consisting of poly(ethylene glycol), poly(ethylene oxide), poly(vinyl alcohol), poly(acrylic acid), poly(ethylene-co-vinyl alcohol), poly(vinyl pyrrolidone), poly(acrylic acid), poly(ethyloxazoline), poly(ethylene oxide)-co-poly(propylene oxide) block copolymers, or water-soluble or water-swellable copolymers comprising these polymers, and their derivatives comprising conjugated unsaturated groups.

14. The biomaterial of claim 10, wherein said first or second polymer, prior to being cross-linked, comprises one or more conjugated unsaturated groups.

15. The biomaterial of claim 14, wherein said conjugated unsaturated groups are selected from the group consisting of acrylates, methacrylates, acrylamides, methacrylamides, acrylonitiriles, and quinones.

16. The biomaterial of claim 10, wherein said first or second linker comprises an adhesion site, growth factor binding site, protease binding site, or enzymatically degradable site.

17. The biomaterial of claim 10, wherein the half life of said first or second ester or amide bond is between 1 day and 9 months in an aqueous solution at pH 7.4 and 37° C.

18. The biomaterial of claim 10, wherein the half life of said first or second ester or amide bond is between 2 days and 6 months, in an aqueous solution at pH 7.4 and 37° C.

19. The biomaterial of claim 10, wherein the half life of the ester or amide bond is between 4 days and 3 weeks, in an aqueous solution at pH 7.4 and 37° C.

20. The biomaterial of claim 10, wherein said pharmaceutically active moiety is derived from one of the group consisting of synthetic organic molecules, naturally occurring organic molecules, nucleic acid molecules, biosynthetic proteins or peptides, naturally occurring peptides or proteins, and modified naturally occurring peptides or proteins.

21. The biomaterial of claim 10, wherein said pharmaceutically active moiety is derived from paclitaxel, doxorubicin, 5-fluorodeoxyuridine, estradiol, or 2-methoxyestradiol.

22. The biomaterial of claim 10, wherein said first and second components have the formula:

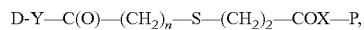

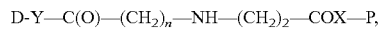

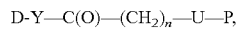

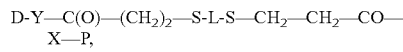

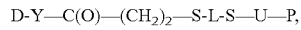

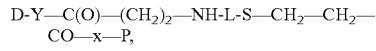

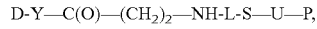

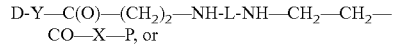

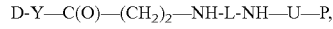

wherein D is said first or second pharmaceutically active moiety; Y is O, NH, or N; L is a linear or branched moiety; X is O or N; P is said first or second water-soluble polymer or a water-swellable polymer further comprising one or more conjugated unsaturated groups; n is 1 or 2, and U is the product of the addition of a nucleophile to an electrophilic group that is attached to said first or second polymer.

23. The biomaterial of claim 10, wherein said first or second linker comprises a hydrocarbon moiety containing between 1 and 4 carbon atoms, inclusive.

24. The biomaterial of claim 1, wherein said linker comprises said thioether.

25. The biomaterial of claim 1, wherein said linker comprises said secondary amine.

26. The biomaterial of claim 10, wherein said first linker or said second linker comprises said thioether.

27. The biomaterial of claim 10, wherein said first linker or said second linker comprises said secondary amine.

* * * * *

SEQUENCE LISTING

```
<160> NUMBER OF SEQ ID NOS: 75

<210> SEQ ID NO 1
<211> LENGTH: 10
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (1)...(10)
<223> OTHER INFORMATION: Xaa=any amino acid except Cys

<400> SEQUENCE: 1

Tyr Cys Xaa Xaa Xaa Xaa Xaa Xaa Cys Tyr
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
```

```
<222> LOCATION: (1)...(8)
<223> OTHER INFORMATION: Xaa=any amino acid except Cys

<400> SEQUENCE: 2

Cys Xaa Xaa Xaa Xaa Xaa Xaa Cys
 1               5

<210> SEQ ID NO 3
<211> LENGTH: 6
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (1)...(6)
<223> OTHER INFORMATION: Xaa=any amino acid except Cys

<400> SEQUENCE: 3

Xaa Xaa Xaa Xaa Xaa Xaa
 1               5

<210> SEQ ID NO 4
<211> LENGTH: 13
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (1)...(13)
<223> OTHER INFORMATION: Xaa=any amino acid except Cys

<400> SEQUENCE: 4

Cys Xaa Xaa Xaa Xaa Xaa Cys Xaa Xaa Xaa Xaa Xaa Cys
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (1)...(7)
<223> OTHER INFORMATION: Xaa=any amino acid except Cys

<400> SEQUENCE: 5

Cys Xaa Xaa Xaa Xaa Xaa Cys
 1               5

<210> SEQ ID NO 6
<211> LENGTH: 13
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (2)...(6)
<223> OTHER INFORMATION: Xaa=any amino acid except Cys or Tyr
<220> FEATURE:
<221> NAME/KEY: VARIANT
<222> LOCATION: (8)...(12)
<223> OTHER INFORMATION: Xaa=any amino acid except Cys or Tyr
<220> FEATURE:
<221> NAME/KEY: MOD_RES
<222> LOCATION: 1
<223> OTHER INFORMATION: Xaa=acetylated Tyrosine
```

```
<400> SEQUENCE: 6

Xaa Xaa Xaa Xaa Xaa Xaa Tyr Xaa Xaa Xaa Xaa Xaa Tyr
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (1)...(5)
<223> OTHER INFORMATION: Xaa=any amino acid except Cys or Tyr

<400> SEQUENCE: 7

Xaa Xaa Xaa Xaa Xaa
 1               5

<210> SEQ ID NO 8
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 8

Gly Pro Arg Val Val Glu
 1               5

<210> SEQ ID NO 9
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 9

Asn Asn Arg Asp Asn Thr
 1               5

<210> SEQ ID NO 10
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 10

Tyr Asn Arg Val Ser Glu
 1               5

<210> SEQ ID NO 11
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 11

Gln Met Arg Met Glu Leu
 1               5

<210> SEQ ID NO 12
<211> LENGTH: 6
<212> TYPE: PRT
<213> ORGANISM: Artificial Sequence
```

```
<220> FEATURE:
<223> OTHER INFORMATION: Based on Homo sapiens

<400> SEQUENCE: 12

Gly Phe Arg His Arg His
1               5

<210> SEQ ID NO 13
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 13

Gly Tyr Arg Ala Arg Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 14

Tyr Gln Lys Asn Asn Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 15

Leu Ile Lys Met Lys Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 16

Asn Phe Lys Ser Gln Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 17

Glu Trp Lys Ala Leu Thr
1               5

<210> SEQ ID NO 18
<211> LENGTH: 6
<212> TYPE: PRT
<213> ORGANISM: Artificial Sequence
<220> FEATURE:
```

<223> OTHER INFORMATION: Based on Homo sapiens

<400> SEQUENCE: 18

Ser Tyr Lys Met Ala Asp
1               5

<210> SEQ ID NO 19
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 19

Thr Gln Lys Lys Val Glu
1               5

<210> SEQ ID NO 20
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 20

Arg Gln Lys Gln Val Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 21

Gln Val Lys Asp Asn Glu
1               5

<210> SEQ ID NO 22
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 22

Leu Ile Lys Ala Ile Gln
1               5

<210> SEQ ID NO 23
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 23

Thr Leu Lys Ser Arg Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Based on Homo sapiens -continued

```
<400> SEQUENCE: 24

Ser Arg Lys Met Leu Glu
1               5

<210> SEQ ID NO 25
<211> LENGTH: 6
<212> TYPE: PRT
<213> ORGANISM: Artificial Sequence
<220> FEATURE:
<223> OTHER INFORMATION: Based on Homo sapiens, Bos taurus and Gallus
      gallus

<400> SEQUENCE: 25

Pro Gln Gly Ile Ala Gly
1               5

<210> SEQ ID NO 26
<211> LENGTH: 6
<212> TYPE: PRT
<213> ORGANISM: Bos taurus

<400> SEQUENCE: 26

Pro Gln Gly Leu Leu Gly
1               5

<210> SEQ ID NO 27
<211> LENGTH: 6
<212> TYPE: PRT
<213> ORGANISM: Gallus gallus

<400> SEQUENCE: 27

Pro Gln Gly Ile Leu Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Based on Gallus gallus and Homo sapiens

<400> SEQUENCE: 28

Pro Gln Gly Leu Ala Gly
1               5

<210> SEQ ID NO 29
<211> LENGTH: 6
<212> TYPE: PRT
<213> ORGANISM: Homo sapiens

<400> SEQUENCE: 29

Pro Leu Gly Ile Ala Gly
1               5

<210> SEQ ID NO 30
<211> LENGTH: 6
<212> TYPE: PRT
<213> ORGANISM: Homo sapiens

<400> SEQUENCE: 30

Pro Leu Gly Leu Trp Ala
1               5

<210> SEQ ID NO 31
```

```
<211> LENGTH: 6
<212> TYPE: PRT
<213> ORGANISM: Homo sapiens

<400> SEQUENCE: 31

Pro Leu Gly Leu Ala Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 32

Gly Pro Gln Gly Ile Ala Gly Gln
1               5

<210> SEQ ID NO 33
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 33

Gly Pro Val Gly Ile Ala Gly Gln
1               5

<210> SEQ ID NO 34
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 34

Gly Pro Gln Gly Val Ala Gly Gln
1               5

<210> SEQ ID NO 35
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 35

Gly Pro Gln Gly Arg Ala Gly Gln
1               5

<210> SEQ ID NO 36
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 36

Gly Pro Gln Gly Ile Ala Ser Gln
1               5

<210> SEQ ID NO 37
<211> LENGTH: 8
<212> TYPE: PRT
<213> ORGANISM: Artificial Sequence
```

```
<220> FEATURE:
<223> OTHER INFORMATION: Based on Homo sapiens

<400> SEQUENCE: 37

Gly Pro Gln Gly Ile Phe Gly Gln
 1               5

<210> SEQ ID NO 38
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 38

Gly Pro Gln Gly Ile Trp Gly Gln
 1               5

<210> SEQ ID NO 39
<211> LENGTH: 4
<212> TYPE: PRT
<213> ORGANISM: Artificial Sequence
<220> FEATURE:
<223> OTHER INFORMATION: Based on Homo sapiens

<400> SEQUENCE: 39

Arg Gly Asp Ser
 1

<210> SEQ ID NO 40
<211> LENGTH: 4
<212> TYPE: PRT
<213> ORGANISM: Artificial Sequence
<220> FEATURE:
<223> OTHER INFORMATION: Based on Homo sapiens

<400> SEQUENCE: 40

Arg Glu Asp Val
 1

<210> SEQ ID NO 41
<211> LENGTH: 4
<212> TYPE: PRT
<213> ORGANISM: Artificial Sequence
<220> FEATURE:
<223> OTHER INFORMATION: Based on Homo sapiens

<400> SEQUENCE: 41

Arg Gly Asp Val
 1

<210> SEQ ID NO 42
<211> LENGTH: 5
<212> TYPE: PRT
<213> ORGANISM: Artificial Sequence
<220> FEATURE:
<223> OTHER INFORMATION: Based on Homo sapiens

<400> SEQUENCE: 42

Leu Arg Gly Asp Asn
 1               5

<210> SEQ ID NO 43
<211> LENGTH: 5
<212> TYPE: PRT
<213> ORGANISM: Artificial Sequence
<220> FEATURE:
```

-continued

<223> OTHER INFORMATION: Based on Homo sapiens

<400> SEQUENCE: 43

Ile Lys Val Ala Val
1               5

<210> SEQ ID NO 44
<211> LENGTH: 5
<212> TYPE: PRT
<213> ORGANISM: Artificial Sequence
<220> FEATURE:
<223> OTHER INFORMATION: Based on Homo sapiens

<400> SEQUENCE: 44

Tyr Ile Gly Ser Arg
1               5

<210> SEQ ID NO 45
<211> LENGTH: 5
<212> TYPE: PRT
<213> ORGANISM: Artificial Sequence
<220> FEATURE:
<223> OTHER INFORMATION: Based on Homo sapiens

<400> SEQUENCE: 45

Pro Asp Ser Gly Arg
1               5

<210> SEQ ID NO 46
<211> LENGTH: 10
<212> TYPE: PRT
<213> ORGANISM: Artificial Sequence
<220> FEATURE:
<223> OTHER INFORMATION: Based on Homo sapiens

<400> SEQUENCE: 46

Arg Asn Ile Ala Glu Ile Ile Lys Asp Ala
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Based on Homo sapiens

<400> SEQUENCE: 47

Arg Gly Asp Thr
1

<210> SEQ ID NO 48
<211> LENGTH: 4
<212> TYPE: PRT
<213> ORGANISM: Artificial Sequence
<220> FEATURE:
<223> OTHER INFORMATION: Based on Homo sapiens

<400> SEQUENCE: 48

Asp Gly Glu Ala
1

<210> SEQ ID NO 49
<211> LENGTH: 4
<212> TYPE: PRT
<213> ORGANISM: Artificial Sequence
<220> FEATURE:
<223> OTHER INFORMATION: Based on Homo sapiens

```
<220> FEATURE:
<221> NAME/KEY: VARIANT
<222> LOCATION: (1)...(4)
<223> OTHER INFORMATION: Xaa=any amino acid

<400> SEQUENCE: 49

Val Thr Xaa Gly
 1

<210> SEQ ID NO 50
<211> LENGTH: 6
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: 1,4,6
<223> OTHER INFORMATION: Xaa=Met, Leu, Ala, Ile, Val, Phe, or Pro
<220> FEATURE:
<221> NAME/KEY: VARIANT
<222> LOCATION: 2,3,5
<223> OTHER INFORMATION: Xaa=Arg or Lys

<400> SEQUENCE: 50

Xaa Xaa Xaa Xaa Xaa Xaa
 1               5

<210> SEQ ID NO 51
<211> LENGTH: 6
<212> TYPE: PRT
<213> ORGANISM: Artificial Sequence
<220> FEATURE:
<223> OTHER INFORMATION: Based on Homo sapiens

<400> SEQUENCE: 51

Pro Arg Arg Ala Arg Val
 1               5

<210> SEQ ID NO 52
<211> LENGTH: 19
<212> TYPE: PRT
<213> ORGANISM: Artificial Sequence
<220> FEATURE:
<223> OTHER INFORMATION: Based on Homo sapiens

<400> SEQUENCE: 52

Tyr Glu Lys Pro Gly Ser Pro Pro Arg Glu Val Val Pro Arg Pro Arg
 1               5                  10                  15

Pro Gly Val

<210> SEQ ID NO 53
<211> LENGTH: 28
<212> TYPE: PRT
<213> ORGANISM: Artificial Sequence
<220> FEATURE:
<223> OTHER INFORMATION: Based on Homo sapiens

<400> SEQUENCE: 53

Arg Pro Ser Leu Ala Lys Lys Gln Arg Phe Arg His Arg Asn Arg Lys
 1               5                  10                  15

Gly Tyr Arg Ser Gln Arg Gly His Ser Arg Gly Arg
            20                  25

<210> SEQ ID NO 54
<211> LENGTH: 17
<212> TYPE: PRT
```

<213> ORGANISM: Artificial Sequence
<220> FEATURE:
<223> OTHER INFORMATION: Based on Homo sapiens

<400> SEQUENCE: 54

Arg Ile Gln Asn Leu Leu Lys Ile Thr Asn Leu Arg Ile Lys Phe Val
1               5                   10                  15
Lys

<210> SEQ ID NO 55
<211> LENGTH: 14
<212> TYPE: PRT
<213> ORGANISM: Artificial Sequence
<220> FEATURE:
<223> OTHER INFORMATION: Based on Homo sapiens
<220> FEATURE:
<221> NAME/KEY: MOD_RES
<222> LOCATION: 2
<223> OTHER INFORMATION: Xaa=bAla

<400> SEQUENCE: 55

Lys Xaa Phe Ala Lys Leu Ala Ala Arg Leu Tyr Arg Lys Ala
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Based on Homo sapiens

<400> SEQUENCE: 56

Lys His Lys Gly Arg Asp Val Ile Leu Lys Lys Asp Val Arg
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Based on Homo sapiens

<400> SEQUENCE: 57

Tyr Lys Lys Ile Ile Lys Lys Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Based on Homo sapiens

<400> SEQUENCE: 58

Gly Cys Tyr Lys Asn Arg Asp Cys Gly
1               5

<210> SEQ ID NO 59
<211> LENGTH: 16
<212> TYPE: PRT
<213> ORGANISM: Artificial Sequence
<220> FEATURE:
<223> OTHER INFORMATION: Based on Homo sapiens

<400> SEQUENCE: 59

Gly Cys Asp Asp Gly Pro Gln Gly Ile Trp Gly Gln Asp Asp Cys Gly
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Based on Homo sapiens

<400> SEQUENCE: 60

Gly Cys Arg Asp Gly Pro Gln Gly Ile Trp Gly Gln Asp Arg Cys Gly
1               5                   10                  15

<210> SEQ ID NO 61
<211> LENGTH: 11
<212> TYPE: PRT
<213> ORGANISM: Artificial Sequence
<220> FEATURE:
<223> OTHER INFORMATION: Based on Homo sapiens

<400> SEQUENCE: 61

Gly Cys Gly Tyr Gly Arg Gly Asp Ser Pro Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Based on Homo sapiens
<220> FEATURE:
<221> NAME/KEY: MOD_RES
<222> LOCATION: 1
<223> OTHER INFORMATION: Xaa=acetylated Gly

<400> SEQUENCE: 62

Xaa Cys Gly Tyr Gly Arg Gly Asp Ser Pro
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Based on Homo sapiens

<400> SEQUENCE: 63

Gly Asp Gly Ser Gly Tyr Gly Arg Gly Asp Ser Pro Gly
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Based on Homo sapiens

<400> SEQUENCE: 64

Gly Cys Gly Tyr Gly Arg Gly Asp Ser
1               5

<210> SEQ ID NO 65
<211> LENGTH: 14
<212> TYPE: PRT
<213> ORGANISM: Artificial Sequence
<220> FEATURE:
<223> OTHER INFORMATION: Based on Homo sapiens

<400> SEQUENCE: 65

```
Gly Lys Lys Lys Lys Gly Cys Tyr Lys Asn Arg Asp Cys Gly
1               5                   10
```

<210> SEQ ID NO 66
<211> LENGTH: 9
<212> TYPE: PRT
<213> ORGANISM: Artificial Sequence
<220> FEATURE:
<223> OTHER INFORMATION: Based on Homo sapiens

<400> SEQUENCE: 66

```
Gly Cys Tyr Lys Asn Arg Asp Cys Gly
1               5
```

<210> SEQ ID NO 67
<211> LENGTH: 13
<212> TYPE: PRT
<213> ORGANISM: Artificial Sequence
<220> FEATURE:
<223> OTHER INFORMATION: Based on Homo sapiens

<400> SEQUENCE: 67

```
Gly Cys Cys Gly His His His His His Gly Cys Cys Gly
1               5                   10
```

<210> SEQ ID NO 68
<211> LENGTH: 11
<212> TYPE: PRT
<213> ORGANISM: Artificial Sequence
<220> FEATURE:
<223> OTHER INFORMATION: Based on Homo sapiens

<400> SEQUENCE: 68

```
Gly Cys Gly Tyr Gly Arg Asp Gly Ser Pro Gly
1               5                   10
```

<210> SEQ ID NO 69
<211> LENGTH: 156
<212> TYPE: PRT
<213> ORGANISM: Artificial Sequence
<220> FEATURE:
<223> OTHER INFORMATION: Based on Homo sapiens

<400> SEQUENCE: 69

```
Met Gly Ser Ser His His His His His His Ser Ser Gly Leu Val Pro
1               5                   10                  15

Arg Gly Ser His Met Lys Asp Pro Lys Arg Leu Tyr Arg Ser Arg Lys
            20                  25                  30

Leu Pro Val Glu Leu Glu Ser Ser His Pro Ile Phe His Arg Gly
        35                  40                  45

Glu Phe Ser Val Cys Asp Ser Val Ser Trp Val Gly Asp Lys Thr
    50                  55                  60

Thr Ala Thr Asp Ile Lys Gly Lys Glu Val Met Val Leu Gly Glu Val
65                  70                  75                  80

Asn Ile Asn Asn Ser Val Phe Lys Gln Tyr Phe Phe Glu Thr Lys Cys
                85                  90                  95

Arg Asp Pro Asn Pro Val Asp Ser Gly Cys Arg Gly Ile Asp Ser Lys
            100                 105                 110

His Trp Asn Ser Tyr Cys Thr Thr Thr His Thr Phe Val Lys Ala Leu
        115                 120                 125

Thr Met Asp Gly Lys Gln Ala Ala Trp Arg Phe Ile Arg Ile Asp Thr
    130                 135                 140
```

Ala Cys Val Cys Val Leu Ser Arg Lys Ala Val Arg
145                 150                 155

<210> SEQ ID NO 70
<211> LENGTH: 432
<212> TYPE: DNA
<213> ORGANISM: Artificial Sequence
<220> FEATURE:
<223> OTHER INFORMATION: Based on Homo sapiens

<400> SEQUENCE: 70
gaattcccat ggcatatgaa agacccgaaa cgtctgtacc gttctcgtaa actgcccgtg      60
gaactcgaga gctcttccca cccgattttc catcgtggcg agttctccgt gtgtgactct     120
gtctctgtat gggtaggcga taaaaccact gccactgata tcaaaggcaa agaggtgatg     180
gtgctgggag aagtaaacat taacaactct gtattcaaac agtacttctt cgaaactaag     240
tgccgtgacc cgaaccccggt agactctggg tgtcgcggca tcgattctaa acactggaac     300
tcttactgca ccactactca cactttcgtt aaagcgttga ctatggatgg taaacaggct     360
gcctggcgtt tcatccgtat cgatactgca tgcgtgtgtg tactgtcccg taaagctgtt     420
cgttaaggat cc                                                           432

<210> SEQ ID NO 71
<211> LENGTH: 17
<212> TYPE: PRT
<213> ORGANISM: Artificial Sequence
<220> FEATURE:
<223> OTHER INFORMATION: Based on Homo sapiens
<220> FEATURE:
<221> NAME/KEY: MOD_RES
<222> LOCATION: 5
<223> OTHER INFORMATION: Xaa=bAla

<400> SEQUENCE: 71

Gly Cys Gly Lys Xaa Phe Ala Lys Leu Ala Ala Arg Leu Tyr Arg Lys
1               5                   10                  15

Ala

<210> SEQ ID NO 72
<211> LENGTH: 5
<212> TYPE: PRT
<213> ORGANISM: Artificial Sequence
<220> FEATURE:
<223> OTHER INFORMATION: Based on Homo sapiens
<220> FEATURE:
<221> NAME/KEY: VARIANT
<222> LOCATION: (1)...(5)
<223> OTHER INFORMATION: Xaa is any amino acid

<400> SEQUENCE: 72

Xaa Xaa Xaa Xaa Tyr
1               5

<210> SEQ ID NO 73
<211> LENGTH: 5
<212> TYPE: PRT
<213> ORGANISM: Artificial Sequence
<220> FEATURE:
<223> OTHER INFORMATION: based on Homo sapiens

<400> SEQUENCE: 73

Gly Lys Lys Lys Lys
1               5

```
<210> SEQ ID NO 74
<211> LENGTH: 7
<212> TYPE: PRT
<213> ORGANISM: Artificial Sequence
<220> FEATURE:
<223> OTHER INFORMATION: based on Homo sapiens

<400> SEQUENCE: 74

Gly Arg Gly Asp Ser Pro Gly
  1               5

<210> SEQ ID NO 75
<211> LENGTH: 11
<212> TYPE: PRT
<213> ORGANISM: Artificial Sequence
<220> FEATURE:
<223> OTHER INFORMATION: Based on Homo sapiens

<400> SEQUENCE: 75

Gly Cys Asn Asn Arg Gly Asp Asn Asn Cys Gly
  1               5                  10
```